(12) United States Patent
Cornell et al.

(10) Patent No.: US 10,934,593 B2
(45) Date of Patent: Mar. 2, 2021

(54) COMPOSITIONS AND METHODS FOR PREDICTING RESPONSE AND RESISTANCE TO CDK4/6 INHIBITION

(71) Applicant: DANA-FARBER CANCER INSTITUTE, INC., Boston, MA (US)

(72) Inventors: Liam Cornell, Brookline, MA (US); Geoffrey I. Shapiro, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 66 days.

(21) Appl. No.: 16/047,810

(22) Filed: Jul. 27, 2018

(65) Prior Publication Data
US 2019/0032146 A1 Jan. 31, 2019

Related U.S. Application Data

(60) Provisional application No. 62/538,319, filed on Jul. 28, 2017.

(51) Int. Cl.
| | |
|---|---|
| *C12Q 1/6886* | (2018.01) |
| *C12Q 1/6809* | (2018.01) |
| *G16H 20/10* | (2018.01) |
| *G16B 30/00* | (2019.01) |
| *A61K 31/506* | (2006.01) |
| *A61K 31/519* | (2006.01) |
| *G16B 25/10* | (2019.01) |
| *G16H 50/20* | (2018.01) |
| *G16B 40/00* | (2019.01) |
| *C12N 15/113* | (2010.01) |

(52) U.S. Cl.
CPC .......... *C12Q 1/6886* (2013.01); *A61K 31/506* (2013.01); *A61K 31/519* (2013.01); *C12Q 1/6809* (2013.01); *G16B 25/10* (2019.02); *G16B 30/00* (2019.02); *G16H 20/10* (2018.01); *G16H 50/20* (2018.01); *C12N 15/1137* (2013.01); *C12Q 2600/106* (2013.01); *C12Q 2600/112* (2013.01); *C12Q 2600/118* (2013.01); *C12Q 2600/166* (2013.01); *C12Q 2600/178* (2013.01); *C12Y 207/11022* (2013.01); *G16B 40/00* (2019.02)

(58) Field of Classification Search
None
See application file for complete search history.

(56) References Cited

U.S. PATENT DOCUMENTS

2001/0051344 A1* 12/2001 Shalon .................. B82Y 30/00
435/6.11

OTHER PUBLICATIONS

Lucentini (The Scientist, 2004, vol. 18, p. 20) (Year: 2004).*
Cobb et al (Crit Care Med 2002 vol. 30 p. 2711) (Year: 2002).*
Enard et al. (Science 2002 vol. 296 p. 340) (Year: 2002).*
Arnold, Andrew, et al., "Cyclin D1 in Breast Cancer Pathogenesis", Journal of Clinical Oncology, 23:4215-4224, vol. 23, No. 18, Jun. 20, 2005, p. 4215.
The Cancer Genome Atlas Network, "Comprehensive Molecular Portraits of Human Breast Tumours", Nature, Oct. 4, 2012, vol. 490.
Chiron, David, et al., "Induction of Prolonged Early G1 Arrest by CDK4/CDK6 Inhibition Reprograms Lymphoma Cells for Durable PI3Kδ Inhibition Through PIK3IP1", Cell Cycle 12:12, 1892-1900; Jun. 15, 2013.
Choi, Young Eun, et al., "MicroRNAs Down-Regulate Homologous Recombination in the G1 Phase of Cycling Cells to Maintain Genomic Stability", eLife 2014, pp. 1-21.
Condorelli, R., et al., "Polyclonal RB1 Mutations and Acquired Resistance to CDK 4/6 Inhibitors in Patients with Metastatic Breast Cancer", Annals of Oncology 29:640-645, 2018.
Cristofanilli, Massimo, et al., "Fulvestrant Plus Palbociclib Versus Fulvestrant Plus Placebo for Treatment of Hormone-Receptor-Positive, HER2-Negative Metastatic Breast Cancer that Progressed on Previous Endocrine Therapy (PALOMA-3): Final Analysis of the Multicentre, Double-Blind, Phase 3 Randomised Controlled Trial", Articles, Lancet Oncol; Apr. 2016, vol. 17, 425-39.
Dickler, Maura N., et al., "MONARCH 1, A Phase II Study of Abemaciclib, a CDK4 and CDK6 Inhibitor, as a Single Agent, in Patients with Refractory HR+/HER2-Metastatic Breast Cancer", Clinical Cancer Research; 23(17), Sep. 1, 2017, p. 5218.
Di Liberto, Maurizio, et al., "PIK3IP1 Inhibition of PI3K in G1 Arrest Induced by CDK4 Inhibition Reprograms MCL for Ibrutinib Therapy", Blood 2016, 128:610.
Elsheikh, Somaia, et al., "CCND1 Amplification and Cyclin D1 Expression in Breast Cancer and Their Relation with Proteomic Subgroups and Patient Outcome", Breast Cancer Res Treat (2008), 109:325-335.
Finn, Richard S., M.D., et al., "Palbociclib and Letrozole in Advanced Breast Cancer", The New England Journal of Medicine, Nov. 17, 2016, vol. 375, No. 20.
Fry, David W., et al., "Specific Inhibition of Cyclin-Dependent Kinase 4/6 by PD 0332991 and Associated Antitumor Activity in Human Tumor Xenografts", Molecular Cancer Therapeutics, 2004:3(11), Nov. 2004.
Goetz, Matthew P., et al., "MONARCH 3: Abemaciclib as Initial Therapy for Advanced Breast Cancer", Journal of Clinical Oncology, vol. 35, No. 32, Nov. 10, 2017.
Hannafon, Bethany N., et al., "Plasm Exosome MicroRNAs are Indicative of Breast Cancer", Breast Cancer Research (2016), 18:90.
Herrera-Abreu, Maria Teresa, et al., "Early Adaptation and Acquired Resistance to CDK4/6 Inhibition in Estrogen Receptor-Positive Breast Cancer" AACR, Cancer Research; 76(8), Apr. 15, 2016, p. 2301.

(Continued)

*Primary Examiner* — Katherine D Salmon
(74) *Attorney, Agent, or Firm* — Burns & Levinson, LLP; Daniel W. Clarke

(57) ABSTRACT

The present invention relates to compositions and methods for detecting CDK4/6 response and resistance.

17 Claims, 60 Drawing Sheets

(56) References Cited

OTHER PUBLICATIONS

Hortobagyi, G.N., et al., "Ribociclib as First-Line Therapy for HR-Positive, Advanced Breast Cancer", The New England Journal of Medicine, 375:18, Nov. 3, 2016, p. 1738.
Infante, Jeffrey R., et al., "A Phase I Study of the Cyclin-Dependent Kinase 4/6 Inhibitor Ribociclib (LEE011) in Patients With Advanced Solid Tumors and Lymphomas", Clinical Cancer Research; 22(23), Dec. 1, 2016.
Jansen, Valerie M., et al., "Kinome-Wide RNA Interference Screen Reveals a Role for PDK1 in Acquired Resistance to CDK4/6 Inhibition in ER-Positive Breast Cancer", AACR Cancer Research; 77(9), May 1, 2017.
Kosaka, Nobuyoshi, et al., "Secretary Mechanisms and Intercellular Transfer of MicroRNAs in Living Cells", The Journal of Biological Chemistry, vol. 285, No. 23, pp. 17442-17452, Jun. 4, 2010.
Liu, Fang, et al., "Cdk4/6 Inhibition Induces Epithelial-Mesenchymal Transition and Enhances Invasiveness in Pancreatic Cancer Cells", Molecular Cancer Therapeutics; 11(10), Oct. 2012.
Massague, Joan, "G1 Cell-Cycle Control and Cancer", Nature, Nov. 18, 2004, vol. 432.
Mittelbrunn, Maria, et al., "Unidirectional Transfer of MicroRNA-Loaded Exosomes from T Cells to Antigen-Presenting Cells", Nature Communications, 2:282, Published Apr. 19, 2011.
Montecalvo, Angela, et al., "Mechanism of Transfer of Functional MicroRNAs Between Mouse Dendritic Cells via Exosomes", Blood, Jan. 19, 2012, vol. 119, No. 3.
Patnaik, Amita, et al., "Efficacy and Safety of Abemaciclib, an Inhibitor of CDK4 and CDK6, for Patients with Breast Cancer, Non-Small Cell Lung Cancer, and Other Solid Tumors", AACR Cancer Discovery, Jul. 2016.
Perou, Charles M., et al., "Molecular Portraits of Human Breast Tumours", Nature, vol. 406, Aug. 17, 2000, p. 747.
Rabinowits, Guilherme, et al., "Exosomal MicroRNA: A Diagnostic Marker for Lung Cancer", Clinical Lung Cancer, vol. 10, No. 1, Jan. 2009, pp. 42-46.
Roberts, Patrick J., et al., "Multiple Roles of Cyclin-Dependent Kinase 4/6 Inhibitors in Cancer Therapy", Articles/JNCI, vol. 104, Issue 6, Mar. 21, 2012.
Roy, Pankaj G., et al., "High CCND1 Amplification Identifies a Group of Poor Prognosis Women with Estrogen Receptor Positive Breast Cancer", International Journal of Cancer, 127, 355-360, 2010.
Sledge, George W., Jr., et al., "MONARCH 2: Abemaciclib in Combination With Fulvestrant in Women With HR+/HER2- Advanced Breast Cancer Who Had Progressed While Receiving Endocrine Therapy", Journal of Clinical Oncology, vol. 35, No. 25, Sep. 1, 2017.
Tsubari, Minna, et al., "Hepatocyte Growth Factor Releases Mink Epithelial Cells from Transforming Growth Factor β1-Induced Growth Arrest by Restoring Cdk6 Expression and Cyclin E-Associated Cdk2 Activity", Molecular and Cellular Biology, May 1999, pp. 3654-3663.
Turner, Nicholas C., M.D., et al., "Palbociclib in Hormone-Receptor-Positive Advanced Breast Cancer", The New England Journal of Medicine, Jul. 16, 2015, vol. 373, No. 3, p. 209.
Valencia-Sanchez, Marco Antonio, et al., "Control of Translation and mRNA Degradation by miRNAs and siRNAs", Genes & Development (2006) 20:55-524.
Velasco-Velazquez, Marco, et al., "Examining the Role of Cyclin D1 in Breast Cancer", Future Oncology (2011) 7(6), pp. 753-765.
Wang, Lisheng, et al., "Pharmacologic Inhibition of CDK4/6: Mechanistic Evidence for Selective Activity or Acquired Resistance in Acute Myeloid Leukemia", Blood, Sep. 15, 2007, vol. 110, No. 6, p. 2075.
Yang, C., et al., "Acquired CDK6 Amplification Promotes Breast Cancer Resistance to CDK4/6 Inhibitors and Loss of ER Signaling and Dependence", Oncogene (2017) 36, 2255-2264.
Yu, Qunyan, et al., "Requirement for CDK4 Kinase Function in Breast Cancer", Cancer Cell 9, 23-32, Jan. 2006.
Zhang, Fan, et al., "Ectopic Expression of Cdk6 Circumvents Transforming Growth Factor-β Mediated Growth Inhibition", Oncogene (2001) 20, 5888-5896.

* cited by examiner

FIG. 5B

| INCREASED expression in resistant cells | |
|---|---|
| Name | P-Value |
| hsa-miR-181a-5p | 9.56E-06 |
| hsa-miR-1285-3p | 3.26E-05 |
| hsa-miR-4472* | 1.47E-04 |
| hsa-miR-1973 | 2.68E-04 |
| hsa-miR-1248 | 3.16E-04 |
| hsa-miR-4732-5p | 4.64E-04 |
| hsa-miR-302a-3p | 4.98E-04 |
| hsa-miR-4764-3p | 5.92E-04 |
| hsa-miR-675-3p | 6.59E-04 |
| hsa-miR-223-3p | 6.75E-04 |
| hsa-miR-23a-5p | 7.96E-04 |
| hsv2-miR-H24 | 8.32E-04 |
| hsa-miR-1238-3p | 9.10E-04 |
| hsa-miR-4273 | 1.07E-03 |
| hsa-miR-432-5p | 1.19E-03 |
| hsa-miR-181b-5p | 1.32E-03 |
| hsa-miR-145-5p | 1.34E-03 |
| hsa-miR-1273a | 1.67E-03 |
| hsa-miR-1243 | 2.24E-03 |
| hsa-miR-4423-3p* | 5.45E-03 |

| Decreased expression in resistant cells | |
|---|---|
| Name | P-Value |
| hsa-miR-4497* | 3.57E-07 |
| hsa-miR-5002-5p | 3.78E-07 |
| hsa-miR-3925-3p* | 1.26E-06 |
| hsa-miR-4645-5p | 3.01E-06 |
| hsa-miR-3178 | 3.76E-06 |
| hsa-miR-874-3p* | 4.36E-06 |
| hsa-miR-3940-5p | 6.68E-06 |
| hsa-miR-3158-5p* | 1.54E-05 |
| hsa-miR-1255b-5p | 2.72E-05 |
| hsa-miR-4503 | 3.37E-05 |
| hsa-miR-4695-3p* | 4.51E-05 |
| hsa-miR-1255a | 4.99E-05 |
| hsa-miR-663a* | 6.83E-05 |
| hsa-miR-4456* | 6.83E-05 |
| hsa-miR-1260b | 6.86E-05 |
| hsa-miR-210-3p | 7.43E-05 |
| hsa-miR-378c | 7.99E-05 |
| hsa-miR-802 | 8.55E-05 |
| hsv2-miR-H9-3p | 1.54E-04 |
| hsa-miR-186-5p* | 7.33E-03 |

FIG. 6C

SMAD4:

3'UTR

GGGTCTGACATCCTGCCCCAAGG
 : |   |    | | | : |  | | | | | :
GGTGGGTTACTGGATGAGGTTCT miR-432-5p
(p=0.014)

TGFBR3:

3'UTR

ATTGAAAATGACCAAAATCAGGA
 | | | | | | |   |   : | | : | |
GGTGGGTACTGGATGAGGTTCT miR-432-5p
(p=0.032)

FIG. 6D

| | miRNA pull down | | mRNA Expression | |
|---|---|---|---|---|
| Gene | Fold Enrichment (Total RNA vs pulldown) [FKPM] | P-Value | mRNA FC (parental vs Resistant) | P-Value |
| TGFB1 | 4.4 | 0.0085 | 0.8 | 0.07 |
| TGFB2 | 30.1 | 0.0241 | 0.8 | 0.21 |
| TGFB3 | 4.0 | 0.0043 | 1.2 | 0.21 |
| TGFBR1 | - | | 1.0 | 0.98 |
| TGFBR2 | - | | 1.0 | 0.72 |
| TGFBR3 | 2.0 | 0.0037 | 0.2 | 0.01 |
| SMAD3 | 6.2 | 0.0236 | 1.0 | 0.39 |
| SMAD4 | 3.9 | 0.0036 | 0.6 | 0.03 |
| SMAD7 | 22.9 | 0.0098 | 1.0 | 0.77 |
| SMAD9 | 5.0 | 0.0006 | 1.2 | 0.31 |

*Cells removed from drug exposure for > 7 weeks classed as "Ex-resistant".

COMPOSITIONS AND METHODS FOR PREDICTING RESPONSE AND RESISTANCE TO CDK4/6 INHIBITION

RELATED APPLICATIONS

This application claims the benefit of priority under 35 U.S.C. § 119(e) to U.S. Provisional Application No. 62/538,319, filed Jul. 28, 2017, which is incorporated herein by reference in its entirety.

GOVERNMENT LICENSE RIGHTS

This invention was made with government support under grant number P50 CA168504 awarded by the National Institutes of Health. The government has certain rights in the invention.

BACKGROUND OF THE INVENTION

Cyclin D-dependent kinase activity is a driving factor for carcinogenesis in more than 80% of hormone receptor-positive breast cancers. Additionally, CCND1 amplification or overexpression portends poor survival. However, cyclin dependent kinase 4 and 6 (CDK 4/6) inhibitor-based treatment is complicated by the development of acquired resistance. Prior to the invention described herein, the process by which resistance to CDK 4/6 inhibitor treatment arises was unknown. As such, there is a pressing need to identify biomarkers of resistance of CDK4/6 inhibitor treatment.

SUMMARY OF THE INVENTION

The present invention is based upon the surprising discovery of a biomarker for CDK4/6 inhibitor response and resistance in cancer. Specifically, a micro ribonucleic acid (miRNA), miR-432-5p, is excreted in exosomes from resistant cells and transmits resistance to CDK4/6 inhibition. As described in detail below, this miRNA is detected via real-time polymerase chain reaction (PCR) analysis of RNA. Specifically as described in detail below, microRNA-mediated suppression of the transforming growth factor beta (TGF-β) pathway confers transmissible and reversible CDK4/6 inhibitor resistance.

Accordingly, described herein are methods of determining whether inhibition of cyclin-dependent kinase 4 CDK4 and/or CDK6 in a subject with neoplasia will result in clinical benefit in the subject. First, a test sample is obtained from a subject having or at risk of developing neoplasia. Next, the expression level of a micro ribonucleic acid (miRNA) in the test sample is determined. The expression level of the miRNA in the test sample is compared with the expression level of the miRNA in a reference sample, and finally, it is determined whether CDK4/6 will inhibit neoplasia in the subject if the expression level of the miRNA in the test sample is differentially expressed as compared to the level of the miRNA in the reference sample. Preferably, the subject is a human.

Suitable neoplasias include breast cancer and parotid cancer. Other exemplary neoplasias include pancreatic cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

In some cases, the CDK4/6 inhibitor comprises palbociclib, abemacyclib, or ribociclib. In one aspect, the CDK4/6 inhibitor has been administered to the subject.

For example, the test sample is obtained from the neoplasia or from blood in the subject. Exemplary samples include a plasma sample, a serum sample, or a blood sample. For example, the test sample comprises circulating blood exosomes or circulating tumor cells. In some cases, the reference sample is obtained from healthy normal tissue, neoplasia that received a clinical benefit from CDK4/6 inhibition, or neoplasia that did not receive a clinical benefit from CDK4/6 inhibition. In another example, the reference sample is obtained from healthy normal tissue from the same individual as the test sample or one or more healthy normal tissues from different individuals.

In one aspect, the miRNA comprises an exosomal miRNA selected from the group consisting of miR-1973, miR-432-5p, miR-874-3p, miR-4695-3p, and miR-186-5p. For example, the method comprises determining that inhibition of CDK4/6 in the subject will not result in clinical benefit in the subject if the expression level of miR-432-5p in the test sample is higher than the level of miR-432-5p in the reference sample, e.g., at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the level of miR-432-5p in the reference sample.

For example, the expression level of miR-432-5p in the test sample is upregulated (i.e., increased) by at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, at least 100 fold, at least 125 fold, at least 150 fold, at least 175 fold, at least 200 fold, at least 250 fold, at least 300 fold, at least 350 fold, at least 400 fold or at least 500 fold as compared to the level of the miR-432-5p in the reference sample.

In some cases, the level of CDK6 protein in the test sample is increased as compared to the level of CDK6 protein in the reference sample.

In one aspect, the method comprises determining that inhibition of CDK4/6 in the subject will not result in clinical benefit in the subject if the expression level of mothers against decapentaplegic homolog 4 (SMAD4) protein in the test sample is decreased as compared to the level of SMAD4 protein in the reference sample. In some cases, the method further comprises administering to the subject a SMAD4 agonist, along with the CDK4/6 inhibitor, thereby treating the neoplasia, wherein the SMAD4 agonist comprises a SMAD4 polypeptide.

For example, the expression level of the miRNA is detected via quantitative real-time reverse transcriptase polymerase chain reaction (real time RT-PCR). In other cases, the expression level of the miRNA is detected via an Affymetrix Gene Array hybridization, next generation sequencing, ribonucleic acid sequencing (RNA-seq), or nanoString nCounter expression panels.

In some cases, the method further comprises treating the subject with a chemotherapeutic agent, radiation therapy, cryotherapy, hormone therapy, or immunotherapy.

In other cases, the method further comprises administering to the subject an inhibitor of miR-432-5p along with the CDK4/6 inhibitor, thereby treating the cancer. For example, the inhibitor comprises a small molecule inhibitor, RNA interference (RNAi), or an antibody. Exemplary miR-432-5p inhibitors include those provided by Sigma-Aldrich® (e.g., catalogue number HSTUD0572; Sigma-Aldrich®: St. Louis, Mo.), SwitchGear Genomics (e.g., product number INH0392; SwitchGear Genomics; Carlsbad, Calif.), and Active Motif® (e.g., product ID INH0392; Active Motif®: Carlsbad, Calif.).

Optionally, the method further comprises administering to the subject a CDK4/6 inhibitor at least 6 weeks after cessation of CDK4/6 inhibitor treatment, thereby treating the neoplasia. For example, the method further comprises administering to the subject a CDK4/6 inhibitor at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 6 months, or at least one year after cessation of CDK4/6 inhibitor treatment, thereby treating the neoplasia. Alternatively, the method further comprises administering to the subject a CDK4/6 inhibitor at least 1 week after cessation of CDK4/6 inhibitor treatment, thereby treating the neoplasia.

In some cases, clinical benefit in the subject comprises complete or partial response as defined by response evaluation criteria in solid tumors (RECIST) or stable disease as defined by RECIST.

Also provided are methods of re-sensitizing a cancer cell to CDK4/6 inhibition comprising administering a miR-432-5p inhibitor to the cancer cell. Methods of treating neoplasia in a subject are carried out by administering a CDK4/6 inhibitor to the subject and administering an inhibitor of miR-432-5p to the subject, thereby treating neoplasia in the subject.

In some cases, the inhibitor is administered at a dose of 1-1000 nM, e.g., about 1 nM, about 5 nM, about 10 nM, about 25 nM, about 50 nM, about 75 nM, about 100 nM, about 200 nM, about 300 nM, about 400 nM, about 500 nM, about 600 nM, about 700 nM, about 800 nM, about 900 nM, or about 1000 nM. In one aspect, the inhibitor is administered at least one time per month, e.g., twice per month, once per week, twice per week, once per day, twice per day, every 8 hours, every 4 hours, every 2 hours, or every hour Also provided are kits comprising reagents for assaying a biological sample from a subject with neoplasia for aberrant expression of miR-432-5p.

Methods of monitoring therapeutic efficacy of inhibition of CDK4/6 in a subject with neoplasia are carried out by administering an effective amount of a CDK4/6 inhibitor to the subject; obtaining a first test sample from the subject; determining the expression level of a micro ribonucleic acid (miRNA) in the test sample; comparing the expression level of the miRNA in the first test sample with the expression level of the miRNA in a reference sample; and determining whether CDK4/6 will inhibit neoplasia in the subject if the expression level of the miRNA in the first test sample is differentially expressed as compared to the level of the miRNA in the reference sample.

For example, the test sample is obtained from the neoplasia or from blood in the subject. In some cases, the miRNA comprises an exosomal miRNA selected from the group consisting of miR-1973, miR-432-5p, miR-874-3p, miR-4695-3p, and miR-186-5p.

In one aspect, the method comprises determining that inhibition of CDK4/6 in the subject will not result in clinical benefit in the subject if the expression level of miR-432-5p in the test sample is higher than the level of miR-432-5p in the reference sample. If the expression level of miR-432-5p in the test sample is higher than the level of miR-432-5p in the reference sample, administration of the CDK4/6 inhibitor is ceased. Subsequently, the method further comprises obtaining a second test sample from the subject; determining the expression level of a micro ribonucleic acid (miRNA) in the second test sample; comparing the expression level of the miRNA in the second test sample with the expression level of the miRNA in a first test sample; and administering the CDK4/6 inhibitor to the subject if the expression level of the miRNA in the second test sample is lower than the level of the miRNA in the first test sample.

As described in detail below, biomarkers that distinguish response and resistance to CDK4/6 inhibition in cancer patients were identified herein. For example, a suitable distinguishing biomarker includes miR-432-5p. An exemplary miR-432-5p nucleic acid sequence is set forth below (SEQ ID NO: 5):

```
ucuuggagua ggucauuggg ugg
```

An additional exemplary miR-432-5p nucleic acid sequence is provided at NCBI Accession No. LM379772, version LM379772.1, incorporated herein by reference, and reproduced below (SEQ ID NO: 6):

```
tcttggagta ggtcattggg tgg
```

An exemplary miR-432 nucleic acid sequence is provided at NCBI Accession No. NR_030173, version NR_030173.1, incorporated herein by reference, and reproduced below (SEQ ID NO: 7):

```
 1  tgactcctcc aggtcttgga gtaggtcatt gggtggatcc tctatttcct tacgtgggcc 61  actggatggc tcctccatgt cttggagtag atca
```

An exemplary primer (complementary sequence) used to detect mature miRNA (miR-432-5P) is set forth below (SEQ ID NO: 1; see, FIG. 6C):

```
        ggtgggttac tggatgaggt tct
```

By "mothers against decapentaplegic homolog 4 (SMAD4) nucleic acid molecule" is meant a polynucleotide encoding a SMAD4 polypeptide. An exemplary SMAD4 nucleic acid molecule is provided at NCBI Accession No. NM_005359, version NM_005359.5, incorporated herein by reference, and reproduced below (SEQ ID NO: 8):

```
   1    atgctcagtg gcttctcgac aagttggcag caacaacacg gccctggtcg tcgtcgccgc
  61    tgcggtaacg gagcggtttg ggtggcggag cctgcgttcg cgccttcccg ctctcctcgg
 121    gaggcccttc ctgctctccc ctaggctccg cggccgccca gggggtggga gcgggtgagg
 181    ggagccaggc gcccagcgag agaggccccc cgccgcaggg cggcccggga gctcgaggcg
 241    gtccggcccg cgcgggcagc ggcgcggcgc tgaggagggg cggcctggcc gggacgcctc
 301    ggggcggggg ccgaggagct ctccgggccg ccggggaaag ctacgggccc ggtgcgtccg
 361    cggaccagca gcgcgggaga gcggactccc ctcgccaccg cccgagccca ggttatcctg
 421    aatacatgtc taacaatttt ccttgcaacg ttagctgttg tttttcactg tttccaaagg
 481    atcaaaattg cttcagaaat tggagacata tttgatttaa aaggaaaaac ttgaacaaat
 541    ggacaatatg tctattacga atacaccaac aagtaatgat gcctgtctga gcattgtgca
 601    tagtttgatg tgccatagac aaggtggaga gagtgaaaca tttgcaaaaa gagcaattga
 661    aagtttggta aagaagctga aggagaaaaa agatgaattg gattctttaa taacagctat
 721    aactacaaat ggagctcatc ctagtaaatg tgttaccata cagagaacat tggatgggag
 781    gcttcaggtg gctggtcgga aaggatttcc tcatgtgatc tatgcccgtc tctggaggtg
 841    gcctgatctt cacaaaaatg aactaaaaca tgttaaatat tgtcagtatg cgtttgactt
 901    aaaatgtgat agtgtctgtg tgaatccata tcactacgaa cgagttgtat cacctggaat
 961    tgatctctca ggattaacac tgcagagtaa tgctccatca agtatgatgg tgaaggatga
1021    atatgtgcat gactttgagg acagccatc gttgtccact gaaggacatt caattcaaac
1081    catccagcat ccaccaagta atcgtgcatc gacagagaca tacagcaccc cagctctgtt
1141    agccccatct gagtctaatg ctaccagcac tgccaacttt cccaacattc ctgtggcttc
1201    cacaagtcag cctgccagta tactgggggg cagccatagt gaaggactgt tgcagatagc
1261    atcagggcct cagccaggac agcagcagaa tggatttact ggtcagccag ctacttacca
1321    tcataacagc actaccacct ggactggaag taggactgca ccatacacac taatttgcc
1381    tcaccaccaa aacggccatc ttcagcacca cccgcctatg ccgcccatc ccggacatta
1441    ctggcctgtt cacaatgagc ttgcattcca gcctcccatt tccaatcatc ctgctcctga
1501    gtattggtgt tccattgctt actttgaaat ggatgttcag gtaggagaga catttaaggt
1561    tccttcaagc tgccctattg ttactgttga tggatacgtg gaccccttctg gaggagatcg
1621    cttttgtttg ggtcaactct ccaatgtcca caggacagaa gccattgaga gagcaaggtt
1681    gcacataggc aaaggtgtgc agttggaatg taaaggtgaa ggtgatgttt gggtcaggtg
1741    ccttagtgac cacgcggtct ttgtacagag ttactactta gacagagaag ctgggcgtgc
1801    acctggagat gctgttcata agatctaccc aagtgcatat ataaaggtct ttgatttgcg
1861    tcagtgtcat cgacagatgc agcagcaggc ggctactgca caagctgcag cagctgccca
1921    ggcagcagcc gtggcaggaa acatccctgg cccaggatca gtaggtggaa tagctccagc
```

-continued

```
1981  tatcagtctg tcagctgctg ctggaattgg tgttgatgac cttcgtcgct tatgcatact
2041  caggatgagt tttgtgaaag gctggggacc ggattaccca agacagagca tcaaagaaac
2101  accttgctgg attgaaattc acttacaccg ggccctccag ctcctagacg aagtacttca
2161  taccatgccg attgcagacc cacaaccttt agactgaggt cttttaccgt tggggccctt
2221  aaccttatca ggatggtgga ctacaaaata caatcctgtt tataatctga agatatattt
2281  cactttttgtt ctgctttatc ttttcataaa gggttgaaaa tgtgtttgct gccttgctcc
2341  tagcagacag aaactggatt aaaacaattt ttttttttcct cttcagaact tgtcaggcat
2401  ggctcagagc ttgaagatta ggagaaacac attcttatta attcttcacc tgttatgtat
2461  gaaggaatca ttccagtgct agaaaattta gcccttttaaa acgtcttaga gccttttatc
2521  tgcagaacat cgatatgtat atcattctac agaataatcc agtattgctg attttaaagg
2581  cagagaagtt ctcaaagtta attcacctat gttattttgt gtacaagttg ttattgttga
2641  acatacttca aaaataatgt gccatgtggg tgagttaatt ttaccaagag taactttact
2701  ctgtgtttaa aaagtaagtt aataatgtat tgtaatcttt catccaaaat attttttgca
2761  agttatatta gtgaagatgg tttcaattca gattgtcttg caacttcagt tttatttttg
2821  ccaaggcaaa aaactcttaa tctgtgtgta tattgagaat cccttaaaat taccagacaa
2881  aaaaatttaa aattacgttt gttattccta gtggatgact gttgatgaag tatactttttc
2941  ccctgttaaa cagtagttgt attcttctgt atttctaggc acaaggttgg ttgctaagaa
3001  gcctataaga ggaatttctt ttccttcatt catagggaaa ggttttgtat ttttttaaaaac
3061  actaaaagca gcgtcactct acctaatgtc tcactgttct gcaaaggtgg caatgcttaa
3121  actaaataat gaataaactg aatattttgg aaactgctaa attctatgtt aaatactgtg
3181  cagaataatg gaaacattac agttcataat aggtagtttg gatatttttg tacttgattt
3241  gatgtgactt ttttggtat aatgtttaaa tcatgtatgt tatgatattg tttaaaattc
3301  agttttgta tcttggggca agactgcaaa ctttttttata tcttttggtt attctaagcc
3361  ctttgccatc aatgatcata tcaattggca gtgactttgt atagagaatt taagtagaaa
3421  agttgcagat gtattgactg taccacagac acaatatgta tgcttttttac ctagctggta
3481  gcataaataa aactgaatct caacatacaa agttgaattc taggtttgat ttttaagatt
3541  ttttttttct tttgcacttt tgagtccaat ctcagtgatg aggtaccttc tactaaatga
3601  caggcaacag ccagttctat tgggcagctt tgttttttttc cctcacactc taccgggact
3661  tccccatgga cattgtgtat catgtgtaga gttggttttt tttttttta atttttattt
3721  tactatagca gaaatagacc tgattatcta caagatgata aatagattgt ctacaggata
3781  aatagtatga aataaaatca aggattatct ttcagatgtg tttacttttg cctggagaac
3841  ttttagctat agaaacactt gtgtgatgat agtcctcctt atatcacctg gaatgaacac
3901  agcttctact gccttgctca gaaggtcttt taaatagacc atcctagaaa ccactgagtt
3961  tgcttatttc tgtgatttaa acatagatct tgatccaagc tacatgactt ttgtctttaa
4021  ataacttatc taccacctca tttgtactct tgattactta caaattcttt cagtaaacac
4081  ctaatttttct tctgtaaaag tttggtgatt taagttttat tggcagtttt ataaaaagac
4141  atcttctcta gaaattgcta acttttaggtc cattttactg tgaatgagga ataggagtga
4201  gttttagaat aacagatttt taaaaatcca gatgatttga ttaaaacctt aatcatacat
4261  tgacataatt cattgcttct ttttttttgag atatggagtc ttgctgtgtt gcccaggcag
4321  gagtgcagtg gtatgatctc agctcactgc aacctctgcc tcccgggttc aactgattct
```

-continued

```
4381  cctgcctcag cctccctggt agctaggatt acaggtgccc gccaccatgc ctggctaact
4441  tttgtagttt tagtagagac ggggttttgc ctgttggcca ggctggtctt gaactcctga
4501  cctcaagtga tccatccacc ttggcctccc aaagtgctgg gattacgggc gtgagccact
4561  gtccctggcc tcattgttcc cttttctact ttaaggaaag ttttcatgtt taatcatctg
4621  gggaaagtat gtgaaaaata tttgttaaga agtatctctt tggagccaag ccacctgtct
4681  tggtttcttt ctactaagag ccataaagta tagaaatact tctagttgtt aagtgcttat
4741  atttgtacct agatttagtc acacgctttt gagaaaacat ctagtatgtt atgatcagct
4801  attcctgaga gcttggttgt taatctatat ttctatttct tagtggtagt catctttgat
4861  gaataagact aaagattctc acaggtttaa aattttatgt ctacttttaag ggtaaaatta
4921  tgaggttatg gttctgggtg ggttttctct agctaattca tatctcaaag agtctcaaaa
4981  tgttgaattt cagtgcaagc tgaatgagag atgagccatg tacacccacc gtaagacctc
5041  attccatgtt tgtccagtgc ctttcagtgc attatcaaag gaatccttc atggtgttgc
5101  ctttattttc cggggagtag atcgtgggat atagtctatc tcattttaa tagtttaccg
5161  cccctggtat acaaagataa tgacaataaa tcactgccat ataaccttgc ttttccaga
5221  aacatggctg ttttgtattg ctgtaaccac taaataggtt gcctatacca ttcctcctgt
5281  gaacagtgca gatttacagg ttgcatggtc tggcttaagg agagccatac ttgagacatg
5341  tgagtaaact gaactcatat tagctgtgct gcatttcaga cttaaaatcc attttgtgg
5401  ggcagggtgt ggtgtgtaaa ggggggtgtt tgtaatacaa gttgaaggca aaataaaatg
5461  tcctgtctcc cagatgatat acatcttatt attttttaaag tttattgcta attgtaggaa
5521  ggtgagttgc aggtatcttt gactatggtc atctggggaa ggaaaatttt acatttttact
5581  attaatgctc cttaagtgtc tatggaggtt aaagaataaa atggtaaatg tttctgtgcc
5641  tggtttgatg gtaactggtt aatagttact caccattttta tgcagagtca cattagttca
5701  cacctttct gagagccttt gggagaagc agttttattc tctgagtgga acagagttct
5761  ttttgttgat aatttctagt ttgctcccctt cgttattgcc aactttactg gcattttatt
5821  taatgatagc agattgggaa aatggcaaat ttaggttacg gaggtaaatg agtatatgaa
5881  agcaattacc tctaaagcca gttaacaatt attttgtagg tggggtacac tcagcttaaa
5941  gtaatgcatt ttttttttccc gtaaaggcag aatccatctt gttgcagata gctatctaaa
6001  taatctcata tcctcttttg caaagactac agagaatagg ctatgacaat cttgttcaag
6061  cctttccatt ttttccctg ataactaagt aatttctttg aacataccaa gaagtatgta
6121  aaaagtccat ggccttattc atccacaaag tggcatccta ggcccagcct tatccctagc
6181  agttgtccca gtgctgctag gttgcttatc ttgtttatct ggaatcactg tggagtgaaa
6241  ttttccacat catccagaat tgccttattt aagaagtaaa acgttttaat ttttagcctt
6301  tttttggtgg agttatttaa tatgtatatc agaggatata ctagatggta acatttcttt
6361  ctgtgcttgg ctatctttgt ggacttcagg ggcttctaaa acagacagga ctgtgttgcc
6421  tttactaaat ggtctgagac agctatggtt ttgaattttt agttttttttt ttttaaccca
6481  cttcccctcc tggtctcttc cctctctgat aattaccatt catatgtgag tgttagtgtg
6541  cctccttttta gcatttctt cttctctttc tgattcttca tttctgactg cctaggcaag
6601  gaaaccagat aaccaaactt actagaacgt tctttaaaac acaagtacaa actctgggac
6661  aggacccaag acactttcct gtgaagtgct gaaaagacc tcattgtatt ggcatttgat
6721  atcagtttga tgtagcttag agtgcttcct gattcttgct gagtttcagg tagttgagat
6781  agagagaagt gagtcatatt catattttcc ccccttagaat aatattttga aaggtttcat
```

-continued

```
6841  tgcttccact tgaatgctgc tcttacaaaa actggggtta caagggttac taaattagca
6901  tcagtagcca gaggcaatac cgttgtctgg aggacaccag caaacaacac acaacaaagc
6961  aaaacaaacc ttgggaaact aaggccattt gttttgtttt ggtgtcccct ttgaagccct
7021  gccttctggc cttactcctg tacagatatt tttgacctat aggtgccttt atgagaattg
7081  agggtctgac atcctgcccc aaggagtagc taaagtaatt gctagtgttt cagggatt
7141  taacatcaga ctggaatgaa tgaatgaaac ttttgtcct ttttttttct gtttttttt
7201  ttctaatgta gtaaggacta aggaaaacct tggtgaaga caatcatttc tctctgttga
7261  tgtggatact tttcacaccg tttatttaaa tgctttctca ataggtccag agccagtgtt
7321  cttgttcaac ctgaaagtaa tggctctggg ttgggccaga cagttgcact ctctagtttg
7381  ccctctgcca caaatttgat gtgtgacctt tgggcaagtc atttatcttc tctgggcctt
7441  agttgcctca tctgtaaaat gagggagttg gagtagatta attattccag ctctgaaatt
7501  ctaagtgacc ttggctaccct tgcagcagtt ttggatttct tccttatctt tgttctgctg
7561  tttgagggg cttttactt atttccatgt tattcaaagg agactaggct tgatatttta
7621  ttactgttct tttatggaca aaaggttaca tagtatgccc ttaagactta attttaacca
7681  aaggcctagc accaccttag gggctgcaat aaacacttaa cgcgcgtgcg cacgcgcgcg
7741  cgcacacaca cacacacaca cacacacaca cacaggtcag agtttaaggc tttcgagtca
7801  tgacattcta gcttttgaat tgcgtgcaca cacacacgca cgcacacact ctggtcagag
7861  tttattaagg ctttcgagtc atgacattat agcttttgag ttggtgtgtg tgacaccacc
7921  ctcctaagtg gtgtgtgctt gtaattttt ttttcagtga aaatggattg aaaacctgtt
7981  gttaatgctt agtgatatta tgctcaaaac aaggaaattc ccttgaaccg tgtcaattaa
8041  actggtttat atgactcaag aaaacaatac cagtagatga ttattaactt tattcttggc
8101  tcttttagg tccattttga ttaagtgact tttggctgga tcattcagag ctctcttcta
8161  gcctaccctt ggatgagtac aattaatgaa attcatattt tcaaggacct gggagccttc
8221  cttggggctg ggttgagggt gggggtttgg ggagtcctgg tagaggccag cttttgtggta
8281  gctggagagg aagggatgaa accagctgct gttgcaaagg ctgcttgtca ttgatagaag
8341  gactcacggg cttggattga ttaagactaa acatggagtt ggcaaacttt cttcaagtat
8401  tgagttctgt tcaatgcatt ggacatgtga tttaagggaa aagtgtgaat gcttatagat
8461  gatgaaaacc tggtgggctg cagagcccag tttagaagaa gtgagttggg ggttggggac
8521  agatttggtg gtggtatttc ccaactgttt cctcccctaa attcagagga atgcagctat
8581  gccagaagcc agagaagagc cactcgtagc ttctgctttg gggacaactg gtcagttgaa
8641  agtcccagga gttcctttgt ggctttctgt atactttgc ctggttaaag tctgtggcta
8701  aaaaatagtc gaacctttct tgagaactct gtaacaaagt atgttttga ttaaaagaga
8761  aagccaacta aaaaaaaaaa aaaaaaaaa
```

By "mothers against decapentaplegic homolog 4 (SMAD4) polypeptide" is meant a polypeptide or fragment thereof having at least about 85% amino acid identity to NCBI Accession No. NP_005350, version NP_005350.1, incorporated herein by reference, as reproduced below (SEQ ID NO: 9):

```
  1  mdnmsitntp tsndaclsiv hslmchrqgg esetfakrai eslvkklkek kdeldslita
 61  ittngahpsk cvtiqrtldg rlqvagrkgf phviyarlwr wpdlhknelk hvkycqyafd
```

```
                              -continued
121   lkcdsvcvnp  yhyervvspg  idlsgltlqs  napssmmvkd  eyvhdfegqp  slsteghsiq 181   tiqhppsnra  stetystpal  lapsesnats  tanfpnipva  stsqpasilg  gshsegllqi 241   asgpqpgqqq  ngftgqpaty  hhnstttwtg  srtapytpnl  phhqnghlqh  hppmpphpgh 301   ywpvhnelaf  qppisnhpap  eywcsiayfe  mdvqvgetfk  vpsscpivtv  dgyvdpsggd 361   rfclgqlsnv  hrteaierar  lhigkgvqle  ckgegdvwvr  clsdhavfvq  syyldreagr 421   apgdavhkiy  psayikvfdl  rqchrqmqqg  aataqaaaaa  qaaavagnip  gpgsvggiap 481   aislsaaagi  gvddlrrlci  lrmsfvkgwg  pdyprqsike  tpcwieihlh  ralqlldevl 541   htmpiadpqp  ld
```

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

The phrase "aberrant expression" is used to refer to an expression level that deviates from (i.e., an increased or decreased expression level) the normal reference expression level of the gene.

By "agent" is meant any small compound, antibody, nucleic acid molecule, or polypeptide, or fragments thereof.

By "alteration" is meant a change (increase or decrease) in the expression levels or activity of a gene or polypeptide as detected by standard art-known methods such as those described herein. As used herein, an alteration includes at least a 1% change in expression levels, e.g., at least a 2%, 3%, 4%, 5%, 6%, 7%, 8%, 9%, 10%, 20%, 30%, 40%, 50%, 60%, 70%, 80%, 90%, or 100% change in expression levels. For example, an alteration includes at least a 5%-10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

By "binding to" a molecule is meant having a physicochemical affinity for that molecule.

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g., β-galactosidase or luciferase). Depending on the method used for detection, the amount and measurement of the change can vary. Determination of statistical significance is within the ability of those skilled in the art, e.g., the number of standard deviations from the mean that constitute a positive result.

"Detect" refers to identifying the presence, absence, or amount of the agent (e.g., a nucleic acid molecule, for example deoxyribonucleic acid (DNA) or ribonucleic acid (RNA)) to be detected.

By "detectable label" is meant a composition that when linked (e.g., joined—directly or indirectly) to a molecule of interest renders the latter detectable, via, for example, spectroscopic, photochemical, biochemical, immunochemical, or chemical means. Direct labeling can occur through bonds or interactions that link the label to the molecule, and indirect labeling can occur through the use of a linker or bridging moiety which is either directly or indirectly labeled. Bridging moieties may amplify a detectable signal. For example, useful labels may include radioactive isotopes, magnetic beads, metallic beads, colloidal particles, fluorescent labeling compounds, electron-dense reagents, enzymes (for example, as commonly used in an enzyme-linked immunosorbent assay (ELISA)), biotin, digoxigenin, or haptens. When the fluorescently labeled molecule is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, p-phthaldehyde and fluorescamine. The molecule can also be detectably labeled using fluorescence emitting metals such as 152 Eu, or others of the lanthanide series. These metals can be attached to the molecule using such metal chelating groups as diethylenetriaminepentacetic acid (DTPA) or ethylenediaminetetraacetic acid (EDTA). The molecule also can be detectably labeled by coupling it to a chemiluminescent compound. The presence of the chemiluminescent-tagged molecule is then determined by detecting the presence of luminescence that arises during the course of chemical reaction. Examples of particularly useful chemiluminescent labeling compounds are luminol, isoluminol, theromatic acridinium ester, imidazole, acridinium salt and oxalate ester.

A "detection step" may use any of a variety of known methods to detect the presence of nucleic acid (e.g., methylated DNA) or polypeptide. The types of detection methods in which probes can be used include Western blots, Southern blots, dot or slot blots, and Northern blots.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease, e.g., neoplasia, relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a synthetic cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

The term "immobilized" or "attached" refers to a probe (e.g., nucleic acid or protein) and a solid support in which the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule to the support and the non-covalent binding of a biotinylated probe to the molecule. Immobilization may also involve a combination of covalent and non-covalent interactions.

By "marker" is meant any protein or polynucleotide having an alteration in expression level or activity that is associated with a disease or disorder, e.g., neoplasia.

By "modulate" is meant alter (increase or decrease). Such alterations are detected by standard art-known methods such as those described herein.

The term, "normal amount" refers to a normal amount of a complex in an individual known not to be diagnosed with cancer. The amount of the molecule can be measured in a test sample and compared to the "normal control level," utilizing techniques such as reference limits, discrimination limits, or risk defining thresholds to define cutoff points and abnormal values (e.g., for neoplasia). The "normal control level" means the level of one or more proteins (or nucleic acids) or combined protein indices (or combined nucleic acid indices) typically found in a subject known not to be suffering from cancer. Such normal control levels and cutoff points may vary based on whether a molecule is used alone or in a formula combining other proteins into an index. Alternatively, the normal control level can be a database of protein patterns from previously tested subjects who did not convert to cancer over a clinically relevant time horizon. In another aspect, the normal control level can be a level relative to a housekeeping gene.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease in question or is not at risk for the disease.

Relative to a control level, the level that is determined may be an increased level. As used herein, the term "increased" with respect to level (e.g., expression level, biological activity level, etc.) refers to any % increase above a control level. The increased level may be at least or about a 1% increase, at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, or at least or about a 95% increase, relative to a control level.

Relative to a control level, the level that is determined may be a decreased level. As used herein, the term "decreased" with respect to level (e.g., expression level, biological activity level, etc.) refers to any % decrease below a control level. The decreased level may be at least or about a 1% decrease, at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, or at least or about a 95% decrease, relative to a control level.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity, e.g., at least 80%, at least 85%, at least 90%, at least 95%, or at least 99% identity. Polynucleotides having "substantial identity" to an endogenous sequence are typically capable of hybridizing with at least one strand of a double-stranded nucleic acid molecule.

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "neoplasia" is meant a disease or disorder characterized by excess proliferation or reduced apoptosis. Illustrative neoplasms for which the invention can be used include, but are not limited to pancreatic cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

As used herein, "obtaining" as in "obtaining an agent" includes synthesizing, purchasing, or otherwise acquiring the agent.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

The terms "preventing" and "prevention" refer to the administration of an agent or composition to a clinically asymptomatic individual who is at risk of developing, susceptible, or predisposed to a particular adverse condition, disorder, or disease, and thus relates to the prevention of the occurrence of symptoms and/or their underlying cause.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

A "reference sequence" is a defined sequence used as a basis for sequence comparison or a gene expression comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 40 nucleotides, preferably at least about 60 nucleotides, more preferably at least about 75 nucleotides, and even more preferably about 100 nucleotides or about 300 or about 500 nucleotides or any integer thereabout or there between.

The term "sample" as used herein refers to a biological sample obtained for the purpose of evaluation in vitro. Exemplary tissue samples for the methods described herein include tissue samples from neoplasias or circulating exosomes. With regard to the methods disclosed herein, the sample or patient sample preferably may comprise any body fluid or tissue. In some embodiments, the bodily fluid includes, but is not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In some aspects, the sample is a composite panel of at least two of a blood sample, a plasma sample, a serum sample, and a urine sample. In exemplary aspects, the sample comprises blood or a fraction thereof (e.g., plasma, serum, fraction obtained via leukopheresis). Preferred samples are whole blood, serum, plasma, or urine. A sample can also be a partially purified fraction of a tissue or bodily fluid.

A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

A "solid support" describes a strip, a polymer, a bead, or a nanoparticle. The strip may be a nucleic acid-probe (or protein) coated porous or non-porous solid support strip comprising linking a nucleic acid probe to a carrier to prepare a conjugate and immobilizing the conjugate on a porous solid support. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to a binding agent (e.g., an antibody or nucleic acid molecule). Thus, the support configuration may be spherical, as in a bead, or cylindrical, as in the inside surface of a test tube, or the external surface of a rod. Alternatively, the surface may be flat such as a sheet, or test strip, etc. For example, the supports include polystyrene beads. Those skilled in the art will know many other suitable carriers for binding antibody or antigen, or will be able to ascertain the same by use of routine experimentation. In other aspects, the solid support comprises a polymer, to which an agent is chemically bound, immobilized, dispersed, or associated. A polymer support may be a network of polymers, and may be prepared in bead form (e.g., by suspension polymerization). The location of active sites introduced into a polymer support depends on the type of polymer support. For example, in a swollen-gel-bead polymer support the active sites are distributed uniformly throughout the beads, whereas in a macroporous-bead polymer support they are predominantly on the internal surfaces of the macropores. The solid support, e.g., a device contains a binding agent alone or together with a binding agent for at least one, two, three or more other molecules.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, at least 70%, at least 80%, at least 85%, at least 90%, at least 95%, or at least 99% identical at the amino acid level or nucleic acid to the sequence used for comparison.

The term "subject" as used herein includes all members of the animal kingdom prone to suffering from the indicated disorder. In some aspects, the subject is a mammal, and in some aspects, the subject is a human. The methods are also applicable to companion animals such as dogs and cats as well as livestock such as cows, horses, sheep, goats, pigs, and other domesticated and wild animals.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions associated with cancer is within the ability of those in the art. Subjects suffering from, and suspected of suffering from, a specific disease, condition, or syndrome are not necessarily two distinct groups.

As used herein, "susceptible to" or "prone to" or "predisposed to" or "at risk of developing" a specific disease or condition refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

In some cases, a composition of the invention is administered orally or systemically. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule. Parenteral modalities (subcutaneous or intravenous) may be preferable for more acute illness, or for therapy in patients that are unable to tolerate enteral administration due to gastrointestinal intolerance, ileus, or other concomitants of critical illness. Inhaled therapy may be most appropriate for pulmonary vascular diseases (e.g., pulmonary hypertension).

Pharmaceutical compositions may be assembled into kits or pharmaceutical systems for use in arresting cell cycle in rapidly dividing cells, e.g., cancer cells. Kits or pharmaceutical systems according to this aspect of the invention comprise a carrier means, such as a box, carton, tube, having in close confinement therein one or more container means, such as vials, tubes, ampoules, bottles, syringes, or bags. The kits or pharmaceutical systems of the invention may also comprise associated instructions for using the kit.

Any compositions or methods provided herein can be combined with one or more of any of the other compositions and methods provided herein.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A is a graph that displays flow cytometry analysis of the cell cycle profile in T47D cells after prolonged treatment (up to 12 weeks) with 100 nM palbociclib to establish resistance. Once resistant, palbociclib dose was gradually increased from 100 nM (R100) to 500 nM (R500) and cells monitored until resistance was confirmed by cell cycle profile. FIG. 1B is a plot of growth rate of resistant T47D cells compared to parental cells. FIG. 1C is a histogram that displays quantitative real-time PCR analyzing the fold change in mRNA expression between parental and resistant T47D cells (resistant to 100 nM palbociclib). Data are mean±SEM (n=3), * $p<0.05$, *** $p<0.001$. FIG. 1D is a series of bar graphs showing quantitative real-time PCR analyzing the fold change in mRNA expression between parental and resistant T47D cells (resistant up to 100 nM palbociclib). Data are mean±SEM (n=3), * $p<0.05$, *** $p<0.001$. FIG. 1E is an image of western blot analysis of both T47D and MCF7 resistant cells. FIG. 1F is a graph displaying progression-free survival in palbociclib-letrozole and letrozole patient groups.

FIG. 2A is a graph of flow cytometry analyses of the cell cycle profile of knockdown and overexpression of T47D cells (↑CDK4 and ↑CDK6). Data are mean±SEM (n=3). FIG. 2B is an image of western blot analysis of CDK4/6 over expression in parental cells. FIG. 2C is an image of western blot analysis of CDK6 knockdown in resistant T47D cells. FIG. 2D is a graph of cell cycle analysis of resistant T47D cells+/−depletion. Asterisks represent a significant difference between shCDK6 and shNT G1 populations, * $p<0.05$,  $p<0.01$, * $p<0.001$, **** $p<0.0001$. Data are mean±SEM (n=3). FIG. 2E is a series of line graphs of cell cycle analysis of parental, ΔCDK4 and ΔCDK6 T47D cells over a 14-day time period in the present or absence of palbociclib treatment. Data presented as combined percentage of cells in S+G2 phase of the cell cycle (see also, FIG. 11A and FIG. 11B).

FIG. 3A is an image of western blot analysis of shRNA mediated knockdown T47D cells. FIG. 3B is a series of line graphs of clonogenic survival assay after 24 hours palbociclib exposure on shRNA expressing T47D cells. Data are mean±SEM (n=3). FIG. 3C is a line graph of confirmatory CDK6 knockdown and clonogenic survival assay with an additional CDK6 shRNA. Survival was significantly lower in both shCDK6-1 and 2 compared to shNT ($p<0.0001$). Data are mean±SEM (n=3). FIG. 3D is a western blot image and line plot of T47D cells with CRISPR/cas9 knockout of CDK6 using an sgRNA targeting the 5'UTR followed by ectopic expression of CDK6 mutants. Shown is a clonogenic survival assay of CRISPR/cas9 knockout CDK6, and mutant add back lines treated with escalating dose of palbociclib. FIG. 3E is a graph of cell cycle analysis of shCDK6 T47D cells+/−100 nM palbociclib treatment for 24 hours. Data are mean±SEM (n=3), **** $p<0.0001$. FIG. 3F is a histogram showing the results of an annexin V apoptosis assay using shSCR, shCDK6 and sgCDK6 T47D cells treated with escalating doses of palbociclib for 48 hours, n+2.

FIG. 4A is a schematic representation of an assay to test resistance transmission from a resistant cell to non-resistant population. Parental cells were engineered to express GFP and mixed with non-fluorescent parental or resistant cells, and incubated for 48 hours. Cells were then sorted by FACS based on GFP status and the cell cycle of each GFP+ and GFP− populations analyzed. FIG. 4B is a graph of cells cycle analysis of parental GFP+ T47D cells after being cocultured for 48 hours with resistant (100-500 nM) cells. Adjacent bars represent cells which were co-cultured. Palbociclib concentration in the medium was maintained at the level of the resistant cells. FIG. 4C is an image of western blot analysis of CDK6 protein expression. Panel 1—Parental GFP cells were co-cultured with either parental or resistant cells, then FACS sorted by GFP expression. Panel 2—T47D cells were treated with palbociclib for up to 6 days. Panel 3—Parental T47D cells were incubated with conditioned medium from resistant cells, medium contain 100 nM palbociclib and was replaced daily. Panel 4—Exosomes from resistant T47D cell medium were harvested then added to parental cells daily, for a period of 6 days. FIG. 4D is a graph of an excreted cytokines assay performed on conditioned medium from resistant vs parental cell T47D cells. Mean±SD (n=2) cytokine expression.

FIG. 5A-FIG. 5I shows a series of images depicting resistance is conferred to neighboring cells and mediated by exosomal miR-432-5p. FIG. 5A is a graph of hierarchal clustering of 30 miRNAs that display large-magnitude changes that are also statistically significant from miRNA expression profiling of parental, resistant, and parental T47D cells treated for 48 hours with resistant cell medium. FIG. 5B is a table of significantly changed miRNAs grouped by expression in resistant relative to parental cells, sorted by significance. Highlighted miRNAs are significantly predicted to target CDK6 mRNA. FIG. 5C is a graph of exosomes that were harvested from the media of parental and resistant T47D cells. Real-time qPCR was performed to detect each of the miRNAs listed previously, the expression of detectable miRNAs is presented as fold change in resistant vs parental exosomes. FIG. 5D is an image of western blot analysis of CDK6 protein in resistant and parental T47D and MCF7 cells overexpressing selected miRNAs. FIG. 5E is a graph of cell cycle analysis of parental and miR-432-5p overexpressing T47D cells+/−100 nM palbociclib. FIG. 5F is a graph of GFP+ parental T47D cells were co-cultured with either parental, or miR-432-5p overexpressing cells and the cell cycle profile analyzed. FIG. 5G is an image of resistant (R100) cells that were transfected with a miR-432-5p inhibitor then incubated for 48 hours before being analyzed by western blot, to determine CDK6 protein levels, or FIG. 5H is a graph of flow cytometry, to determine the cell cycle distribution. FIG. 5I is a graph of overexpression of miRNAs that was detected by qPCR.

FIG. 6A-FIG. 6H are a series of graphs depicting miR-432-5p expression is significantly higher in a post-CDK4/6 inhibitor treated biopsy, and reduces TGFβ pathway signaling via downregulation of SMAD4. FIG. 6A is a graph of miRNA expression analysis was carried out by real-time qPCR from patient tumor biopsies pre- and post CDK4/6 inhibitor (ribociclib) treatment. miRNAs were ranked based on the fold change in the post treatment biopsy. Data are mean±SEM (n=3), **** $p<0.0001$. FIG. 6B is a graph wherein Mir-432-5p expression was analyzed by miRNAseq in tumor biopsy samples from 44 patients who received CDK4/6 inhibitors. Samples were grouped based on the radiological response. Data is represented as counts per million (CPM). FIG. 6C is a schematic of predicted miRNA (miR-432-5p (SEQ ID NO: 1) binding of SMAD4 (SEQ ID NO: 3) and TGFBR3 (SEQ ID NO: 4) 3'UTR. FIG. 6D is a table of biotin labelled miRNA-432-5p that was used for mRNA pulldown in parental T47D cells, fold enrichment is expressed relative to control RNA and correlated with mRNA expression data (n=3). FIG. 6E is a series of graphs of fold-change in mRNA expression of select genes in resistant cells and the post-CDK4/6 inhibitor treatment biopsy. Data are mean±SEM, n=3. FIG. 6F is an image of a western blot showing protein levels of TGFβ pathway components in parental, resistant, miR-scramble and miR-432-5p expressing cells T47D and MFC7 cells. FIG. 6G is an image showing confirmation of SMAD4 overexpression in resistant T47D cells by western blot. FIG. 6H is a graph of cell cycle analysis of SMAD4 overexpressing, palbociclib resistant T47D cells. Data are mean±SEM (n=3), * $p<0.05$, ** $p<0.01$. Indicated significance is between G1 populations of R100 vs R100+ΔSMAD4.

FIG. 7A is a graph of cell cycle analysis of control, palbociclib treated cells, and cells grown in the absence of drug for up to 7 weeks before being re-challenged with 100 nM for 24 hours (T47D). FIG. 7B is an image of western blot analysis of CDK6 protein expression in T47D and MCF7 cells which have been removed from palbociclib-containing media for up to 7 weeks. FIG. 7C is a graph of gene expression analysis by qPCR of parental, resistant and ex-resistant T47D cells. Ex-resistant cells are resistant cells that have had palbociclib exposure removed for a minimum of 7 weeks. Data are presented as mean±SEM $2^{-\Delta\Delta CT}$ normalized to parental gene expression (n=3), ** $p<0.0001$. FIG. 7D is a bar chart showing miR-432 expression analysis by qPCR in parental, resistant and ex-resistant cells. Data are presented as mean±SEM $2^{-\Delta\Delta CT}$ normalized to parental gene expression (n=3), ** $p<0.0001$. FIG. 7E is a line graph wherein xenografts were established in the presence of palbociclib treatment using palbociclib resistant (R100) MCF7 cells. 100 mg/kg/day palbociclib treatment was maintained until day 36, then removed for 28 days before being re-introduced. Data is RTV of each individual animal as well as the overall average RTV over the course of 90 days. FIG. 7F is a bar chart showing gene expression analysis by qPCR in tumors taken from mice at day 36 and day 64. Data are presented as mean±SEM $2^{-\Delta\Delta CT}$ normalized to day 36 tumor gene expression (n≥3), * $p<0.05$, ** $p<0.01$.

FIG. 8A is a bar graph showing a graph of flow cytometry analysis of the cell cycle profile of palbociclib resistant MCF7 cells. Cells were initially made resistant to 100 nM (R100) which was then escalated culminating in cells resistant to 500 nM (R500). FIG. 8B is a graph of the growth rate of resistant cells compared to parental cells. FIG. 8C is a bar graph showing flow cytometry analysis of the cell cycle profile of parental and resistant ZR-75-1, SKBR3 and BT-20 cells. FIG. 8D is a bar graph showing quantitative real-time qPCR analysis of CDK6 expression in parental and resistant ZR-75-1, SKBR3 and BT-20 cells. FIG. 8E is a bar graph showing quantitative real-time qPCR analysis of miR-432 expression in parental and resistant ZR-75-1, SKBR3 and BT-20 cells. FIG. 8F is a graph showing the growth rate of ZR-75-1, SKBR3 and BT-20 cells cultured to palbociclib resistance.

FIG. 10A (T47D cells) and FIG. 10B (MCF7 cells) were treated with either DMSO, palbociclib, ribociclib or abemaciclib for 5 days. Subsequently, cell growth was quantified and normalized to DMSO treated control. Cells were either parental, palbociclib resistant (100 nM), CDK6 overexpressing, miR-432-5p overexpressing, ex-resistant or CDK6 knockdown. Data are mean±SEM (n>3), * $p<0.05$,  $p<0.01$, * $p<0.001$, **** $p<0.0001$.

FIG. 11A is a bar graph, wherein cells were treated with either DMSO, 10 μM GW4869 or 10 μM manumycin A for 72 hours prior to exosome harvest and quantification. FIG. 11B is a bar graph, wherein palbociclib resistant GFP− cells were cocultured with GFP parental cells in the presence of either DMSO, GW4869, manymycin A or miR-432-5p inhibitor for 72 hours. Subsequently, cells were harvested and analyzed by flow cytometry for GFP expression and cell cycle profile.

FIG. 12A (T47D parental cells) and FIG. 12B (T47D resistant cells) are graphs, wherein cells were treated with either DMSO, palbociclib or galunisertib for 5 days. Subsequently, cell growth was quantified and normalized to DMSO treated control. BLISS Synergy/antagonism score was modeled using Combenefit software. FIG. 12C is a graph, wherein T47D parental and resistant cells were treated with escalating dose of galunisertib for 5 days. Subsequently, cell growth was quantified and normalized to DMSO treated control. FIG. 12D is a bar graph showing cell cycle analysis of T47D cells treated with galunisertib and/or palbociclib for 24 hours.

DETAILED DESCRIPTION OF THE INVENTION

Figure 1A:
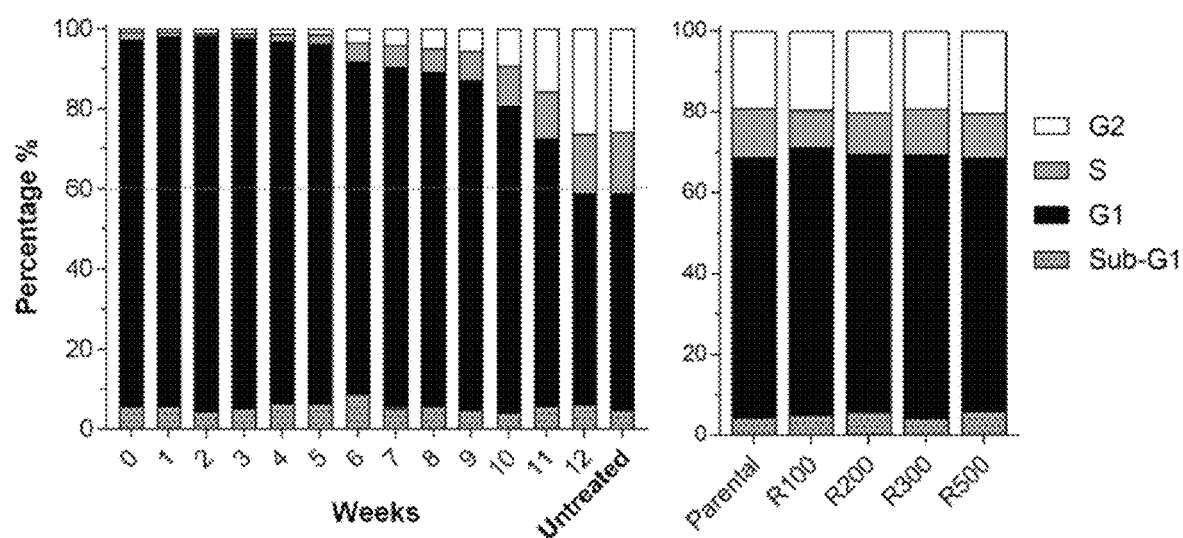
FIG. 1A-FIG. 1F show a series of graphs that display generated CDK4/6 inhibitor resistant cell lines have dramatically increased CDK6 protein expression.

The invention is based, at least in part, upon the identification of increased CDK6 expression as a key determinant of acquired resistance after exposure to palbociclib in estrogen receptor (ER)-positive breast cancer cells, reversible after removal of drug for prolonged periods. Increased CDK6 in resistant cells is dependent on TGF-β pathway suppression via miR-432-5p expression. Exosomal miR-432-5p expression mediates transfer of the resistance phenotype between neighboring cell populations, causing previously sensitive cells to acquire CDK4/6 inhibitor resistance. As described in detail below, among patients with advanced breast cancer disease, both palbociclib and ribociclib have demonstrated increased progression-free survival in combination with hormonal therapy, leading to approvals of both palbociclib and ribociclib in this disease. The success of these agents now highlights the critical importance of understanding mechanisms of acquired resistance in order to ultimately develop follow-up treatment strategies.

Described herein is a mechanism of exosomal-mediated drug resistance. As described in detail below, an acquired drug resistance phenotype is transmitted from one population of cells to another via exosomal-miRNA signaling. Prior to the invention described herein, there were no examples demonstrating the transfer of an acquired resistance phenotype via this mechanism.

Specifically, the results presented herein demonstrate a mechanism of acquired kinase inhibitor resistance that is independent of inherent genetic mutations, does not involve clonal selection, is reversible in vivo, and can be conferred through exosomal-miRNA signaling. This miRNA-mediated mechanism resulted in the transfer of resistance to CDK4/6 inhibition among estrogen receptor-positive breast cancer cell populations and was reversible after drug withdrawal. The findings presented herein were confirmed in paired patient biopsies obtained pre- and post CDK4/6 inhibitor treatment, and ultimately impact clinical management of disease. Specifically, the findings presented herein have implications for the assessment of paired treatment tumor or liquid biopsies in efforts to understand CDK4/6 inhibitor resistance. Highlights of the results presented herein include that CDK4/6 inhibitor resistance is mediated by increased CDK6 expression; CDK6 resistance is reversible by prolonged drug removal; CDK6 resistance is conferred between cell populations via extracellular signaling; increased exosomal miR-432-5p suppresses the TGF-β pathway, thereby increasing CDK6 levels; and resistance is reversible by prolonged drug removal in vivo.

Through the generation of CDK4/6 inhibitor resistant cell lines, a resistance mechanism by which increased expression and exosomal excretion of miR-432-5p caused TGFβ pathway repression was characterized, and an increase in CDK6 expression driving cell cycle progression. As described in detail below, analysis of pre-treatment and post-progression biopsies from a patient with parotid cancer harboring CDKN2A/B loss, who had achieved a partial response to the CDK4/6 inhibitor ribociclib, demonstrates that the CDK4/6 inhibitor resistance mechanism is clinically relevant. This analysis confirmed overexpression of miR-432, decreased TGFβ signaling (via decreased SMAD4), and increased CDK6 in the post-progression biopsy, demonstrating the clinical relevance of this acquired resistance mechanism.

Prior to the invention described herein, there was only limited study of resistance mechanisms to CDK4/6 inhibitors. Loss of expression of the retinoblastoma (Rb) protein, CCNE1 amplification (Herrera-Abreu, M. T. et al., Cancer Res 76: 2301-2313 (2016)), CDK6 amplification (Yang, C. et al., Oncogene 36: 2255-2264 (2016)), and increased PDK1 expression (Jansen, V. M., et al., Cancer Res. 77: 2488-2499 (2017)) have been reported. Describe in detail below are the first results demonstrating a mechanism by which resistance is reversible and transmitted.

As an increasing number of patients receiving CDK4/6 inhibitors are undergoing biopsy at progression to determine mechanisms of resistance, rapid dissemination of this mechanism is increasingly important as an additional assessments of patients' tumors. Ultimately, acquisition of resistance in this manner may be followed by serial analysis of plasma exosomes from treated patients, which may precede true radiologic progression and which may affect patient management. Furthermore, since data presented herein demonstrate the reversibility of this mechanism of resistance, these results have clinical implications for the re-use of a CDK4/6 inhibitors after an appropriate drug holiday. Based on the wide-ranging use of CDK4/6 inhibitors in breast cancer, with other cancers to follow, the results presented herein are important to the field of drug resistance. As described in detail herein, increased expression and secretion of miR-432-5p, decreased SMAD4 protein expression, decreased TGF-β pathway signaling, and increased CDK6 protein are associated with CDK4/6 inhibitor resistance.

Breast Cancer

Breast cancer develops from cells within the inner lining of milk ducts and cells from breast lobules. Signs of breast cancer include a lump in the breast, a change in breast shape, or dimpling of the skin. Outcomes for breast cancer depend on a variety of factors including cancer type, extent of disease, and a person's age. Worldwide, breast cancer is the primary type of cancer in women, accounting for 25% of all cases.

Most breast cancers are easily diagnosed by microscopic analysis of a sample or biopsy of the affected breast area. In those who have been diagnosed with cancer, a number of treatments may be used, including surgery, radiation therapy, chemotherapy, hormonal therapy and targeted therapy. Hormonal therapy is based on the presence of three important cellular receptors in breast cancer, estrogen receptor (ER), progesterone receptor (PR), and human epidermal receptor protein-2 (HER2). Estrogen receptor positive (ER+) cancer cells depend on estrogen for their growth and are commonly treated with selective estrogen receptor modulators (SERMs) such as raloxifene (Evista), tamoxifen (Nolvadex), and toremifene (Fareston). Typically, tamoxifen is a first-line hormonal treatment of ER-positive metastatic breast cancer. HER2 determination is important in the treatment of patients diagnosed with invasive breast carcinoma. Untreated, HER2+ breast cancers are more aggressive than HER2− breast cancers. However, HER2+ cancer cells respond to drugs such as the monoclonal antibody trastuzumab (in combination with conventional chemotherapy). Cells that do not have any estrogen receptors, progesterone receptors, or HER2 are termed triple-negative. Triple-negative cells frequently express receptors for other hormones, such as androgen receptor and prolactin receptor.

CDK4/6-Cyclin D-Retinoblastoma (RB) Pathway

Disruption of cell cycle pathways is a common mechanism in tumor formation. In particular, CDKs are a driving force in cancer. The CDK4/6-cyclin D-RB pathway is estimated to be modified in ~80% of all cancers. CCND1 amplification has also been observed in a variety of cancers, including breast cancer. Up-regulation of cyclin D causes increased cyclin D-CDK4/6 activity promoting cell cycle progression. Moreover, Cyclin D-dependent kinase activity is a driving factor for ER+ breast carcinogenesis, irrespective of CCND1 amplification, making CDK4/6 inhibition a promising approach to restore cell cycle regulation and for this breast cancer subset. However, as with all cancer treatments, prior to the invention described herein, resistance was a major issue limiting the efficacy of this approach. Accordingly, understanding mechanisms or resistance to CDK4/6 inhibition is a pressing clinical issue.

Palbociclib

Multiple potent and highly selective inhibitors of the cell cycle kinases CDK4 and CDK6 are in development. One such inhibitor, palbociclib (PD-0332991), was recently approved for use in combination with letrozole for the treatment of estrogen receptor positive (ER+) and human epidermal growth factor receptor 2 (HER2) negative breast cancer. The molecular formula for palbociclib is $C_{24}H_{29}N_7O_2$ and the chemical structure for palbociclib is represented below.

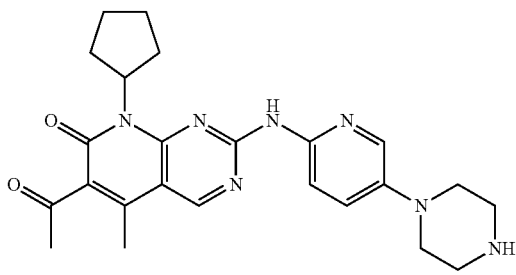 [SMILES: CC(=O)c1c(C)c2cnc(Nc3ccc(N4CCNCC4)cn3)nc2n(C2CCCC2)c1=O]

Palbociclib targets and half maximal inhibitory concentration (IC50) values for those targets are CDK4 (11 nM), CDK6 (15 nM), CDK2/CyclinE2 (>10 μM), CDK2/CyclinA (>10 μM), CDK1/CyclinB (>10 μM), CDK5/p25 (>10 μM), respectively. Previous results have shown that the addition of palbociclib to letrozole treatment extends progression free survival 24.8 months in the palbociclib-letrozole group and 14.5 months on letrozole only group. Prior to the invention described herein, mechanisms of palbociclib resistance were not extensively investigated.

Gene Expression Profiling

In general, methods of gene expression profiling can be divided into two large groups: methods based on hybridization analysis of polynucleotides, and methods based on sequencing of polynucleotides. Methods known in the art for the quantification of messenger RNA (mRNA) expression in a sample include northern blotting and in situ hybridization, Ribonuclease (RNAse) protection assays, RNA Sequencing (RNA-seq), and reverse transcription polymerase chain reaction (RT-PCR). Alternatively, antibodies are employed that recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). For example, RT-PCR is used to compare mRNA levels in different sample populations, in normal and tumor tissues, with or without drug treatment, to characterize patterns of gene expression, to discriminate between closely related mRNAs, and/or to analyze RNA structure.

In some cases, a first step in gene expression profiling by RT-PCR is the reverse transcription of the RNA template into complementary DNA (cDNA), followed by amplification in a PCR reaction. For example, extracted RNA is reverse-transcribed using a GeneAmp RNA PCR kit (Perkin Elmer, Calif., USA), following the manufacturer's instructions. The cDNA is then used as template in a subsequent PCR amplification and quantitative analysis using, for example, a TaqMan® (Life Technologies, Inc., Grand Island, N.Y.) assay.

Microarrays

Differential gene expression can also be identified, or confirmed using a microarray technique. In these methods, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines and corresponding normal tissues or cell lines. Thus, RNA is isolated from a variety of primary tumors or tumor cell lines. If the source of mRNA is a primary tumor, mRNA is extracted from frozen or archived tissue samples.

In the microarray technique, PCR-amplified inserts of cDNA clones are applied to a substrate in a dense array. The microarrayed genes, immobilized on the microchip, are suitable for hybridization under stringent conditions.

In some cases, fluorescently labeled cDNA probes are generated through incorporation of fluorescent nucleotides by reverse transcription of RNA extracted from tissues of interest. Labeled cDNA probes applied to the chip hybridize with specificity to loci of DNA on the array. After washing to remove non-specifically bound probes, the chip is scanned by confocal laser microscopy or by another detection method, such as a charge-coupled device (CCD) camera. Quantification of hybridization of each arrayed element allows for assessment of corresponding mRNA abundance.

In some configurations, dual color fluorescence is used. With dual color fluorescence, separately labeled cDNA probes generated from two sources of RNA are hybridized pairwise to the array. The relative abundance of the transcripts from the two sources corresponding to each specified gene is thus determined simultaneously. In various configurations, the miniaturized scale of the hybridization can afford a convenient and rapid evaluation of the expression pattern for large numbers of genes. In various configurations, such methods can have sensitivity required to detect rare transcripts, which are expressed at fewer than 1000, fewer than 100, or fewer than 10 copies per cell. In various configurations, such methods can detect at least approximately two-fold differences in expression levels (Schena et al., Proc. Natl. Acad. Sci. USA 93(2): 106-149 (1996)). In various configurations, microarray analysis is performed by commercially available equipment, following manufacturer's protocols, such as by using the Affymetrix GenChip technology, or Incyte's microarray technology.

RNA-Seq

RNA sequencing (RNA-seq), also called whole transcriptome shotgun sequencing (WTSS), uses next-generation sequencing (NGS) to reveal the presence and quantity of RNA in a biological sample at a given moment in time.

RNA-Seq is used to analyze the continually changing cellular transcriptome. See, e.g., Wang et al., Nat. Rev. Genet. 10(1): 57-63 (2009), incorporated herein by reference. Specifically, RNA-Seq facilitates the ability to look at alternative gene spliced transcripts, post-transcriptional modifications, gene fusion, mutations/SNPs and changes in gene expression. In addition to mRNA transcripts, RNA-Seq can look at different populations of RNA to include total RNA, small RNA, such as miRNA, tRNA, and ribosomal profiling. RNA-Seq can also be used to determine exon/intron boundaries and verify or amend previously annotated 5' and 3' gene boundaries.

Prior to RNA-Seq, gene expression experiments were done with hybridization-based microarrays. Issues with microarrays include cross-hybridization artifacts, poor quantification of lowly and highly expressed genes, and needing to know the sequence of interest. Because of these technical issues, transcriptomics transitioned to sequencing-based methods. These progressed from Sanger sequencing of Expressed Sequence Tag libraries, to chemical tag-based methods (e.g., serial analysis of gene expression), and finally to the current technology, NGS of cDNA (notably RNA-Seq).

MicroRNA-Mediated Suppression of the TGF-β Pathway Confers Transmissible and Reversible CDK4/6 Inhibitor Resistance.

As mentioned above, cyclin D-dependent kinase activity is a driving factor for carcinogenesis in more than 80% of hormone receptor-positive breast cancers (Massague, 2004). Additionally, CCND1 amplification or overexpression portends poor survival, making inhibition of the cell cycle kinases CDK4 and CDK6 a promising approach for this breast cancer subset (Arnold, A., et al., J Clin. Oncol. 23: 4215-4224 (2005); Elsheikh, S. et al., Breast Cancer Res. Treat. 109: 325-335 (2008); Perou, C. M. et al., Nature 406: 747-752 (2000); Roy, P. G. et al., Int. J. Cancer 127: 355-360 (2010); The Cancer Genome Atlas Network, Nature 490: 61-70 (2012); Velasco-Velazquez, M. A. et al, Future Oncol. 7: 753-765 (2011)). Multiple potent and highly selective inhibitors of CDK4/6 are in development. For example, palbociclib was recently approved for use in combination with letrozole or fulvestrant for the treatment of metastatic estrogen receptor-positive (ER+), HER2-negative breast cancer based on prolonged progression-free survival with combination treatment compared to hormonal therapy alone (Cristofanilli, M. et al., The Lancet Oncol. 17: 425-439 (2016); Finn, R. S. et al., N. Engl. J. Med. 375: 1925-1936 (2016); Turner, N. C. et al., New Engl. J. Med. 373: 209-219 (2015)). Similar data have been reported for ribociclib (Hortobagyi, G. N. at al., N. Engl. J. Med. 375: 1738-1748 (2016)) and abemacyclib (Goetz, M. P. et al., J. Clin. Oncol. 35: 3638-3646 (2017); Sledge, G. W. et. al., J. Clin. Oncol. 35: 2875-2884 (2017)). Additionally, the CDK4/6 inhibitor, abemaciclib, has been approved as monotherapy for patients with advanced ER+ breast cancer who have progressed on prior endocrine therapy and chemotherapy (Patnaik, A. et al., Cancer Discov. 6: 740-753 (2016); Dickler, M. N. et al., Clin. Cancer Res. 23: 5218-5224 (2017)). CDK4/6 inhibition may also have activity in HER2-driven breast cancer, as well as in triple-negative breast cancers that retain expression of the retinoblastoma (RB) protein (Roberts, P. J. et al., J. Natl. Cancer Inst. 104: 476-487 (2012); Yu, Q. et al., Cancer Cell 9: 23-32 (2006)).

Prior to the invention described herein, CDK4/6 inhibitor-based treatment was complicated by the development of acquired resistance. In leukemia models, reduced p27Kip1 expression and elevated CDK2 activity can overcome palbociclib-mediated G1 arrest (Wang, L. et al., Blood 110: 2075-2083 (2007)). In breast cancer models, RB loss, amplification of CCNE1 (Herrera-Abreu, M. T. et al., Cancer Res 76: 2301-2313 (2016)), CDK6 (Yang, C. et al., Oncogene 36: 2255-2264 (2016)), or FGFR1 (Formisano et al., 2017; SABCS, abstract) and increased PDK1 activity (Jansen, V. M., et al., Cancer Res. 77: 2488-2499 (2017)) are also mechanisms by which the cancer cell can bypass CDK4/6 inhibitor mediated G1 arrest. In analysis of tumor or liquid biopsies from breast cancer patients treated with CDK4/6 inhibitors, high cyclin E expression may define populations with intrinsic resistance (Turner et al., 2018; AACR, abstract), while acquired RB1 mutation and FGFR pathway activation have been identified in post-progression samples (Condorelli, R. et al., Ann Oncol 29: 640-645 (2018); Turner et al., 2018; ASCO, abstract; Formisano et al., 2017; SABCS, abstract).

Described in detail below is a mechanism by which resistance to CDK4/6 inhibitor treatment arises, can be reversed, and is transmitted via extracellular signaling and can be reversed. Acquired resistance is centered on increased CDK6 protein concentration as the key determinant, achieved via suppression of the TGF-β pathway, which is mediated by exosomal transfer of microRNA (miRNA), e.g., miR-432-5p.

Inhibition of CDK4/6 is utilized as treatment for ER+ breast cancer. Described herein are mechanisms of intrinsic and acquired resistance. Here, through the generation of cell lines with acquired palbociclib resistance, CDK6 is highlighted as a key protein mediating cell cycle progression in the presence of the inhibitor.

Interestingly, CDK6 not only governs resistance, but also the initial response to CDK4/6 inhibition. As described in detail below, shRNA-mediated depletion of the small amount of CDK6 in parental cells converted the response to palbociclib from cytostatic to cytotoxic. Furthermore, CDK6 kinase activity was required for cell survival in the presence of CDK4/6 inhibition. Despite palbociclib having almost equal potency against CDK4 and CDK6, with $IC_{50}$'s of 11 nM and 16 nM, respectively (Fry, D. W. et al., Mol. Cancer. Ther. 3: 1427-1438 (2004)), there was no effect on survival after treatment when CDK4 was depleted from parental cells. Similarly, depletion of the D-cyclins had no effect on survival after palbociclib treatment. Hence, the low level of CDK6 activity in parental cells is required for survival in response to palbociclib, and when enhanced in expression, caused resistance to cell cycle arrest and reduced growth inhibition. The resistance phenotype required the presence of an active kinase domain. Described herein is an evaluation of whether CDK6 activity in ER-positive breast cancer cells is a general "survival factor" protecting from other stressors, such as disruption of the hormonal axis or DNA damage.

As described in detail below, during the generation of resistant cells, a clonally expanding population was not observed. This is in direct contrast to current models of kinase inhibitor resistance in which a subpopulation of cells harboring an inherent mutation emerges under selective pressure. With continuous exposure to palbociclib, it was observed that the entire population of cells remained in the G1 phase of the cell cycle without an increase in cell death, followed by cells gradually cycling in unison. This suggested that resistance was not reliant on an inherent genetic alteration present in low allelic burden, but rather a feedback loop involving some degree of extracellular signaling that drives the necessary CDK6 expression.

This hypothesis was further supported by the reversibility of resistance. As described in detail below, the removal of drug from the medium for a prolonged time period resulted in reduced CDK6 gene and protein expression, and restored susceptibility of cells to palbociclib-mediated G1 arrest. This could not occur had resistance arisen due to a permanent genetic event. While the expression of many cell cycle genes returns to similar levels as in parental cells, hierarchical clustering of gene expression analysis data showed ex-resistant cells to be more closely related to resistant cells than parental cells. This phenomenon was further confirmed in vivo by demonstrating that a treatment holiday of 28 days was sufficient to re-sensitize palbociclib-resistant tumors. Remarkably, as described in detail below, substantial regression of all but 1 tumor was observed, indicating a phenotypic change can occur by removal of CDK4/6 inhibition and that treatment holidays are a useful clinical strategy. It is also determined whether cells return to a state indistinguishable from parental cells on a genetic level. It is also determined whether these changes can be exploited to gain a therapeutic advantage. In the case of mantle cell lymphoma cells, the altered gene expression pattern of cells released from an acute palbociclib-mediated G1 arrest created acquired vulnerabilities, including susceptibility to signal transduction inhibitors (Chiron, D. et al., Cell Cycle 12: 1892-1900 (2013); Di Liberto, M. et al., Blood 128: 610-610 (2016)).

As described in the examples below, to elucidate the role of extracellular signaling in CDK4/6 inhibitor resistance, parental and resistant cells were co-cultured. After 48 hours of co-culture, parental cells no longer arrested to CDK4/6 inhibition and displayed a marked increase in CDK6 protein expression, which was comparable to that of the drug exposure-generated resistant lines. The acquisition of resistance with only 48 hours of co-culture was in stark contrast to the 12-week period of continuous drug exposure required to initially derive the resistant lines. Although 48 hours was sufficient to "transmit" resistance to 100-200 nM palbociclib, it was not sufficient for the development of resistance to 500 nM palbociclib, most likely due to the requirement for a greater increase in CDK6 expression to circumvent resistance to the higher drug concentration.

It was also demonstrated herein that the acquisition of resistance was dependent on exosomes, since inhibition of exosome biogenesis reduced the transmission of resistance. Additionally, resistance did not appear to be cytokine regulated. This led to an investigation of miRNAs, as recent publications have identified exosomal miRNA signaling as a biomarker and key pathway regulator (Choi, Y. E. et al., eLife 3: e02445 (2014); Hannafon, B. N. et al., Breast Cancer Res. 18: 90 (2016); Kosaka, N. et al., J Biol. Chem. 285: 17442-17452 (2010); Mittelbrunn, M. et al., Nat Commun. 2: 282 (2011); Montecalvo, A. et al., Blood 119: 756-766 (2012); Rabinowits, G. et al., Clinical Lung Cancer 10: 42-46 (2009)). The expression of numerous miRNAs was significantly different between parental and resistant cells. Interestingly, the miRNA profile of resistant cells was more closely related to that of cells cultured in resistant cell medium for 48 hours than it was to parental cells, highlighting the importance of extracellular miRNA signaling in regulating both mRNA and miRNA expression. Of the 20 most significantly increased miRNAs in resistant cells, only two were predicted to target CDK6, as opposed to eight of the decreased miRNAs.

Although investigating the downregulated miRNAs predicted to target CDK6 are of interest, it is unlikely that these miRNAs are related to the mechanism of transmitted resistance. Instead, as described in detail below, it was identified that overexpression of miR-432-5p (one of the significantly upregulated miRNAs in resistant cells) caused a marked increase in CDK6 protein level in parental cells, conferred CDK4/6 inhibitor resistance, and transmitted resistance to co-cultured cells. Therefore, miR-432-5p-overexpressing cells phenocopied resistant lines generated after several weeks of continuous drug exposure.

To validate the importance of miR-432-5p expression clinically, 44 biopsy samples from metastatic breast cancer patients treated with CDK4/6 inhibitors were utilized. A higher level of miR-432-5p expression was identified in tumor biopsies from patients with intrinsic or acquired CDK4/6 inhibitor resistance, compared to those from patients with sensitive disease. Although differences in miR-432-5p expression between the resistant and sensitive populations only trended toward significance, the small sample size and variable timing of post-progression biopsies could have affected results from patients with acquired resistance. Ideally, paired pre- and post-progression biopsies would rigorously show increased miRNA expression as a determinant of acquired resistance. Importantly, paired samples from one patient whose tumor had responded to ribociclib were assayed, and a highly significant increase in miR-432-5p in the post-progression biopsy was identified. These results further support the occurrence of this mechanism of resistance in primary patient samples. Of note, resistant samples in which RB1 loss has been documented did not demonstrate high levels of miR-432-5p. Additional studies determine if high miR-432-5p expression may occur along with other alterations conferring resistance, or whether this mechanism is mutually exclusive with other such alterations.

These data presented herein demonstrate the mechanism of resistance, and extracellular signaling which gives rise to resistance, is increased miR-432-5p expression and excretion, which in turn drives increased CDK6 protein expression. Importantly, a significant increase in miR-432-5p in the post-progression biopsy of a CDK4/6 inhibitor-treated patient was identified, demonstrating that this mechanism of resistance may occur in primary patient samples.

To determine the target of miR-432-5p, a biotin-labeled miRNA:mRNA pulldown was performed, leading to the discovery that the TGF-β pathway was a significantly enriched target. Many mRNAs of the TGF-β pathway were significantly enriched. As a result, these data were correlated with gene expression data. As miRNAs lead to increased degradation of mRNA (Valencia-Sanchez, M. A. et al., Genes Dev. 20: 515-524 (2006)), genes that were both significantly enriched by miRNA pulldown, and downregulated in resistant cells were assessed, which lead to SMAD4 and TGFBR3. TGFBR3, however, was only decreased in T47D cells, and not in MCF7 cells or the post-progression biopsy. Only SMAD4 mRNA expression was significantly lower in both resistant T47D and MCF7 cells, as well as in the post-progression biopsy. To this end, overexpression of SMAD4 reduced CDK6 expression, as previously reported (Tsubari, M. et al., Mol. Cell Biol. 19: 3654-3663 (1999); Zhang, F., et al., Oncogene 20: 5888-5896 (2001)), and reversed CDK4/6 inhibitor resistance.

These results suggested that TGF-β pathway inhibition would be antagonistic with CDK4/6 inhibition in T47D and MCF7 cells. This was confirmed in combinatorial experiments in T47D cells using a TGF-βR1 inhibitor with palbociclib. Interestingly, previous work in pancreatic cancer cell lines indicated that palbociclib can induce TGF-β pathway-mediated epithelial-mesenchymal transition (EMT) that is prevented by TGF-βR1 inhibition, so that combined CDK4/6 and TGF-βR1 inhibition may be beneficial (Liu, F. et al., Mol. Cancer Ther. 11: 2138-2148 (2012)). Notably, evidence of palbociclib-induced EMT in the breast cancer cell lines was not observed. Taken together, these results demonstrate the complexity of the TGF-β pathway and its interface with CDK4/6 inhibition, which may be context dependent.

Accordingly, resistance to CDK4/6 inhibitors is driven by increased expression of CDK6. CDK6 resistance can be reversed, prolonged removal of drug causes CDK6 levels to decline, and cells become re-sensitized to palbociclib mediated G1 arrest. CDK6 resistance is not mediated via permanent genetic event. CDK4/6 inhibitor resistance is mediated via extracellular signaling, specifically exosomes. Overexpression of miR-432-5p infers CDK4/6 inhibitor-resistance phenotype and exosomal miR-432-5p confers resistance to neighboring cells. miR-432-5p targets SMAD4, causing decreased TGF-β signaling, and increased CDK6 protein. miR-432-5p is highly expressed in a post-progression biopsy from a patient treated with CDK4/6 inhibition.

In summary, the data presented here demonstrate a clinically relevant mechanism of CDK4/6 inhibitor resistance whereby increased exosomal expression of miR-432-5p causes a downregulation of TGF-β pathway signaling, via SMAD4 knockdown, which in turn results in an increase in CDK6 expression allowing cells to overcome G1 arrest. While multiple studies have focused on the regulatory properties of exosomal miRNA, the data presented here represent the first mechanism of acquired drug resistance that is wholly dependent on excreted miRNA, and that can be reversed by miRNA-inhibition.

As this resistance is reversible, re-challenge with a CDK4/6 inhibitor proves beneficial after an adequate drug holiday, i.e., the CDK4/6 inhibitor is not administered to the patient for a period of time. Additionally, as resistance is mediated by exosomal signaling, analysis of patient plasma exosomes identifies emerging resistance prior to radiological progression, and favorably affects patient management.

World Health Organization Criteria

The WHO Criteria for evaluating the effectiveness of anti-cancer agents on tumor shrinkage, developed in the 1970s by the International Union Against Cancer and the World Health Organization, represented the first generally agreed specific criteria for the codification of tumor response evaluation. These criteria were first published in 1981 (Miller et al., Clin. Cancer Res. 47(1): 207-14 (1981), incorporated herein by reference). WHO Criteria proposed >50% tumour shrinkage for a Partial Response and >25% tumour increase for Progressive Disease.

Response Evaluation Criteria in Solid Tumors (RECIST)

RECIST is a set of published rules that define when tumors in cancer patients improve ("respond"), stay the same ("stabilize"), or worsen ("progress") during treatment (Eisenhauer et al., European Journal of Cancer 45: 228-247 (2009), incorporated herein by reference). Only patients with measureable disease at baseline should be included in protocols where objective tumor response is the primary endpoint.

The response criteria for evaluation of target lesions are as follows:

Complete Response (CR): Disappearance of all target lesions.

Partial Response (PR): At least a 30% decrease in the sum of the longest diameter (LD) of target lesions, taking as reference the baseline sum LD.

Stable Disease (SD): Neither sufficient shrinkage to qualify for PR nor sufficient increase to qualify for PD, taking as reference the smallest sum LD since the treatment started.

Progressive Disease (PD): At least a 20% increase in the sum of the LD of target lesions, taking as reference the smallest sum LD recorded since the treatment started or the appearance of one or more new lesions.

The response criteria for evaluation of non-target lesions are as follows:

Complete Response (CR): Disappearance of all non-target lesions and normalization of tumor marker level.

Incomplete Response/Stable Disease (SD): Persistence of one or more non-target lesion(s) or/and maintenance of tumor marker level above the normal limits.

Progressive Disease (PD): Appearance of one or more new lesions and/or unequivocal progression of existing non-target lesions.

The response criteria for evaluation of best overall response are as follows. The best overall response is the best response recorded from the start of the treatment until disease progression/recurrence (taking as reference for PD the smallest measurements recorded since the treatment started). In general, the patient's best response assignment will depend on the achievement of both measurement and confirmation criteria.

Patients with a global deterioration of health status requiring discontinuation of treatment without objective evidence of disease progression at that time should be classified as having "symptomatic deterioration". Every effort should be made to document the objective progression even after discontinuation of treatment.

In some circumstances, it may be difficult to distinguish residual disease from normal tissue. When the evaluation of complete response depends on this determination, it is recommended that the residual lesion be investigated (fine needle aspirate/biopsy) to confirm the complete response status.

Pharmaceutical Therapeutics

For therapeutic uses, the compositions or agents described herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia, i.e., the melanoma. Generally, amounts will be in the range of those used for other agents used in the treatment of other diseases associated with neoplasia, although in certain instances lower amounts will be needed because of the increased specificity of the compound. For example, a therapeutic compound is administered at a dosage that is cytotoxic to a neoplastic cell.

Formulation of Pharmaceutical Compositions

The administration of a compound or a combination of compounds for the treatment of a neoplasia may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other cases, this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other aspects, it is envisaged that doses may be in the range of about 5 mg compound/Kg body to about 20 mg compound/Kg body. In other embodiments, the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol.

Kits or Pharmaceutical Systems

The present compositions may be assembled into kits or pharmaceutical systems for use in ameliorating a neoplasia. Kits or pharmaceutical systems according to this aspect of the invention comprise a carrier means, such as a box, carton, tube or the like, having in close confinement therein one or more container means, such as vials, tubes, ampoules, or bottles. The kits or pharmaceutical systems of the invention may also comprise associated instructions for using the agents of the invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

CDK4/6 inhibition is now part of the standard armamentarium for patients with estrogen receptor (ER)-positive breast cancer, so that defining mechanisms of resistance is a pressing issue. As described in the examples below, it was identified that increased CDK6 expression as a key determinant of acquired resistance after exposure to palbociclib in ER-positive breast cancer cells, reversible after removal of drug for prolonged periods. Increased CDK6 in resistant cells was dependent on TGF-β pathway suppression via miR-432-5p expression. As described in detail below, exosomal miR-432-5p expression mediated transfer of the resistance phenotype between neighboring cell populations, causing previously sensitive cells to acquire CDK4/6 inhibitor resistance. These data were confirmed in pre-treatment and postprogression biopsies from a parotid cancer patient who had responded to ribociclib, demonstrating that this resistance mechanism is clinically relevant. Additionally, as described herein, the CDK4/6 inhibitor resistance phenotype can be reversed in vitro and in vivo by a prolonged drug holiday.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Materials and Methods

The following materials and methods were utilized in generating the results presented herein.
Cell Lines and Culture
T47D and MCF7 cells (ATCC) were maintained as monolayers in Dulbecco's modified Eagles medium supplemented with 10% fetal bovine serum, 2 mM L-glutamine, 2 mM penicillium:streptomycin solution and 0.2 Units/ml bovine insulin. Cells were maintained at 37° C., 5% $CO_2$, in a humidified incubator. Cells were free of Mycoplasma contamination (MycoAlert Assay, Lonza).

Compounds
Palbociclib was provided by Pfizer, Inc.
Flow Cytometry
For cell cycle analysis, cells were fixed with 70% ethanol on ice, washed with PBS, stained with propidium iodide (BD Bioscience) and analyzed using a LSR Fortessa flow cytometer (BD Bioscience). Annexin V apoptosis assays were performed and analyzed in accordance with manufacturer's instructions (BD Bioscience). For transferable resistance assays, parental cells expression the GFP protein in the pLEX-307 backbone were mixed 1:1 with none-fluorescent cells. Cells were sorted based on GFP status for subsequent cell cycle analysis or western blot.
Western Blotting
Cells were lysed with RIPA buffer (10 mM Tris, pH 7.5, 1% Nonidet-P40, 2 mM Na2EDTA, 150 mM NaCl) plus protease inhibitors (Calbiochem) and protein estimation was performed by Pierce assay. Gel electrophoresis was performed with Bis-Tris 4-12% (v/v) polyacrylamide gradient gels (ThermoFisher). Samples were transferred onto Immobilin-P PVDF membrane (EMD Millipore), and probed with primary antibodies against either CDK1, CDK2, CDK4, CDK6, Cyclin D1, Cyclin D3, Cyclin E, p27, SMAD3, SMAD4, TGFβ, TGFβR3 (Santa Cruz), pRB (Cell signaling) or actin (Genescript). Goat anti-rabbit or goat anti-mouse HRP-linked secondary antibodies (1:1000; Dako) and ECL reagent (Perkin Elmer) were used for protein detection. Cytokines were analyzed using the Human Cytokine Array Kit performed per manufactures instructions (R&D Systems).
Colony Forming Assay
Cells ($1\times10^5$) were seeded in 6-well plates and incubated for 24 hours and exposed to DMSO or palbociclib for 24 hours and then re-seeded in 90 cm dishes in drug-free medium. Cells were incubated for 14 to 21 days to allow colony formation. Colonies were fixed and permeabilised using Carnoy's fixative (75% methanol, 25% Acetic acid) and stained with 1% crystal violet and counted.
Lentivirus Production
Cells stably expressing shRNA, miRNA or cDNA were generated using lentiviral transfection, as previously described using the pLKO.1 or pLEX-307 backbone (Moffat, J. et al., Cell 124: 1283-1298 (2006)). Multiple stable cell lines were generated for each protein knockdown; shRNA sequences were obtained from the RNAi Consortium database (Moffat, J. et al., Cell 124: 1283-1298 (2006)). CDK6 GeneArt cDNA sequences (K43M (Hu, M. G. et al., Blood 117: 6120-6131 (2011)), S178P (Bockstaele, L. et al., Mol. Cell Biol. 29: 4188-4200 (2009)) and R31C (Hu, M. G. et al., Blood 117: 6120-6131 (2011)) were purchased from ThermoFisher and cloned into the pLEX-307 backbone. For miRNA overexpression, ~500 bp of DNA encompassing each miRNA sequence was PCR purified and cloned into the pLEX-307 backbone, miRNA mimics were purchased and transfected into cells as a positive control for miRNA detection. Protein expression/miRNA expression/knockdown was confirmed after 5 days of selection in puromycin (1 μg/ml for both T47D and MCF7).
CRISPR/Cas9 Knockouts
CDK6 by CRIPSR/Cas9 was performed as previously described (Sanjana, N. E. et al., Nat. Meth 11: 783-784 (2014)). The following sgRNA sequence was cloned into the LentiCRIPSR v2 vector—sgCDK6-7 (targeting the 5'UTR): CCGCTCCACCCGCTCATCGT (SEQ ID NO: 2). Cells were selected using 1 μg/ml puromycin and protein knockout confirmed after ~12 days.

qPCR

Global miRNA profiling, custom miRNA micro arrays and miRNA qPCR were performed using the miRCURY LNA universal RT microRNA PCR system per the manufacturer's instruction (Exiqon). SYBR green signal was detected using a Lighcycler 480 system (Roche). Relative gene expression was calculated using the 2−ΔΔCT method (Livak, K. J. et al., Methods 25: 402-408 (2001)).

Exosome Purification and Quantification

Exosomes were purified from tissue culture medium using Total Exosome Isolation Reagent as per manufacturer's instructions (Thermo Fisher Scientific). Exosomes were quantified using EXOCET quantification assay as per manufacturer's instructions (StemBio).

Metastatic Breast Cancer Patient Biopsies

Tumor biopsy specimens were obtained from 44 receiving care for metastatic hormone-receptor positive (HR+) HER2 negative breast cancer at the Dana-Farber Cancer Institute as part of voluntary research protocol 05-246. Informed consent was obtained in accordance with institutional review board (IRB) approval and the Declaration of Helsinki. Extra tissue was donated when available for miRNA extraction and quantification. All patients received CDK4/6 inhibitors in the metastatic setting. Clinical records were reviewed to determine the duration on therapy, radiographic response, and reason for discontinuation. Collated data was de-identified and biopsy samples were phenotypically described as follows: sensitive—any biopsy obtained within 32 days of starting therapy or any time prior to therapy initiation in patients who had a response (via radiographic assessment on any intervening staging CT study) or achieved stable disease for at least six months; acquired resistant—any biopsy obtained within 32 days of drug discontinuation or anytime thereafter in a patient who achieved a response via radiographic imaging or stability for at least six months; and intrinsic resistant—any biopsy obtained within 120 days of initiating therapy or anytime thereafter in a patient who had progression on their first interval re-staging study or achieved less than six months of stable disease. More information on this cohort (Wander et al., 2018; ASCO, abstract; Mao et al., 2017; SABCS, abstract, each of which is incorporated herein by reference).

Biotin Labelled miRNA-mRNA Pulldown miRNA:mRNA pulldown and subsequent RNA seq was performed as previously described (Wani, S. et al., bioRxiv doi: http://dx.doi.org/10.1101/005439 (2014)). Briefly, biotin labelled miR-432-5p (Exiqon) was transfected into T47D cells and incubated for 24 hours at 37° C. Cell were then lysed, Biotin labelled miRNA:mRNA duplexes were captured using Dynabeads MyOne Streptavidin C1, which were washed and mRNA purified. mRNA was amplified using Illumina Total prep RNA Amplification kit and cRNA hybridized onto an Illumina Human HT-12 array. Data was expressed as reads per kilobase of transcript per million mapped reads (FKPM) and pulldown compared to total RNA. Significantly enriched mRNAs were then subjected to pathway analysis and correlated with gene expression data. Gene expression analysis was performed with Affymetrix Human Genome U133A 2.0 library as per manufactures instructions.

In Vivo Xenograft Assay

Female nude mice (NCr-Foxn1$^{NU}$, Tactonic Laboratories) were maintained and handled in isolators under specific pathogen-free conditions for tissue distribution and efficacy studies in accordance with local guidelines and therapeutic interventions approved by the Animal Care and Use Committee of Dana-Farber Cancer Institute. Mice were implanted with 17β-estradiol pellets (0.36 mg, 90-day release, Innovative Research of America) prior to cell implantation. Palbociclib resistant MCF7 cells were subcutaneously implanted into the flanks of the mice (n=20), 7×10$^6$ cells in 100 µL culture medium+50% matrigel (BD Biosciences). Palbociclib was administered daily via oral gavage at 100 mg/kg starting 24 hours after cell injection. Once tumors were established to be growing in the presence of drug (n=16), palbociclib treatment was ceased for 28 days. After 28 days with no treatment, palbociclib treatment was resumed (n=12). Tumors were measured throughout the experiment and relative tumor volume calculated.

Statistics

All statistics were calculated using Graphpad Prism 7.

Figure 1B:
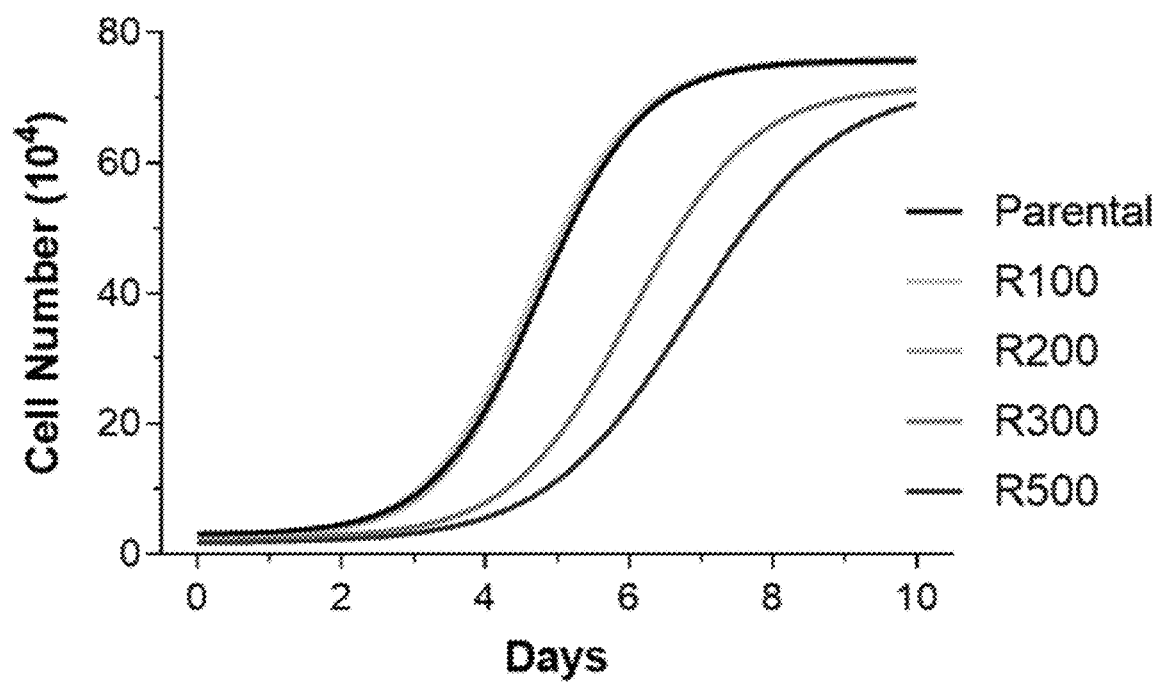
Figure 8A:
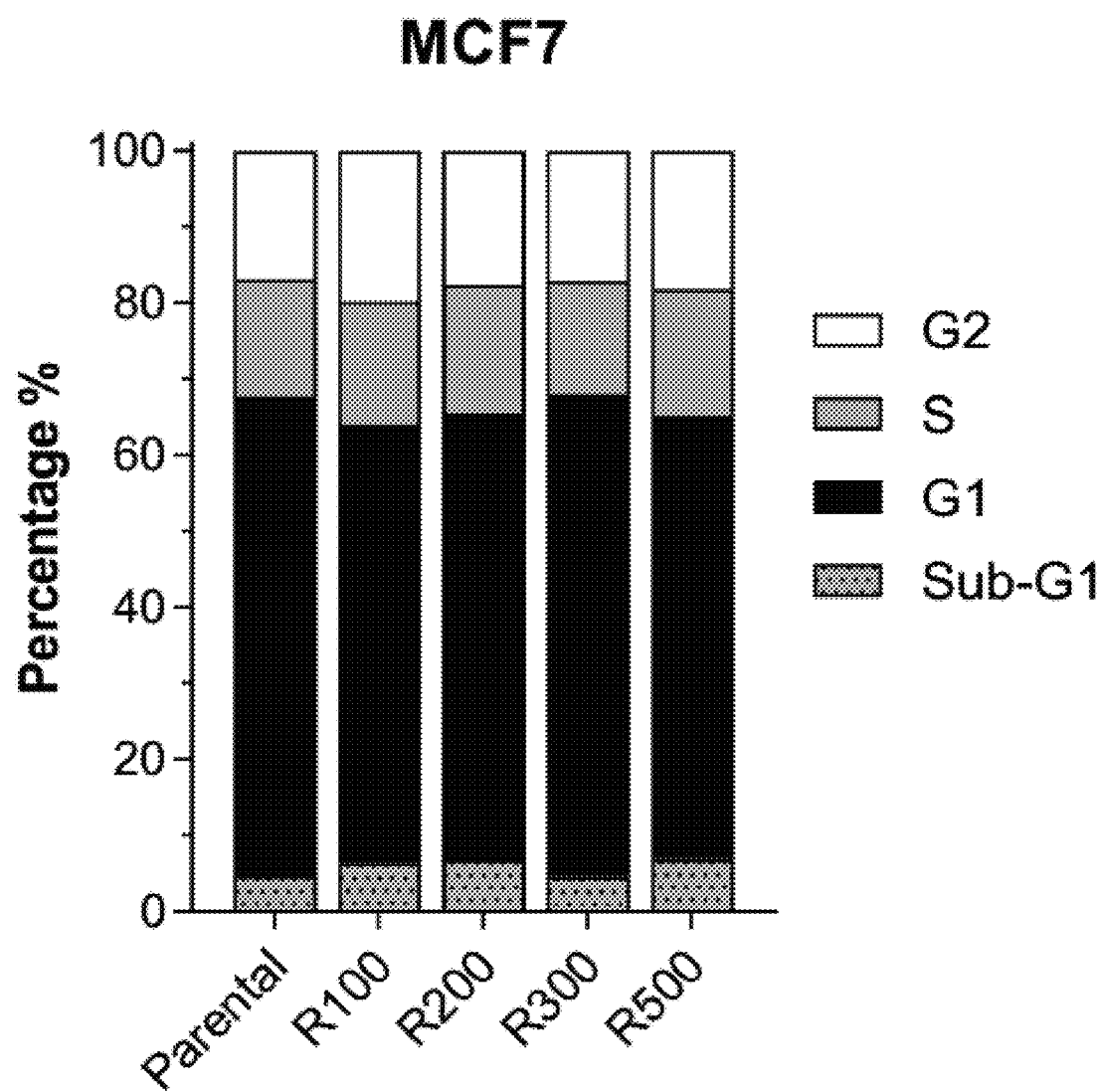
FIG. 8A-FIG. 8F shows a series of graphs showing that generated CDK4/6 inhibitor resistant cells lines have dramatically increased CDK6 protein expression.
Figure 8B:
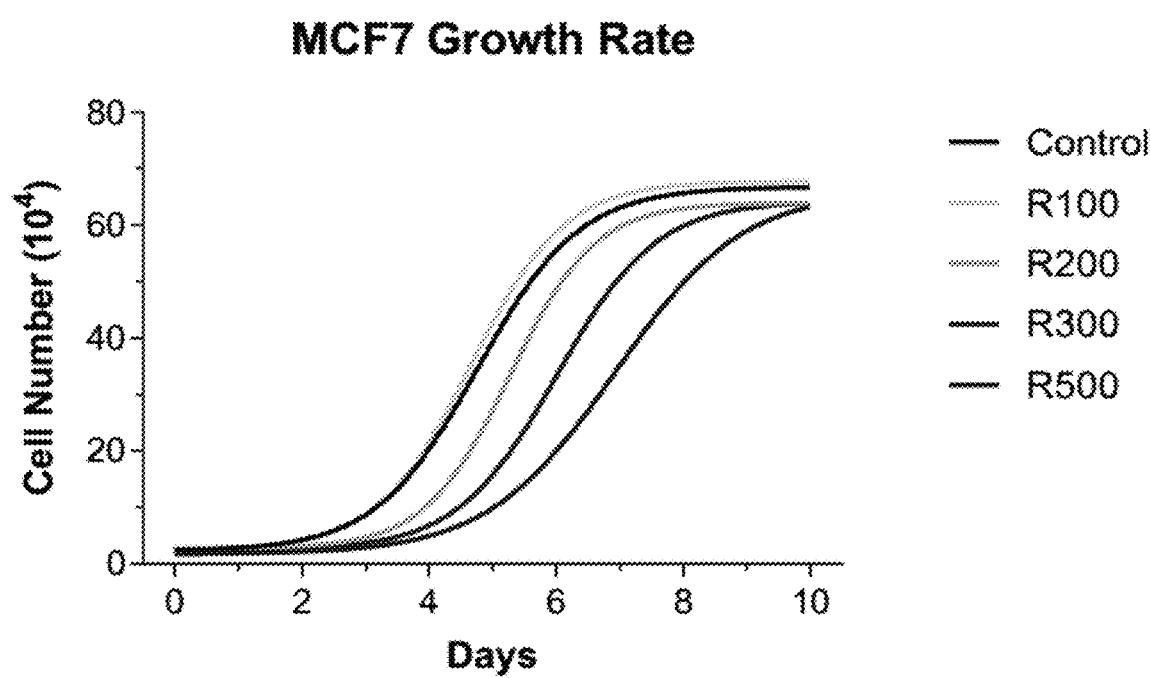
Figure 8C:
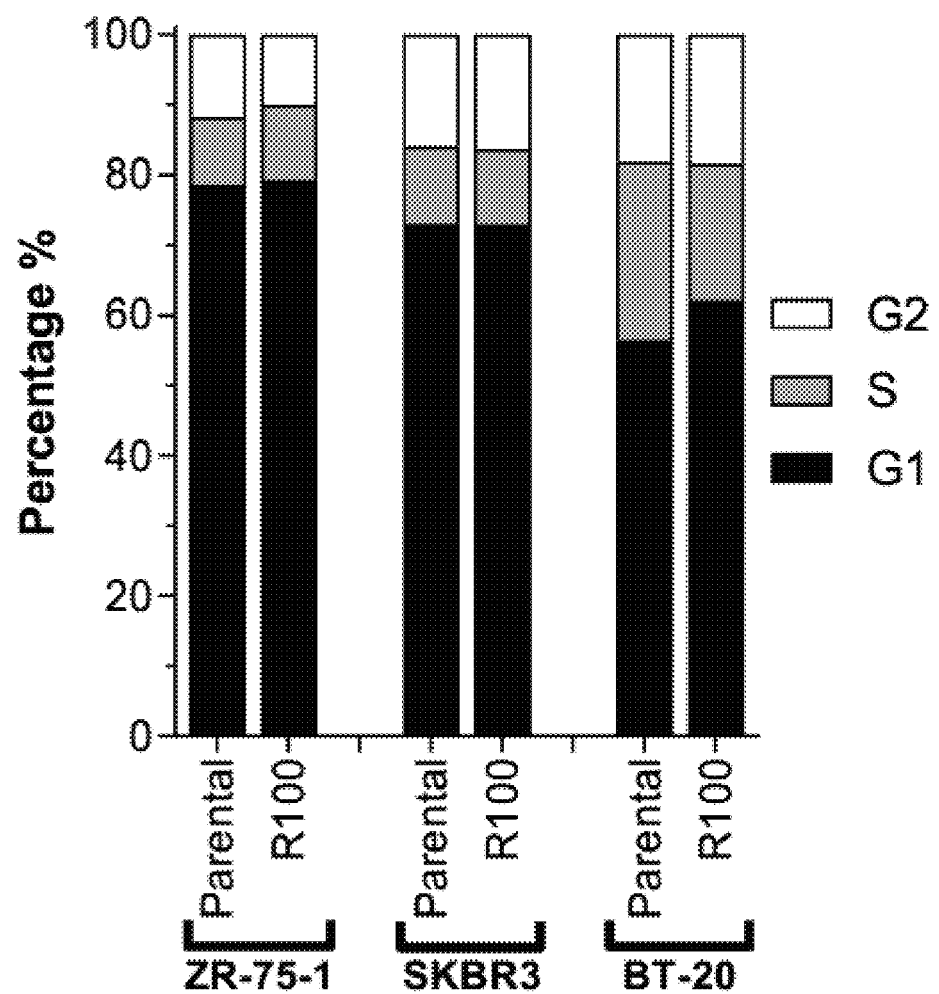
Figure 8D:
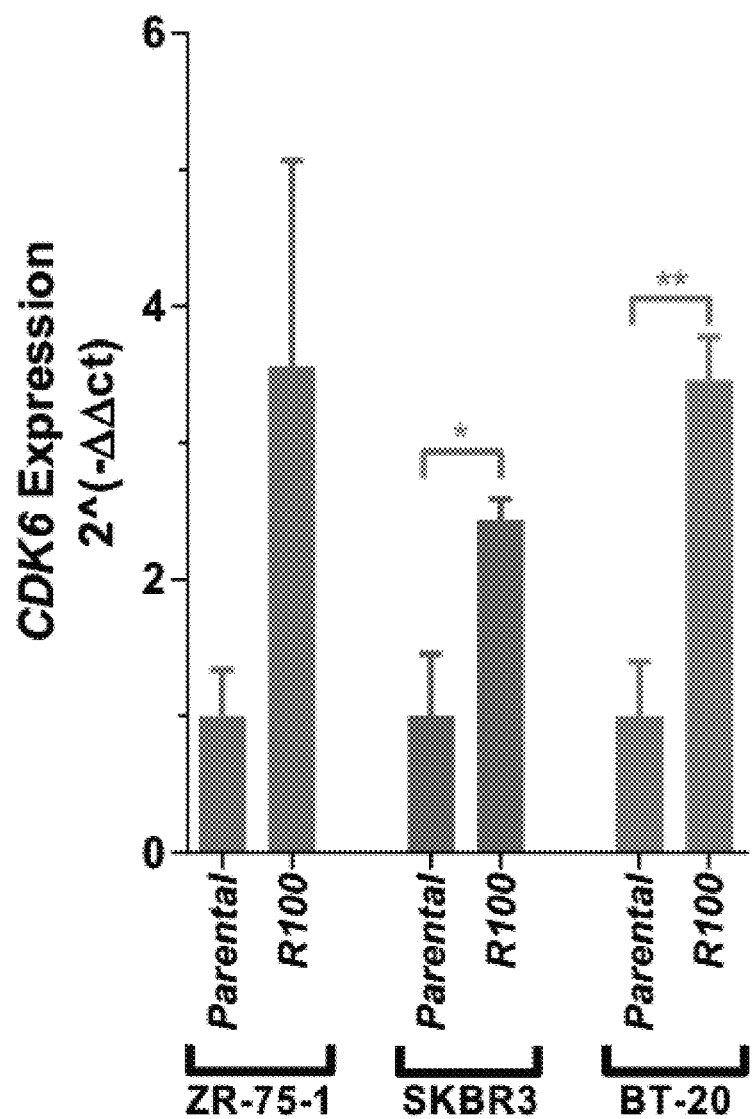
Figure 8E:
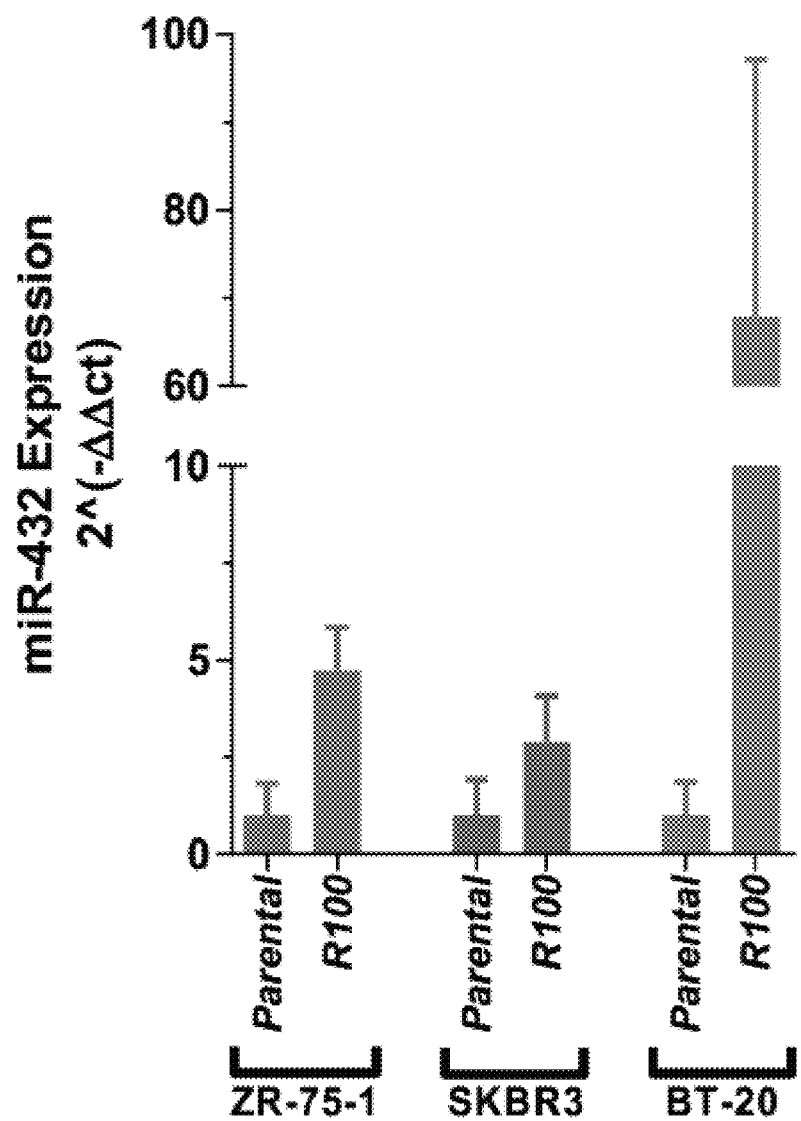
Figure 8F:
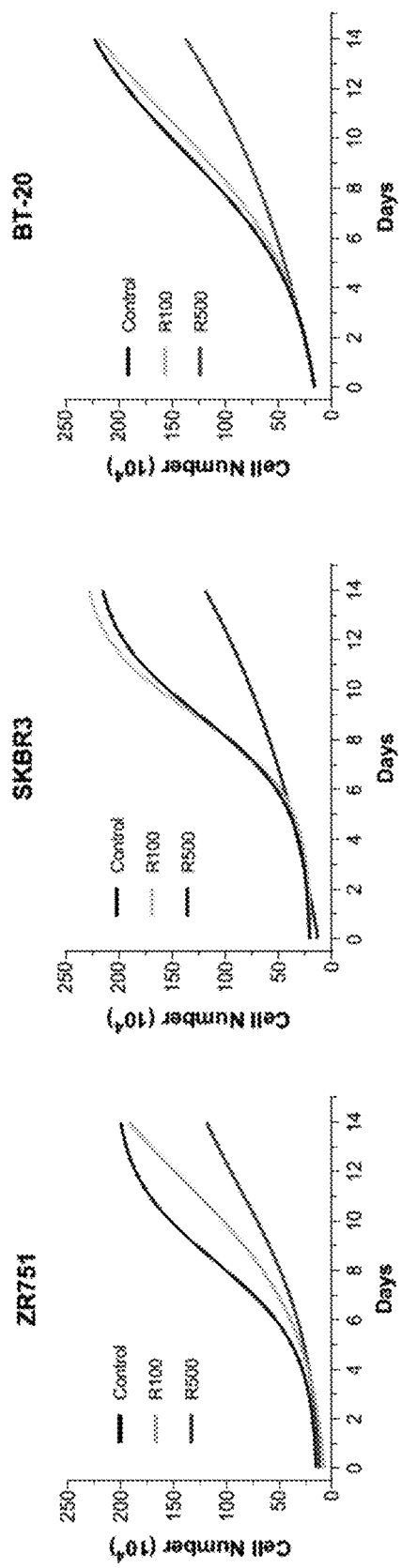

Example 2: CDK4/6 Inhibitor-Resistant Cells have Increased CDK6 and Cyclin D1 Expression Experimentation generated palbociclib-resistant T47D ER-positive breast cancer cells by continuous exposure to 100 nM drug and weekly monitoring of cell cycle analysis by quantification of DNA content. Initial exposure (week 0) led to a profound G1 arrest with more than 90% of cells in the G1 phase of the cell cycle. G1 arrest persisted to this degree for 5 weeks in the presence of palbociclib, and thereafter began to gradually decrease as cells took on a normal cell cycle profile (FIG. 1A). After 12 weeks of continuous palbociclib exposure, the cell cycle distribution was indistinguishable from that of parental cells, as was the rate of proliferation, and they were deemed resistant (FIG. 1A and FIG. 1B). The palbociclib concentration was then gradually escalated; each gradation (100→200→300→500 nM) was applied once a normal cell cycle profile was achieved, until cells were resistant to 500 nM palbociclib (FIG. 1A). While cells resistant to each dose of palbociclib had indistinguishable cell cycle profiles, the growth rate of the 300 and 500 nM resistant cells (R300 and R500) had a slower doubling time (Parental=23.6, R100=23.6, R200=23.6, R300=28.8, R500=31.8 hours, FIG. 1B). Similar palbociclib-resistant derivatives were generated from MCF7 and ZR-75-1 ER-positive breast cancer cells, as well as SKBR3 and BT-20 cells, representative of R-expressing HER2-amplified and triple-negative breast cancer subsets, respectively (FIG. 8A and FIG. 8B).

Figure 1C:
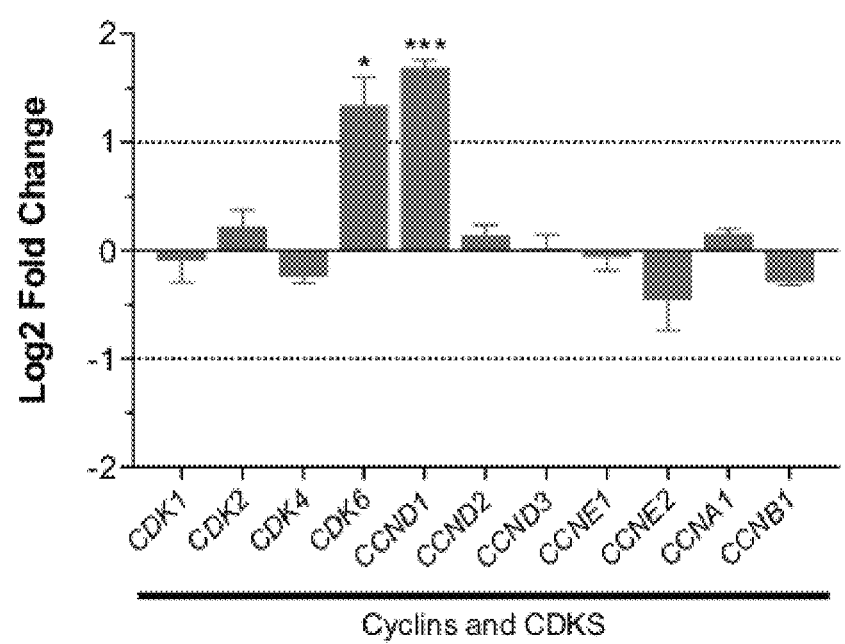
Figure 1D:
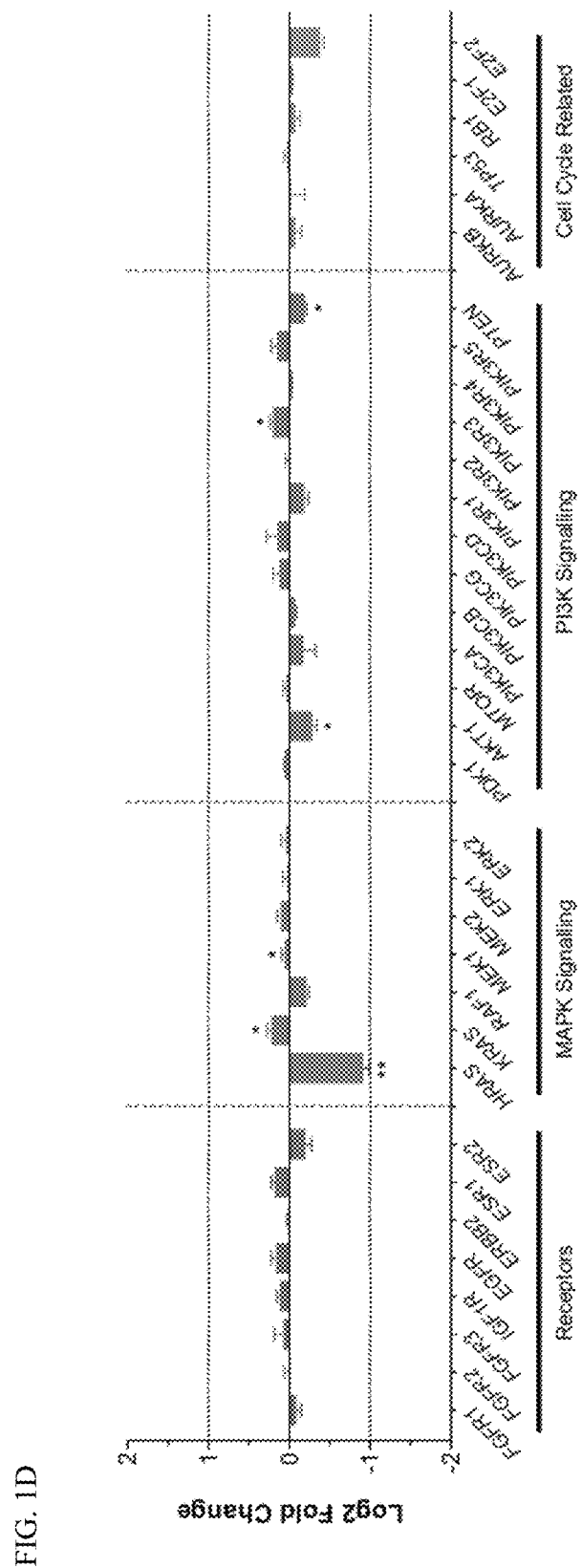
Figure 1E:
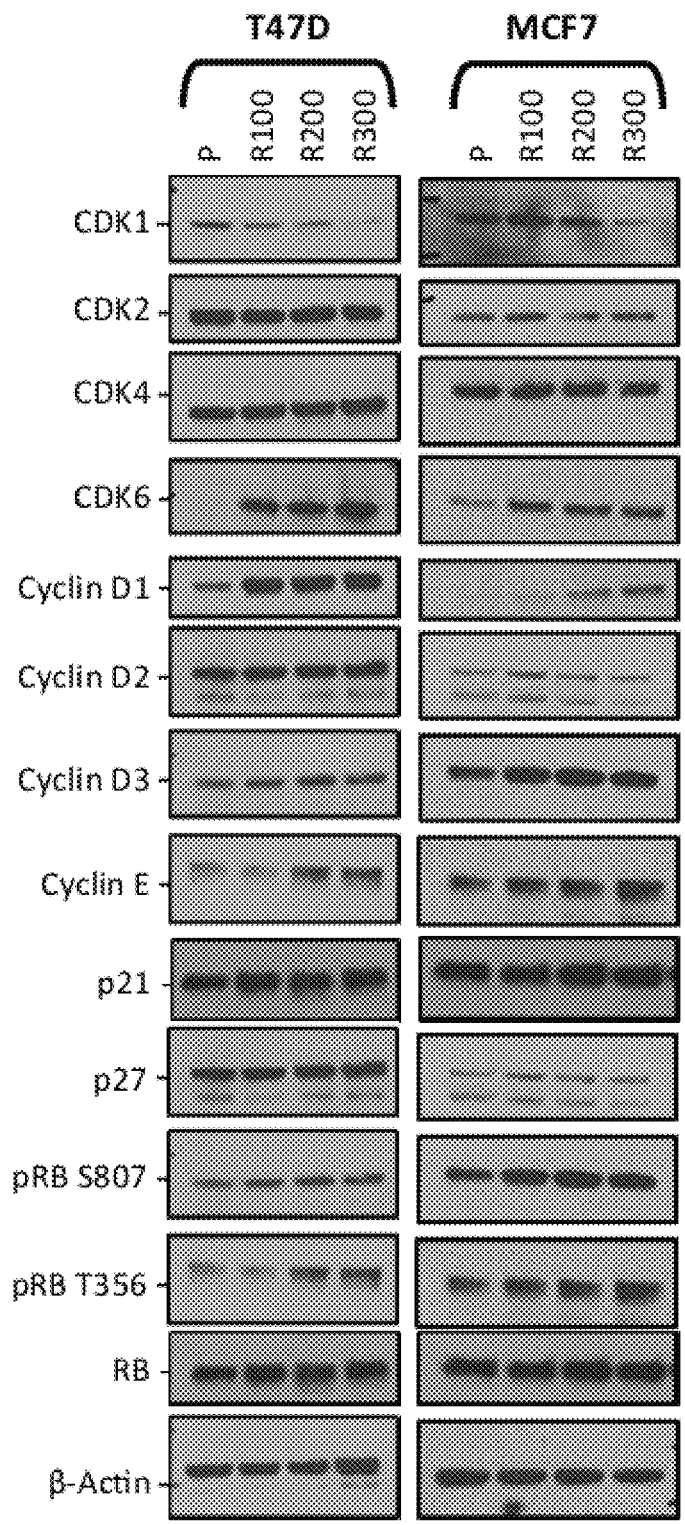
Figure 1F:
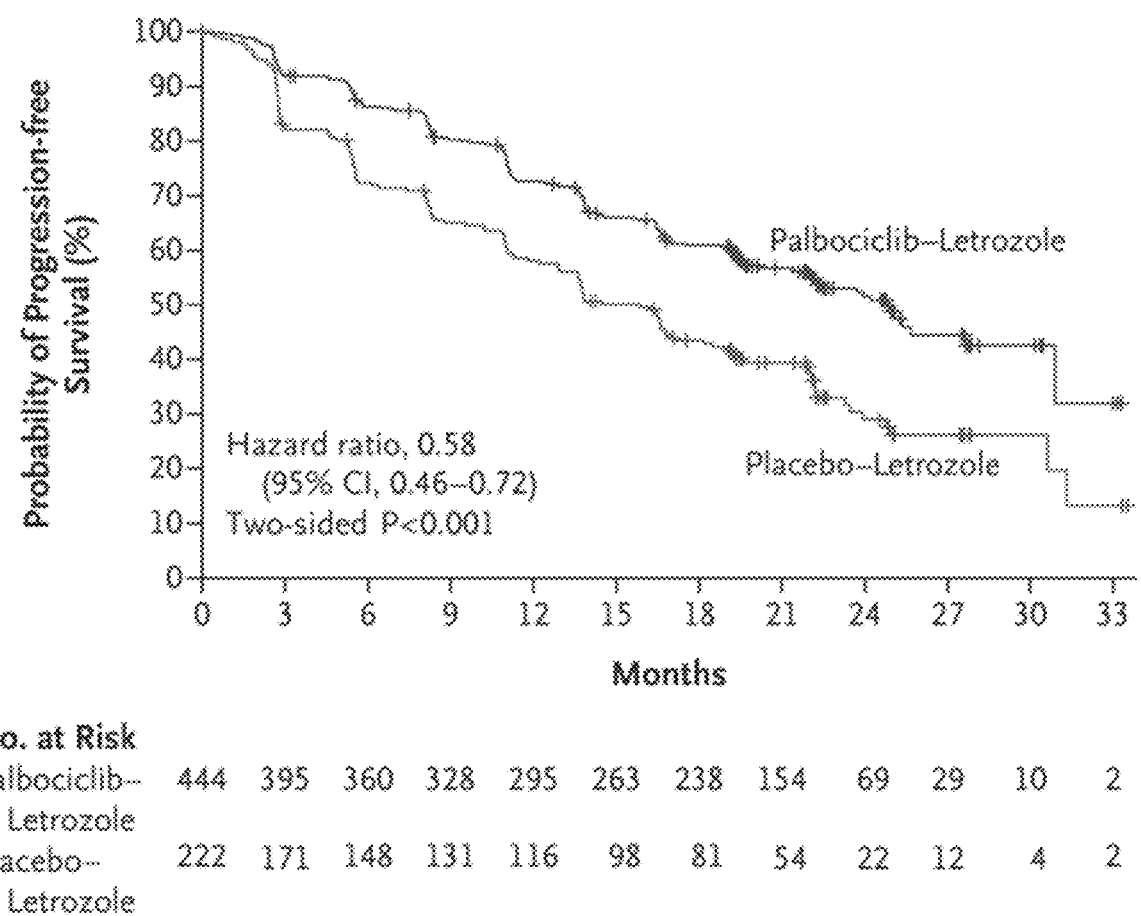
Figure 9:
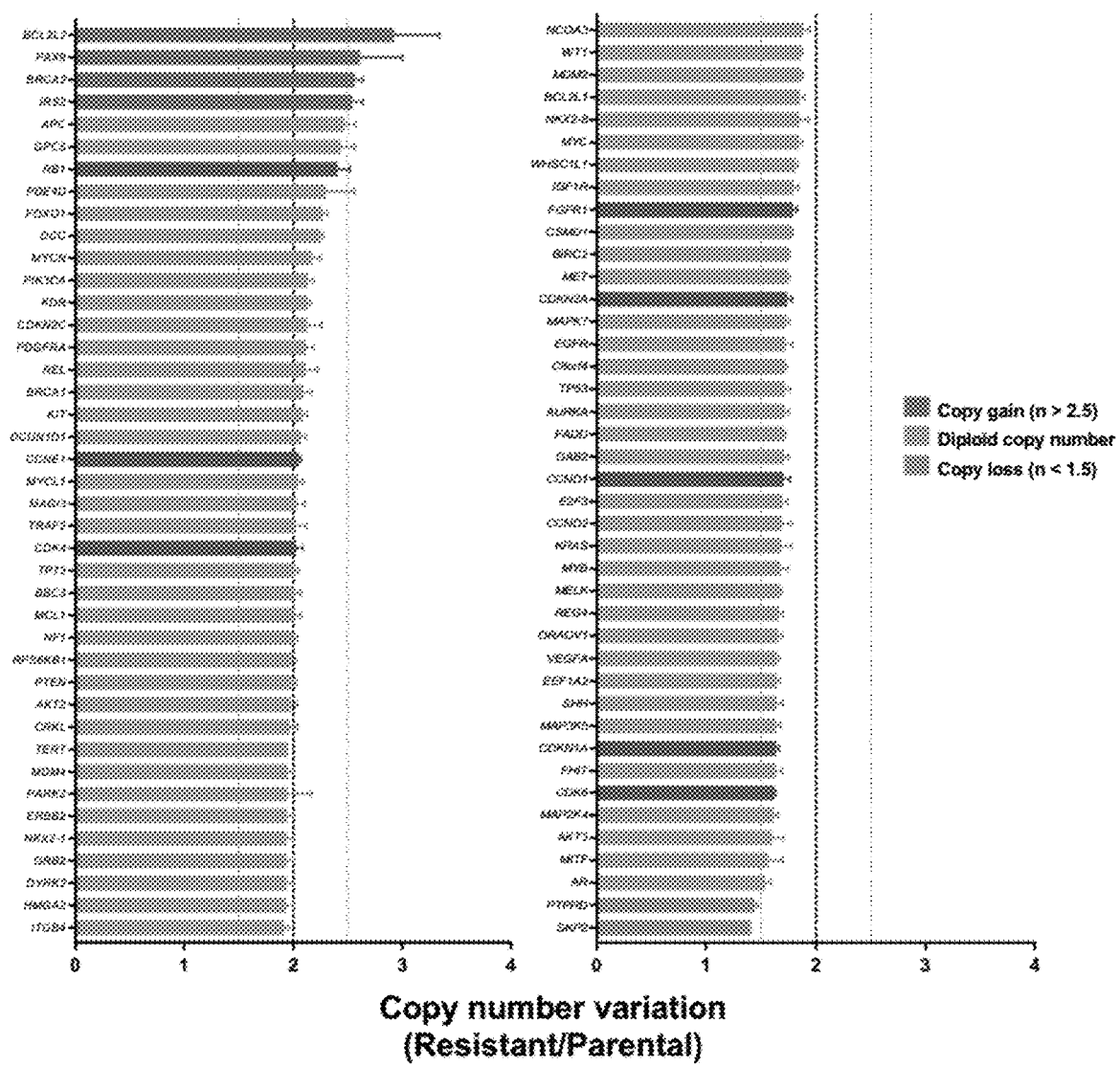
FIG. 9 is a series of bar charts showing copy number variation analysis in parental and palbociclib resistant T47D cells. Copy number variation was analyzed using nanoString nCounter v2 Cancer CNV Assay. Copy number estimations are expressed as resistant cell/parental cell. Copy number gains were taken as a ratio of >2.5, copy number loss was taken as a ration of <1.5, as per manufactures instructions. Dark grey bars are highlighted as they have been previously implicated in CDK4/6 inhibitor resistance.

Analysis of cell cycle genes via qPCR revealed a significant increase in CDK6 and CCND1 expression in resistant (R100) vs. parental cells. These increases in mRNA expression were not accompanied by gene amplification as there was no variation in the copy number of these genes (FIG. 9). No significant changes were observed in the remaining cell cycle (i.e., cyclin and CDK) genes (FIG. 1C). Multiple genes related to cell cycle, growth, and/or CDK4/6 inhibitor resistance were also analyzed (FIG. 1D). There were significant, albeit small (<2-fold), changes in the expression of HRAS, KRAS, MEK1, AKT1, PIK3R3, and PTEN in resistant cells. In correlation with gene expression, the greatest changes in protein expression were increased CDK6 and cyclin D1, observed in both T47D and MCF7 cells, with expression increasing stepwise in cells resistant to higher doses of palbociclib (FIG. 1E). A small stepwise increase in Cyclin E levels was also observed, along with a progressive decrease in CDK1 expression. Phosphorylation of Rb at the CDK4/6 site Ser$^{807}$/Ser$^{811}$ and Thr$^{356}$ was maintained in all resistant cells (FIG. 1E). Overall, these results indicate that palbociclib resistant cells overexpress CDK6 and that CDK4/6 inhibitor-resistant cells are driven by CDK6 and cyclin D1 expression.

Figure 2A:
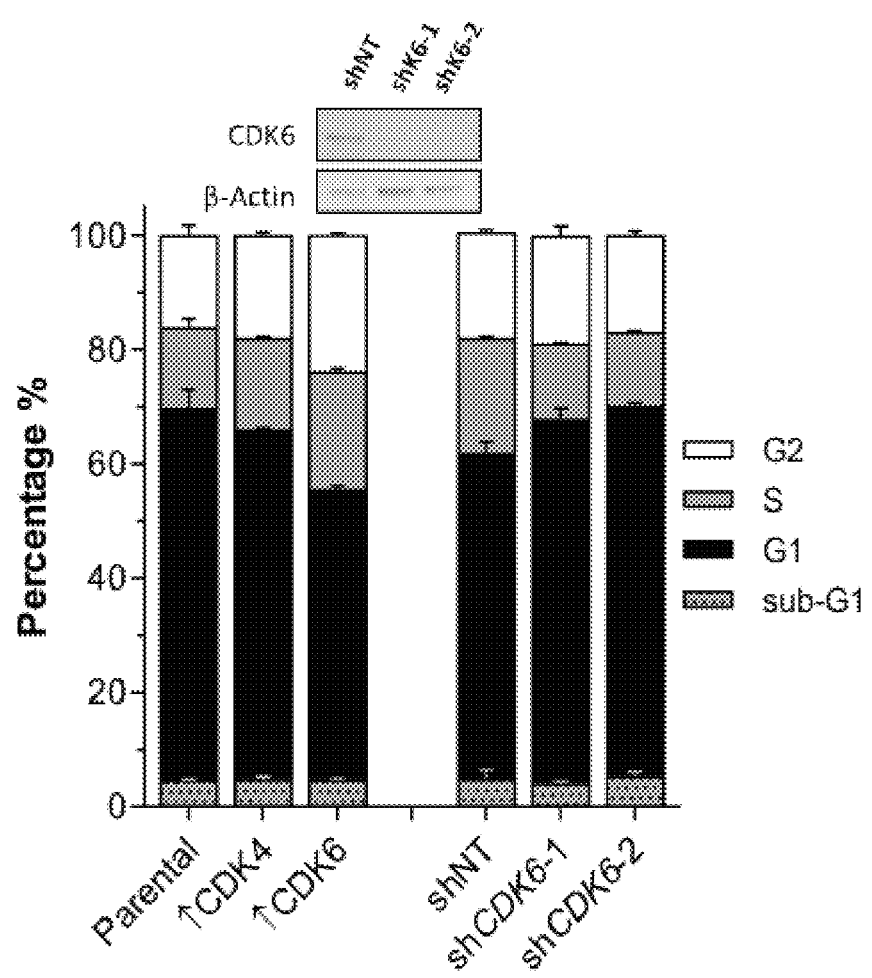
FIG. 2A-FIG. 2E shows a series of graphs displaying resistance to CDK4/6 inhibition is mediated by high CDK6 expression.
Figure 2B:
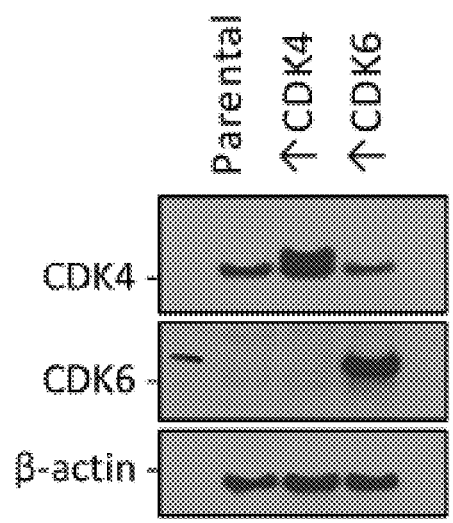
Figure 2C:
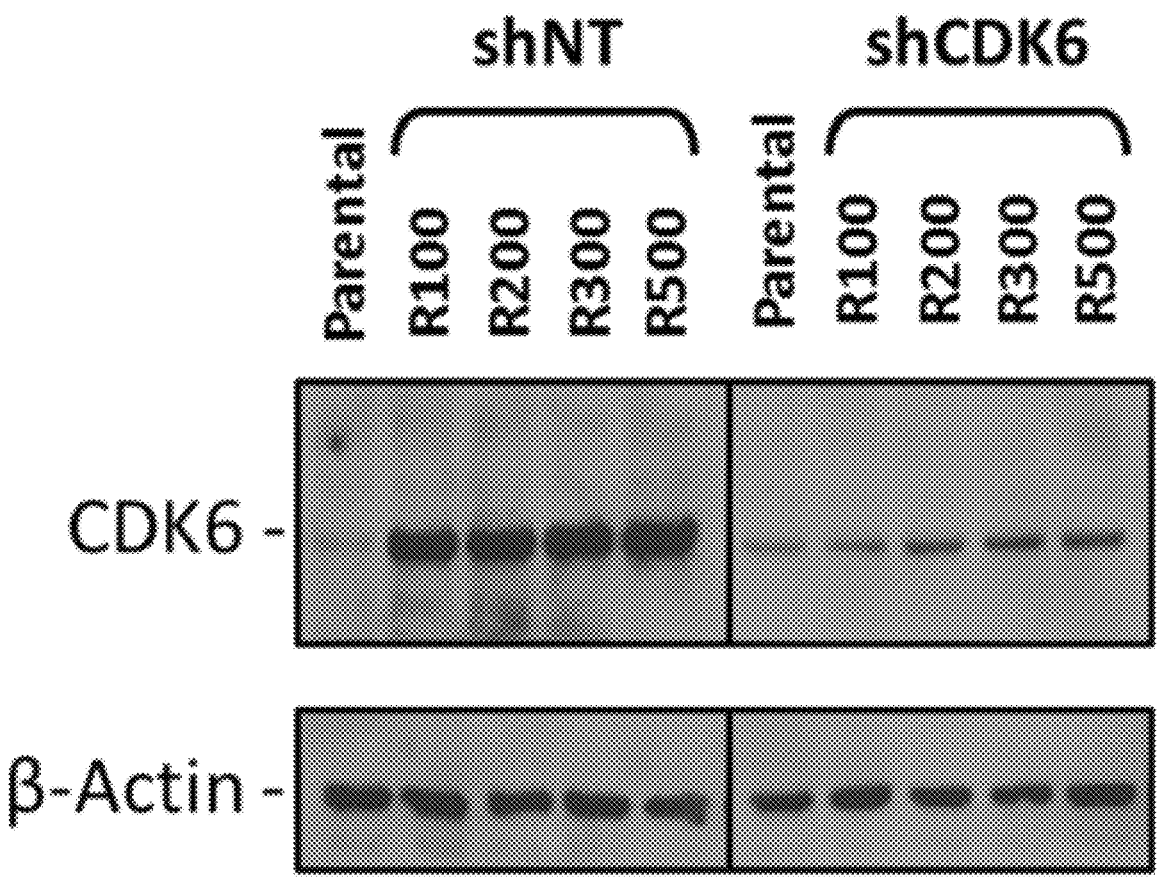
Figure 2D:
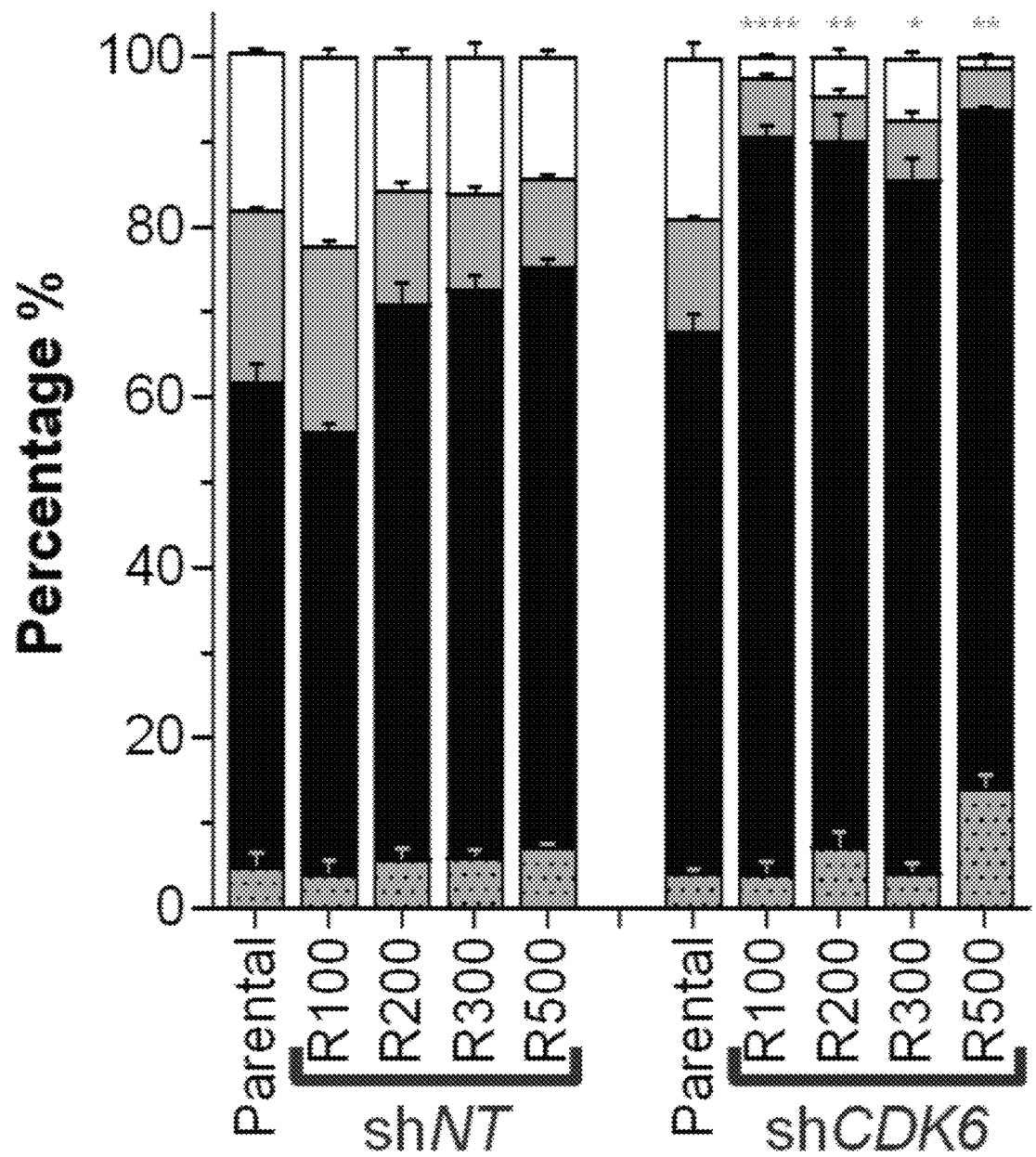

Example 3: CDK6 Knockdown Re-Sensitizes Resistant Cells, and Overexpression of CDK6 Confers Resistance in Parental Cells To determine the contribution of CDK6 to palbociclib resistance, CDK6 expression in both resistant and parental T47D cells was manipulated. Neither overexpression of CDK4 or CDK6, nor depletion of CDK6 significantly influenced the cell cycle profile of parental T47D cells (FIG. 2A). Substantial overexpression of CDK4 (↑CDK4) and CDK6 (↑CDK6) was achieved in parental cells and confirmed by western blot (FIG. 2B). Additionally, robust knockdown of CDK6 was confirmed in resistant cells lines (FIG. 2C). Of note, depletion of CDK6 in resistant cells lines reduced CDK6 protein expression to a level approximating that seen in parental cells (FIG. 2C). Non-target (NT) shRNA had no effect on the cell cycle of resistant cells (R100-R500). shRNA-mediated depletion of CDK6 had no effect on the cell cycle in parental cells (FIG. 2A), but re-sensitized all resistant cells (which were maintained in palbociclib), evident by the significant increase in G1 population in these cells (FIG. 2D).

Figure 2E:
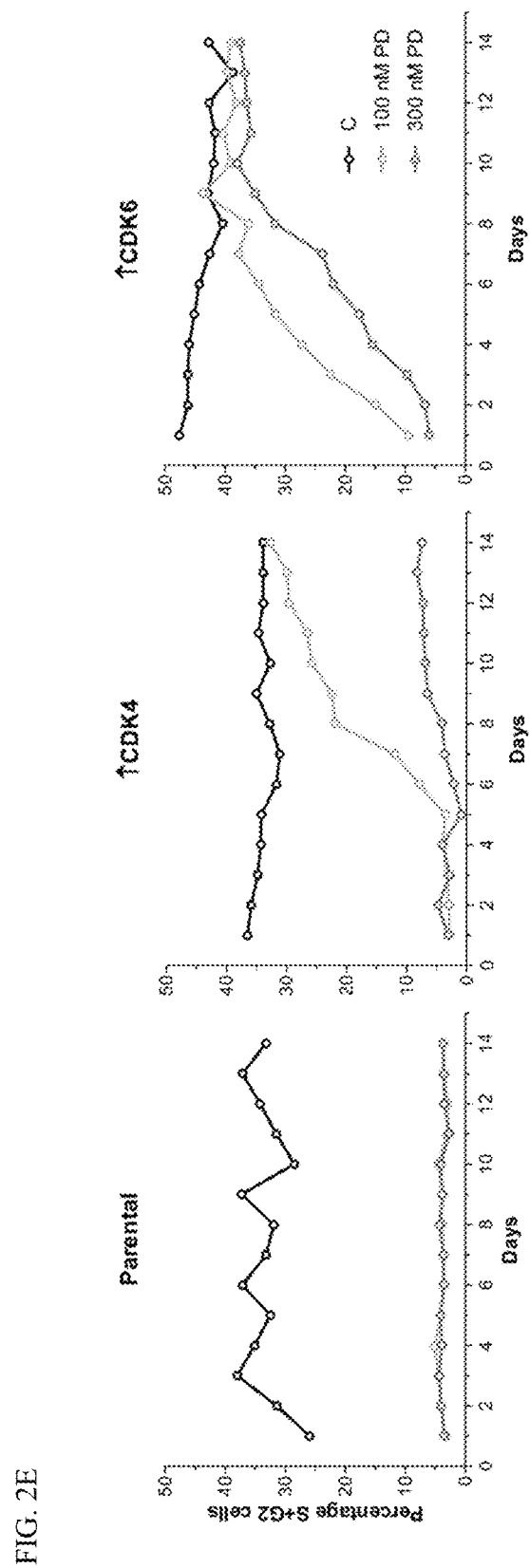
Figure 10A:
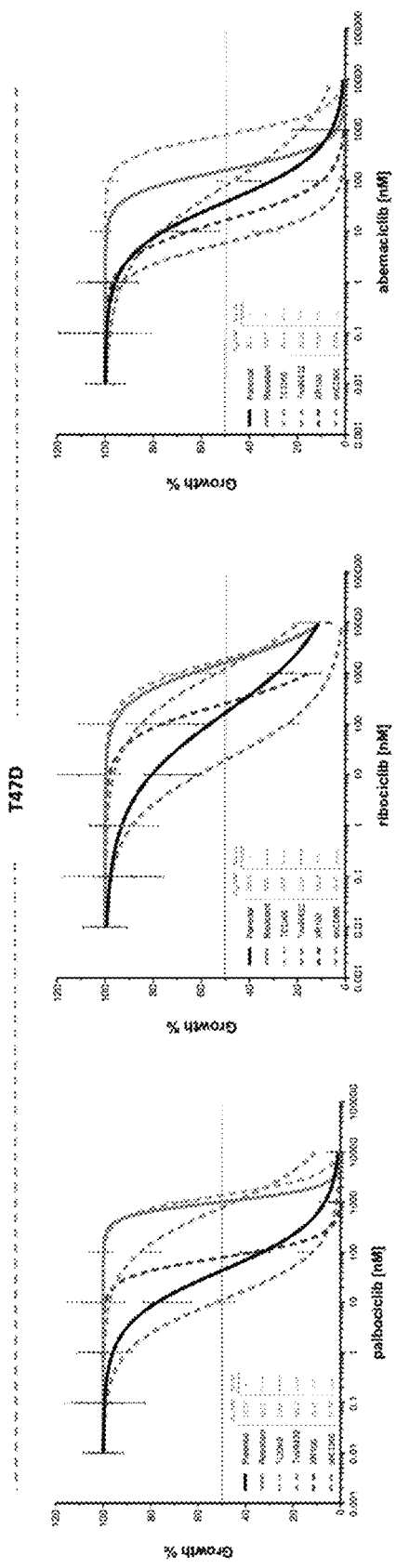
FIG. 10A-FIG. 10B is a series of line graphs showing that palbociclib resistant cells are significantly more resistant to ribociclib, and moderately more resistant to abemaciclib.
Figure 10B:
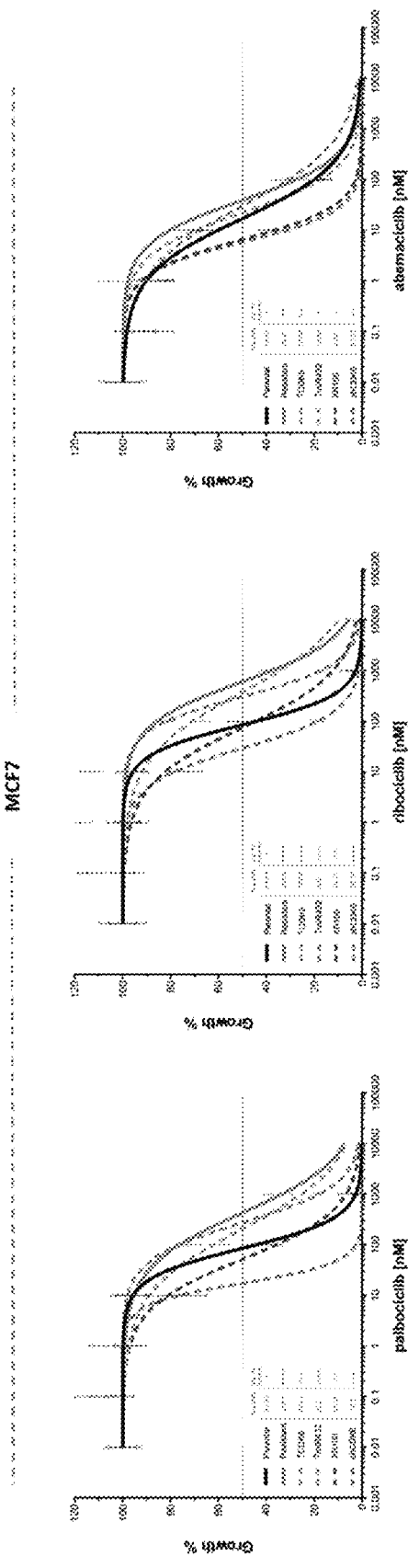

Treatment of parental T47D cells with 100 nM or 300 nM palbociclib caused sustained G1 arrest, as demonstrated by the low percentage of cells in S and G2 phases of the cell cycle, which persisted for 14 days. CDK4-overexpressing cells treated with 100 nM palbociclib returned to a normal cell cycle profile after 14 days of continuous treatment, although they remained stalled in the presence of 300 nM palbociclib. In contrast, CDK6-overexpressing cells became resistant to both 100 and 300 nM palbociclib within 10 days (FIG. 2E). Furthermore, CDK6 overexpression in parental T47D or MCG-7 cells significantly increased the $GI_{50}s$ of not only palbociclib, but also of ribociclib and abemaciclib in growth inhibition assays (FIG. 10A and FIG. 10B).

Overall, these results indicate that CDK6 knockdown reverses resistance and that CDK6 overexpression confers resistance.

Figure 3A:
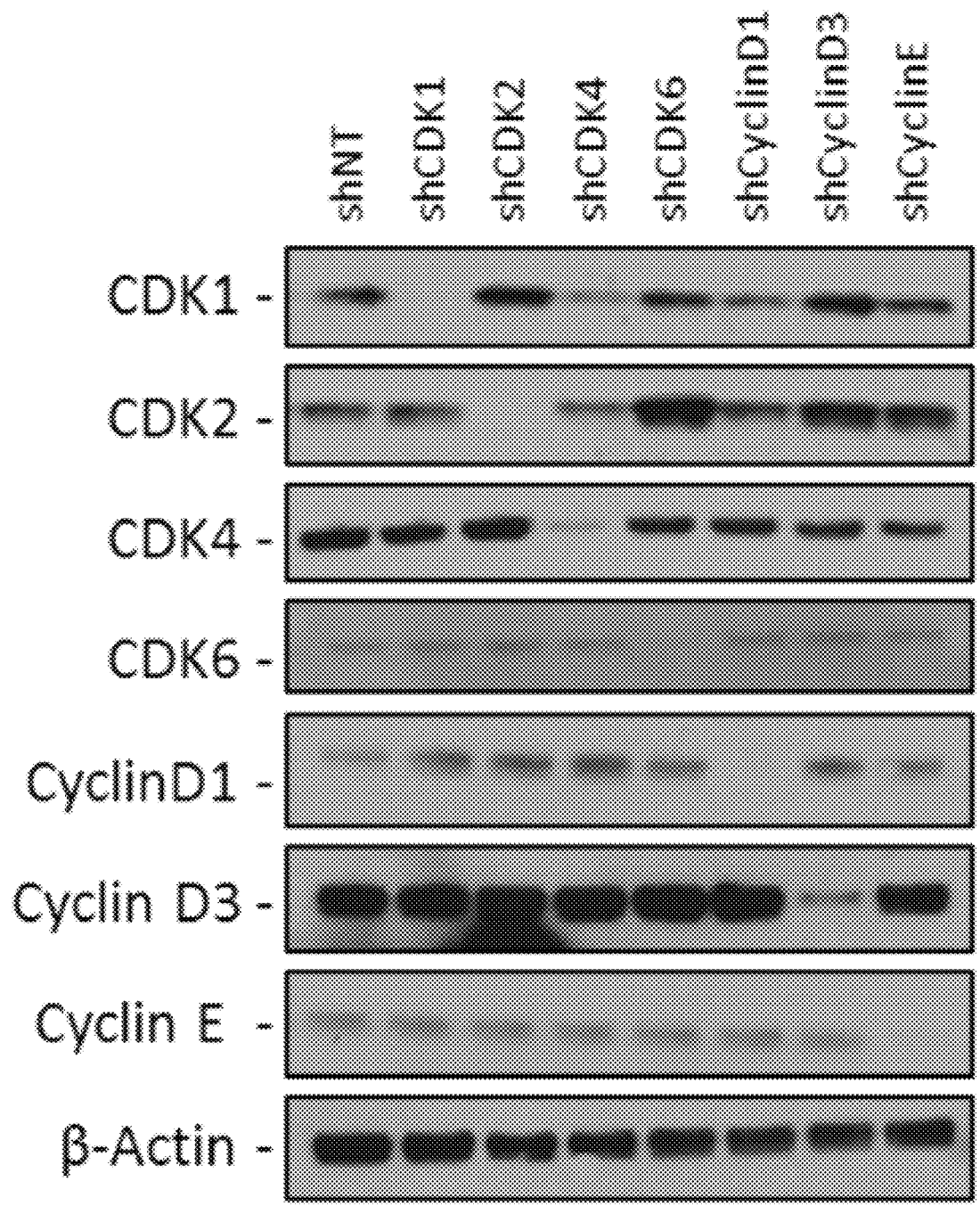
FIG. 3A-FIG. 3F show a series of graphs depicting CDK6 expression and activity contributes to cell survival after palbociclib exposure.
Figure 3B:
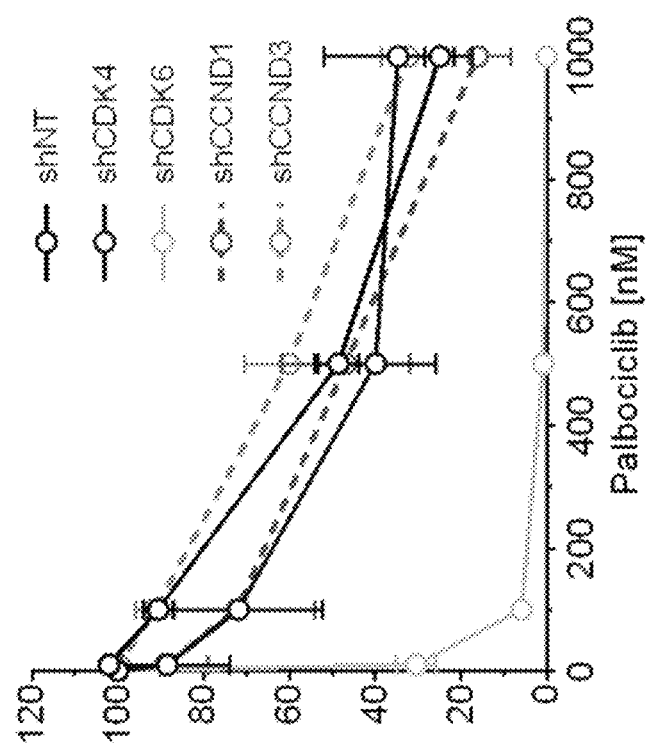
Figure 3B:
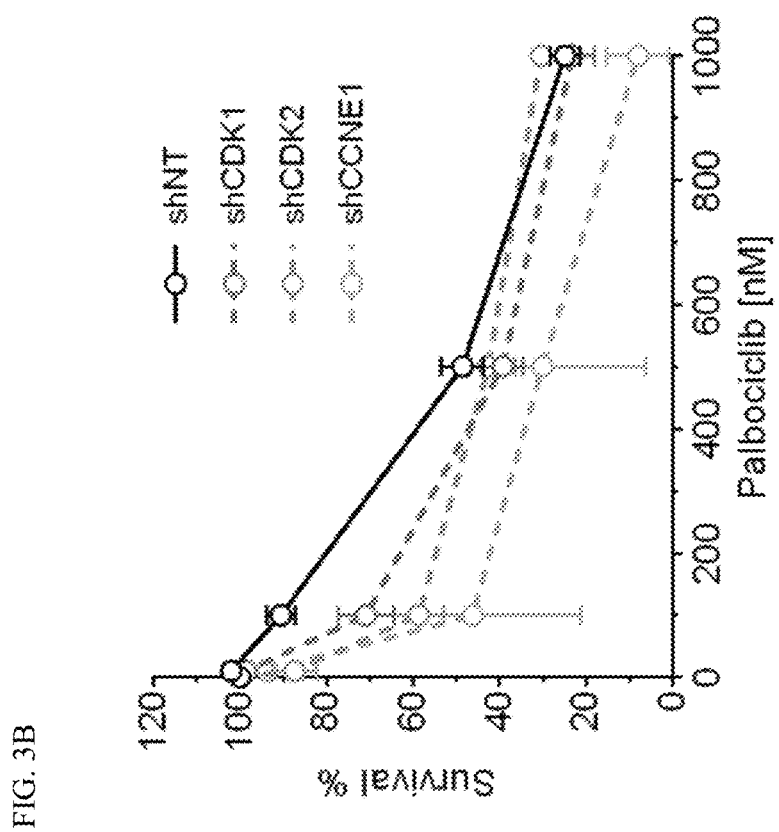
Figure 3C:
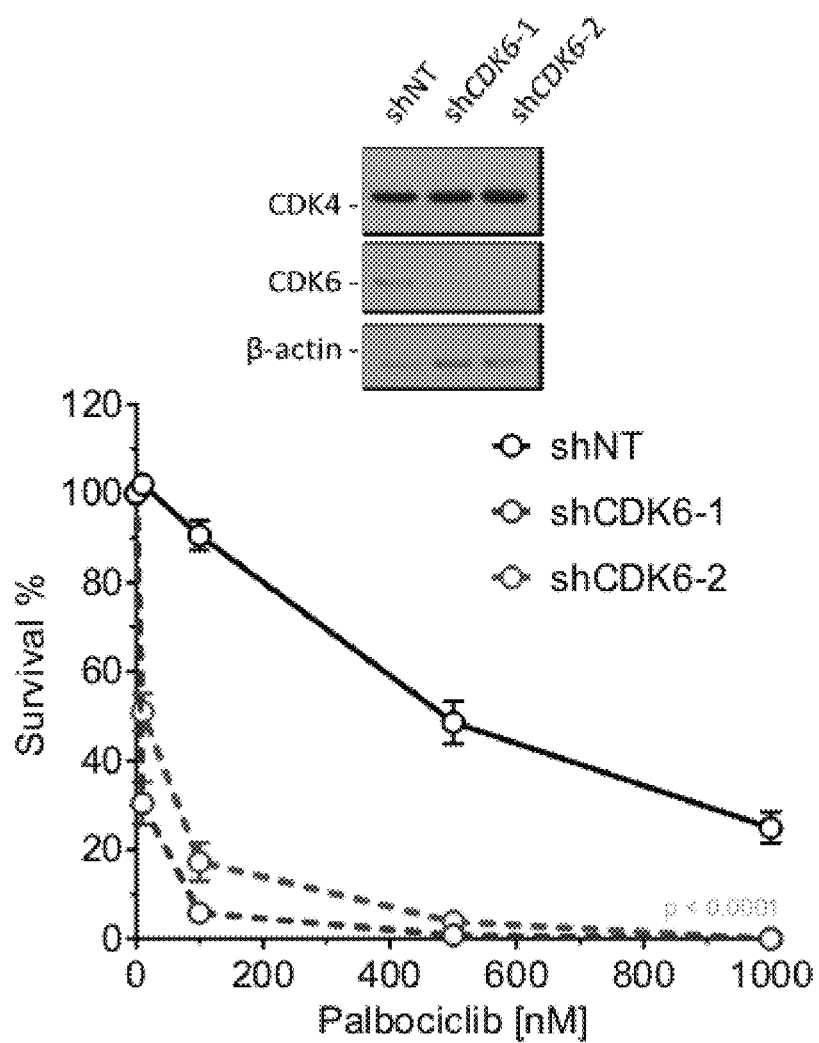

Example 4: CDK6 Contributes to the Survival of ER-Positive Breast Cancer Cells after Palbociclib Exposure To broadly assess the effects of cell cycle proteins on the response to palbociclib, clonogenic survival assays were performed after knockdown of a variety of cyclins and CDKs in parental T47D cells. Robust knockdown was achieved with each of the shRNAs (FIG. 3A). shRNA-mediated depletion of CDK6 resulted in significantly lower survival after palbociclib treatment compared to cells expressing a non-target shRNA control, or cells expressing shRNAs targeting other cell cycle proteins (FIG. 3B and FIG. 3C). CDK6 knockdown alone had no effect on the cell cycle profile; however, CDK6-depleted cells treated with palbociclib had significantly more sub-G1 DNA content than control cells (FIG. 3D).

Figure 3D:
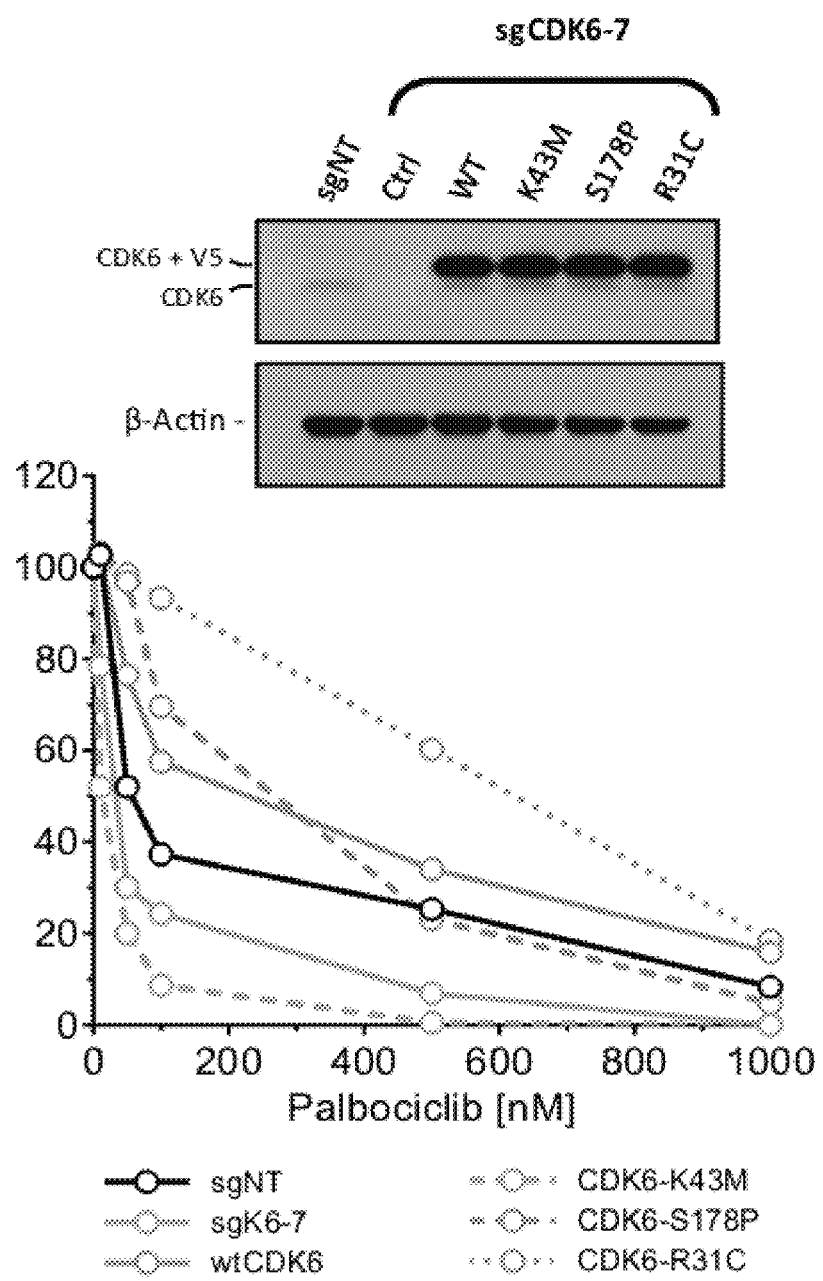
Figure 3E:
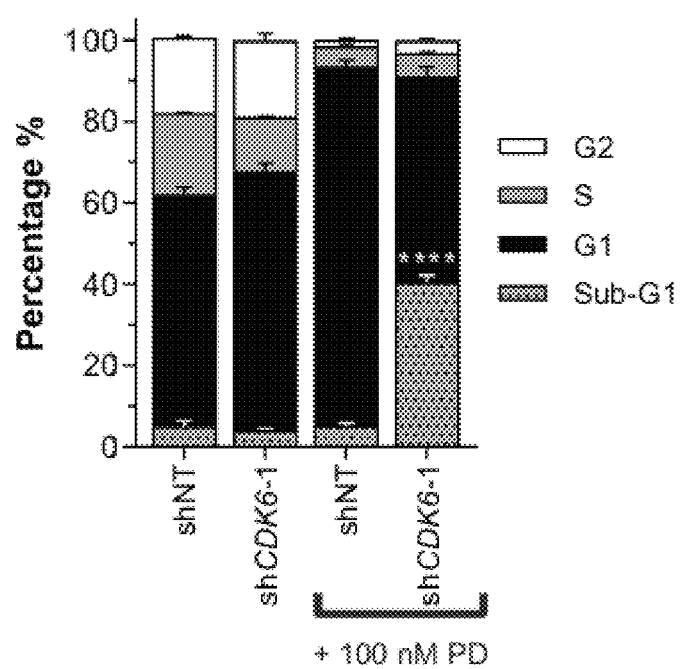
Figure 3F:
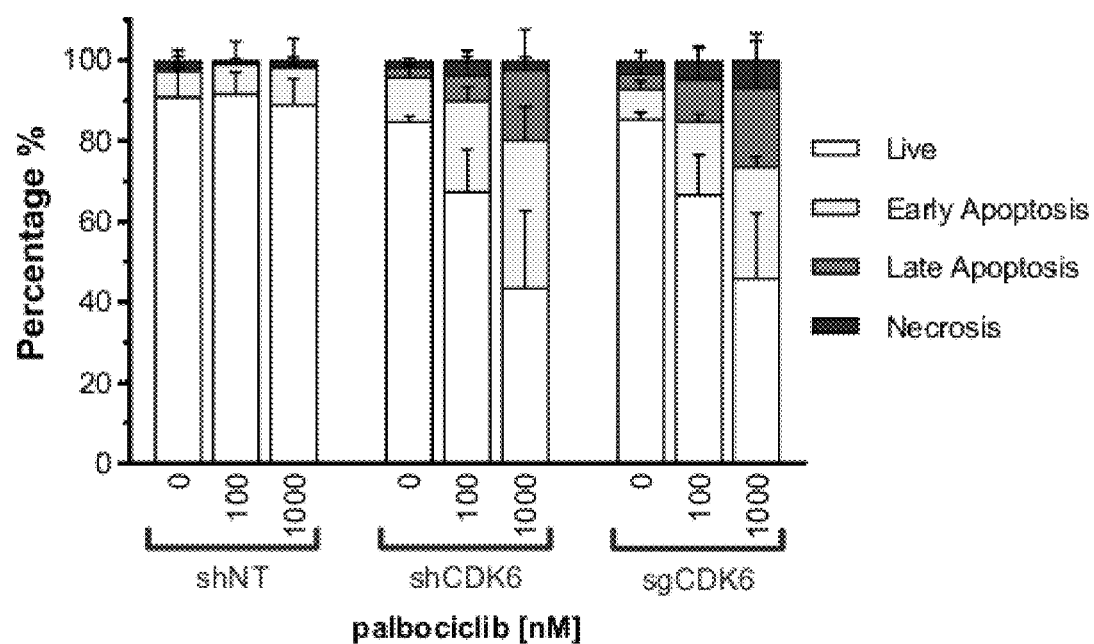

To determine if the kinase activity of CDK6 was required for the survival of T47D cells after palbociclib exposure, CRISPR/cas9 mediated knockout was used with an sgRNA targeting the 5'UTR, and then overexpressed wild-type CDK6 or one of several mutant kinases (FIG. 3D). A similar decrease in survival after palbociclib treatment was evident for both CDK6 knockout cells (sgK6-7, LC50=34.2 nM) and kinase dead CDK6-expressing cells (K43M, LC50=26.6 nM), compared to control (sgNT, LC50=66.199) and wild-type (WT, LC50=229.0 nM) cells. Additionally, overexpression of CDK6 proteins that are INK4-insensitive (R31C, LC50=632.0 nM) or constitutively active (S178P LC50=269.0 nM) substantially increased survival after palbociclib treatment (FIG. 3D). CDK6 knockdown alone had no effect on the cell cycle profile; however, CDK6-depleted cells treated with palbociclib had significantly more sub-G1 DNA content than control cells (FIG. 3E), likely due to a marked increase in apoptosis in both CDK6 knockdown and knockout cells. In contrast, palbociclib had no effect on the apoptotic fraction of shNT-expressing cells (FIG. 3F).

Taken together, these results suggest that the low-level CDK6 expression in parental T47D cells is critical for survival in response to palbociclib, perhaps explaining the propensity of cells to overexpress CDK6 under the selective pressure of drug as acquired resistance emerges.

Figure 4A:
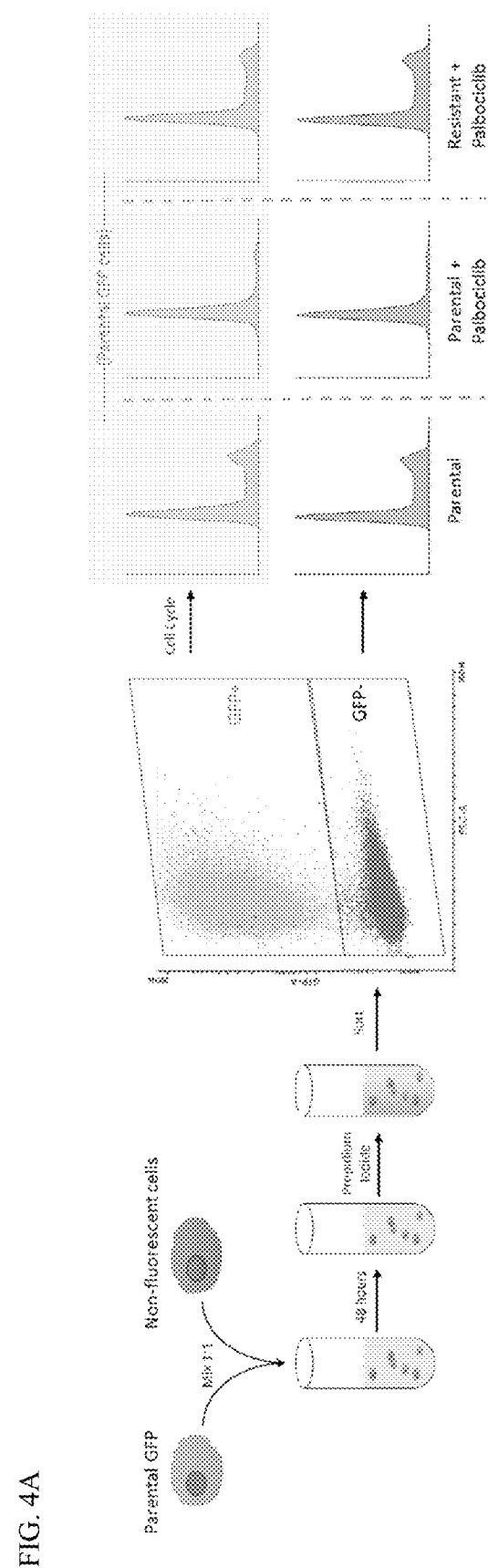
FIG. 4A-FIG. 4D show a series of graphs depicting CDK4/6 inhibitor resistance is transmitted via exomsomal signaling.
Figure 4B:
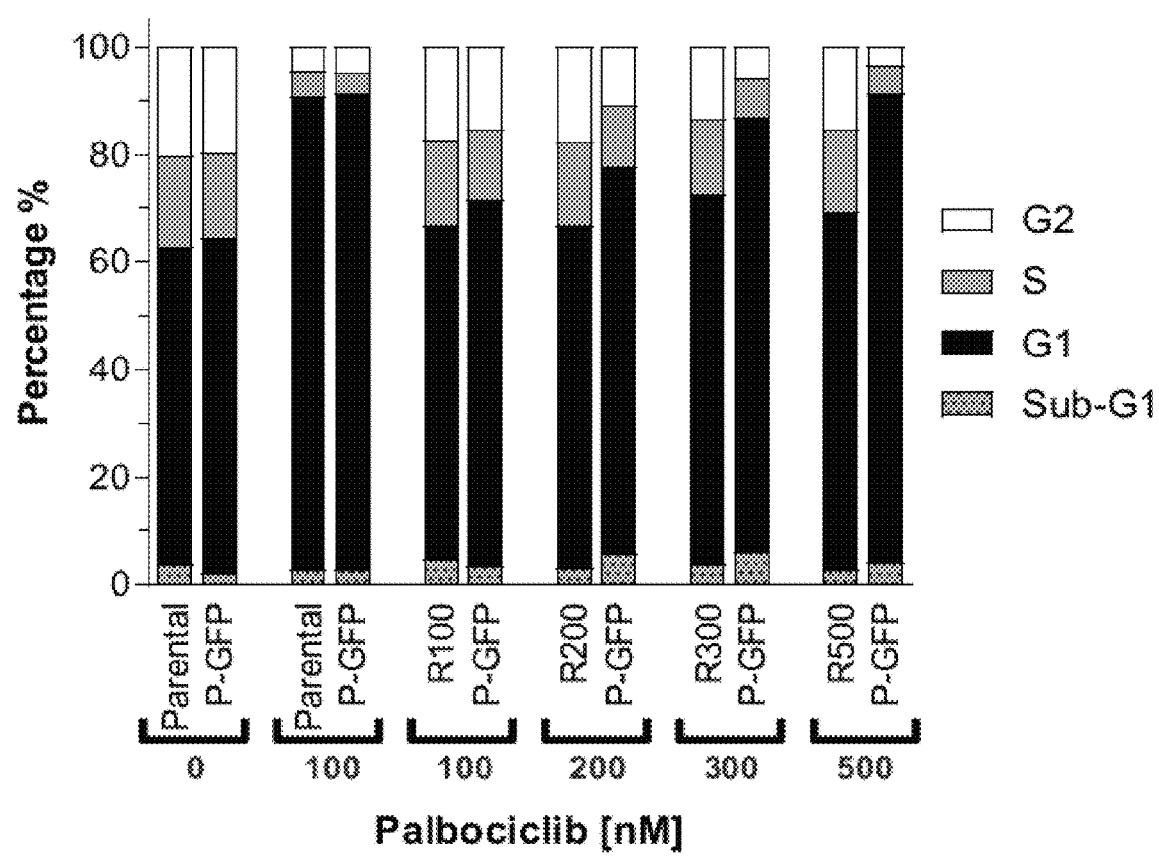

Example 5: CDK4/6 Inhibitor Resistance is Mediated by Extracellular Signaling While generating resistant lines, it was observed that the population of cells appeared to overcome CDK4/6 inhibition as a whole, rather than forming distinct colonies of resistant cells. This phenomenon suggested that resistance was being mediated by extracellular factors. To test this hypothesis, a GFP-expressing parental was combined with non-fluorescent T47D cells, either parental or resistant, in the presence or absence of palbociclib. When parental cells were mixed together, they behaved as expected, displaying a normal cell cycle distribution when untreated, and G1 arrest with CDK4/6 inhibition. In contrast, the co-culture of GFP-expressing parental cells and non-fluorescent resistant cells for 48 hours led to a resistant phenotype in the GFP-expressing parental cells, demonstrated by the lack of cell cycle arrest after 100 nM palbociclib treatment (FIG. 4A). Quantification of DNA content demonstrated that co-culture of resistant cells with GFP-expressing parental cells resulted in parental cells becoming resistant to 100 and 200 nM palbociclib, and acquiring slightly increased resistance to 300 nM palbociclib. However, after 48 hours of co-culturing parental and R500 T47D cells, parental cells were still sensitive to 500 nM palbociclib, and underwent G1 arrest (FIG. 4B).

Figure 4C:
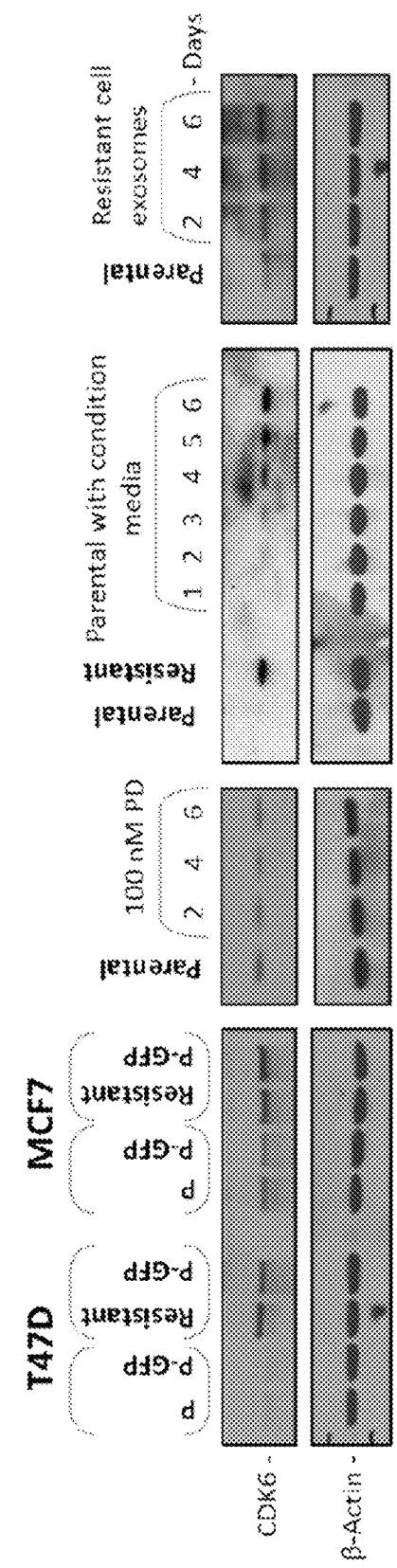

After co-culturing the cells for 48 hours, the cells were sorted based on GFP expression and performed western blot analysis. Parental T47D or MCF7 cells that had been co-cultured with resistant cells gained substantial CDK6 expression, comparable to that of resistant cells (FIG. 4C, first panel). This increase was not simply due to drug treatment, since prolonged palbociclib exposure up to 6 days had no observable effect on CDK6 expression (FIG. 4C, second panel). Growing parental T47D cells in resistant cell-conditioned media also caused a marked increase in CDK6 expression over a 6-day time period (FIG. 4C, third panel). Finally, treating parental T47D cells with purified exosomes from the media of resistant cells was also able to elicit a similar increase in CDK6 protein expression (FIG. 4C, fourth panel).

Figure 11A:
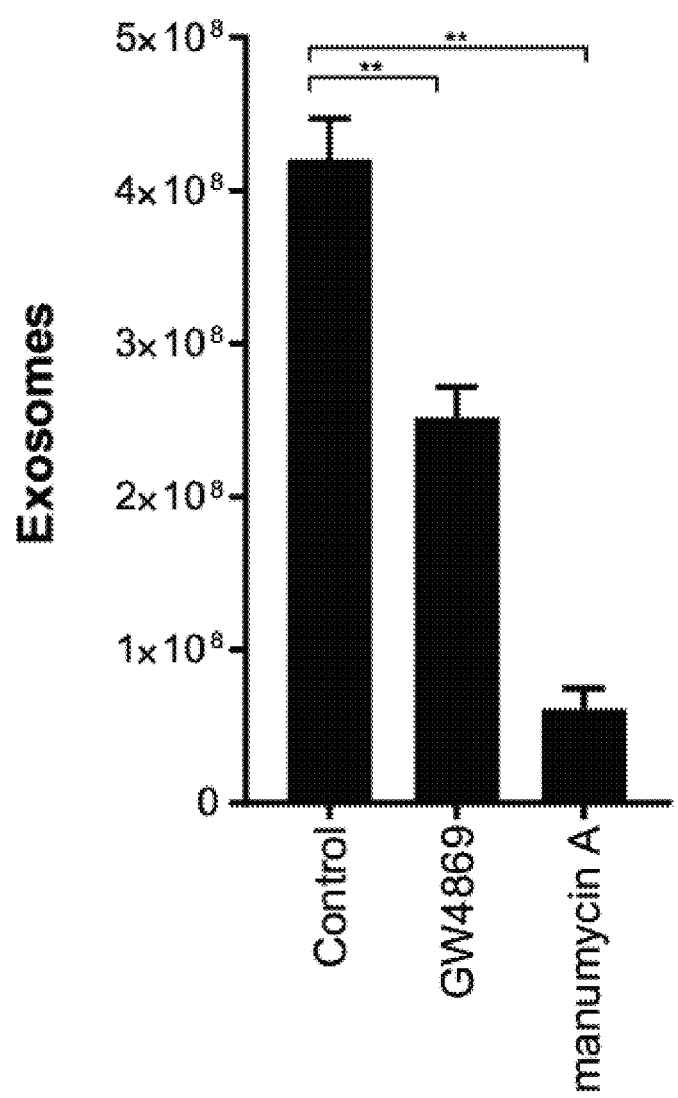
FIG. 11A-FIG. 11B is a series of bar graphs showing that inhibition of exosome production reduces efficacy of resistance transmission from resistance to parental cells.
Figure 11B:
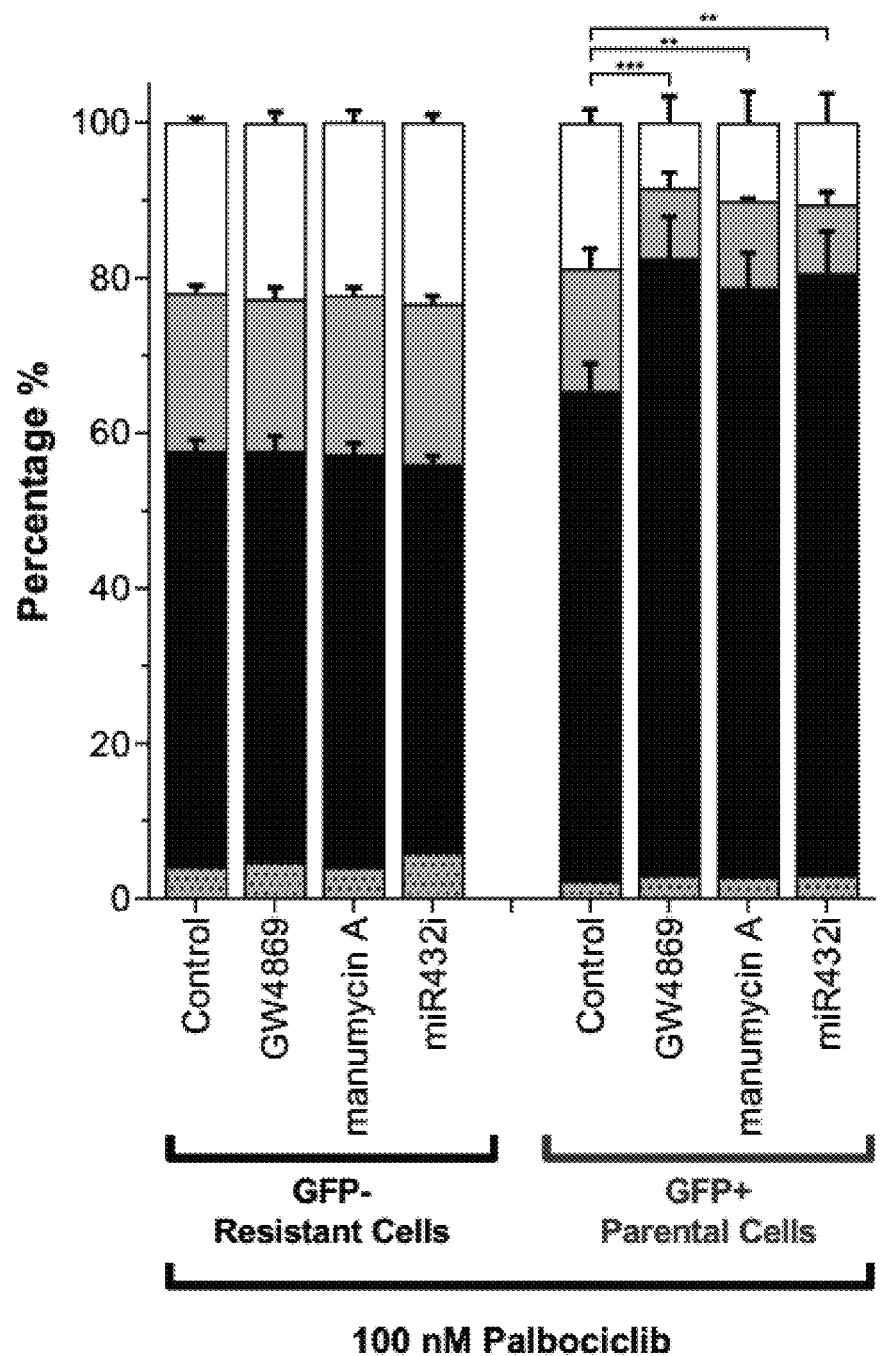

To further confirm the role of exosomes in resistance transmission, the GFP-co-culture assay was repeated while inhibiting exosome production using manumycin A or GW4869 (FIG. 11A). Both manumycin A and GW4869 treatment resulted in a significant increase in G1 population of GFP-positive parental T47D cells, indicating perturbation of resistance transmission by inhibiting exosome biogenesis (FIG. 11B).

Figure 4D:
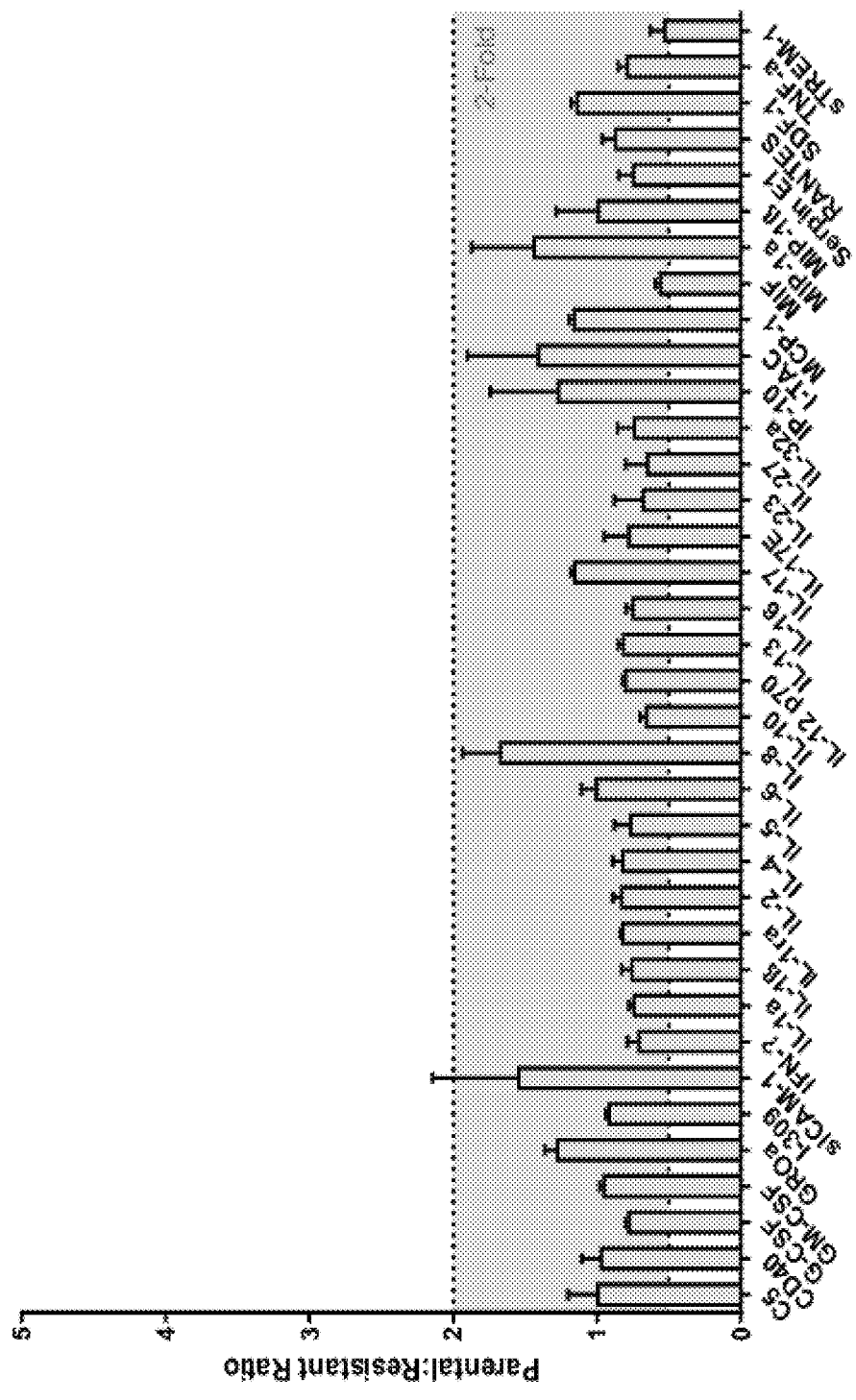

The excretion of numerous extracellular signaling cytokines were compared; there were no changes greater than 2-fold in resistant compared with parental T47D cells (FIG. 4D). Overall, these results indicate that exosome miRNAs are differentially expressed in resistant cells. CDK 6 resistance is mediated by extracellular signaling via miRNA regulated CDK 6 inhibitor resistance. Furthermore, overexpression of miR-432-5p confers aCDK4/6 inhibitor resistant phenotype. Thus, exosomal miR-432-5p mediates CDK4/6 inhibitor resistance. Also, increased CDK6 and resistance is conferred by co-culture, and media or exosome transfer. Thus, exosomal miR-432-5p mediates CDK4/6 inhibitor resistance.

Example 6: Exosomal miR-432-5p Mediates CDK4/6 Inhibitor Resistance

Figure 5A:
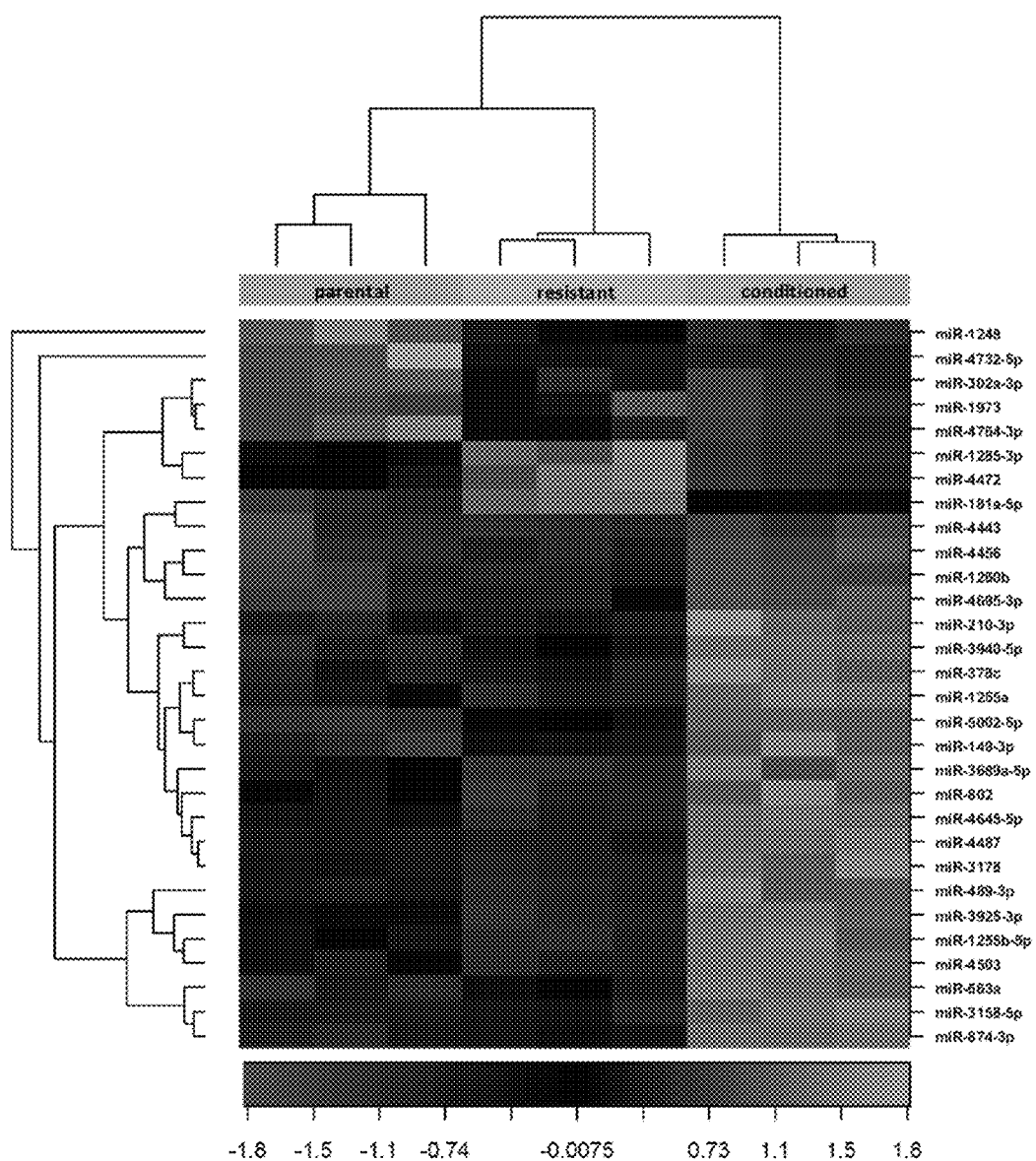

Next, the miRNA profile of parental and resistant T47D cells was examined, as well as parental cells grown in media conditioned by resistant cells. Palbociclib-resistant cells and parental cells grown in resistant cell conditioned media shared a more similar expression profile compared to that than of parental cells (FIG. 5A). Numerous miRNAs were differentially expressed to a significant degree when comparing parental and resistant cells. miRNA target prediction algorithms revealed that 8 miRNAs that were significantly downregulated and 2 that were upregulated in resistant cells were predicted to bind CDK6 mRNA (FIG. 5B). Overall, these results indicate that numerous exosomal miRNAs are significantly up/downregulated in resistant cells.

Figure 5C:
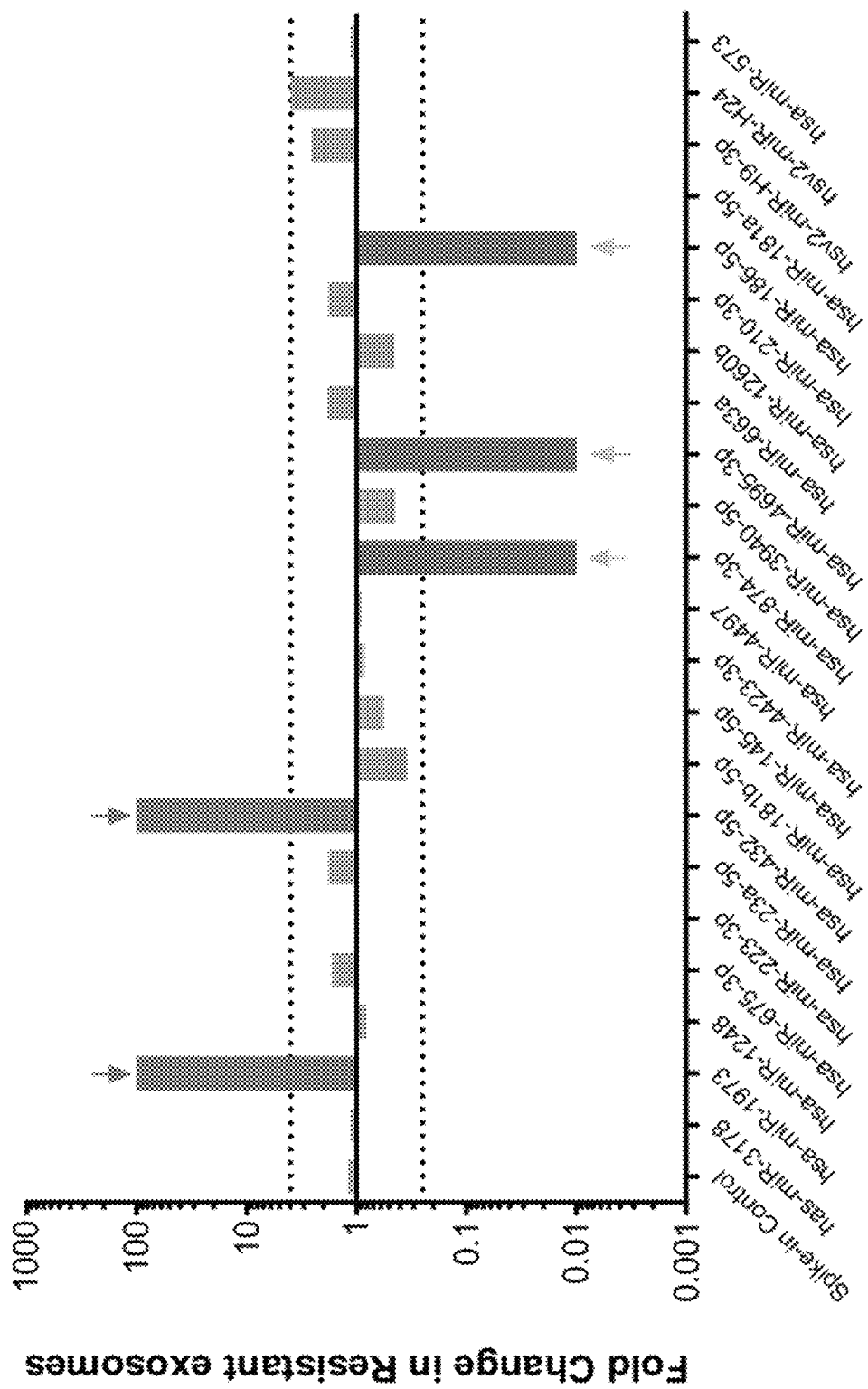
Figure 5D:
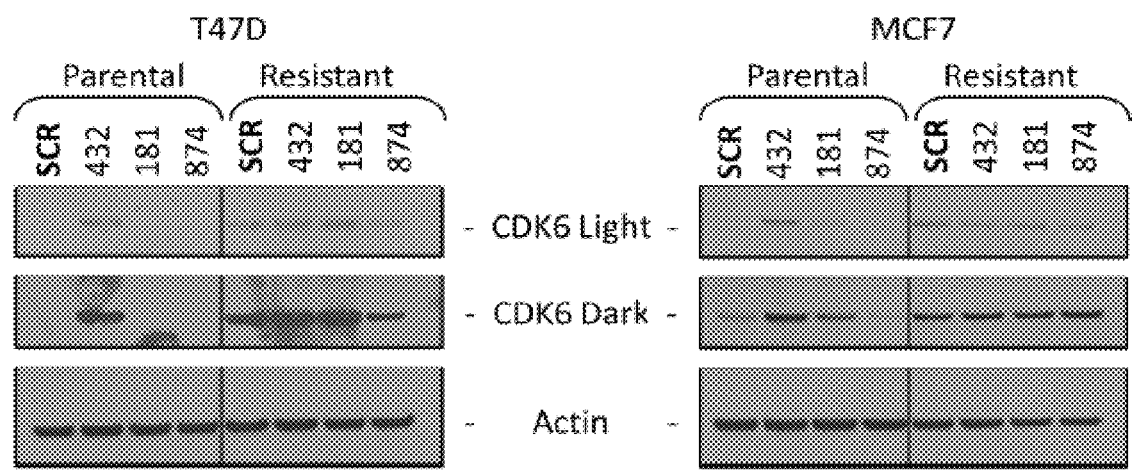

Analysis of differentially expressed miRNAs in the purified exosomes of parental and resistant T47D cells revealed a greater than 100-fold difference in 5 miRNAs: miR-1973, miR-432-5p, miR-874-3p, miR-4695-3p and miR-186-5p, three of which were decreased and predicted to target CDK6 mRNA (FIG. 5C). To determine if these miRNAs were involved in increased CDK6 expression and palbociclib resistance, an aim was to stably express each miRNA in both parental and resistant T47D and MCF7 cells. Unfortunately, plasmid-driven expression of miR-1973, 4695-3p and 186-5p was unsuccessful, so a decision to overexpress miR-181a-5p was made, as it was the most significantly increased miRNA in resistant cells (FIG. 5B), as well as mir-432-5p and miR-874-3p. miR-432-5p-overexpressing T47D and MCF7 cells both had markedly increased CDK6 protein expression. The overexpression of miR-874-3p produced inconsistent results, with a marked decrease in CDK6 protein in resistant T47D and parental MCF7 cells, and with no effect in resistant MCF7 cells (FIG. 5D).

Figure 5E:
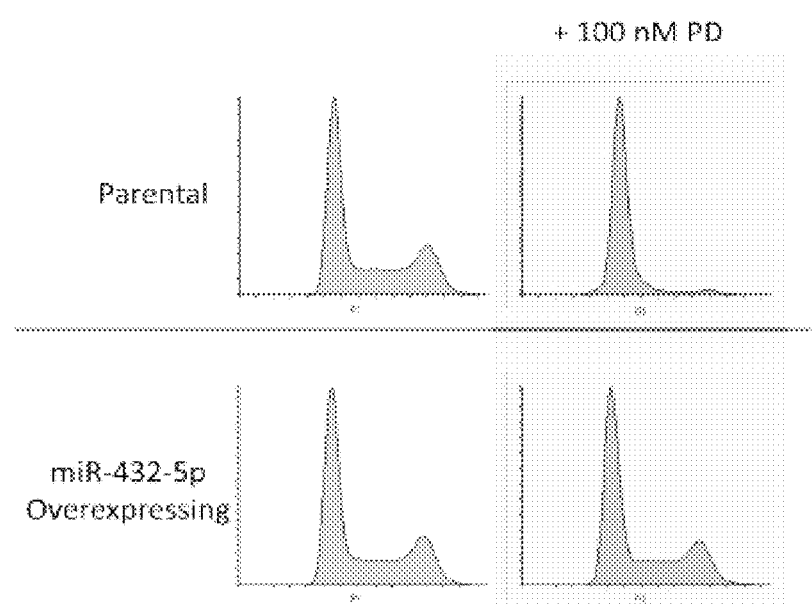
Figure 5F:
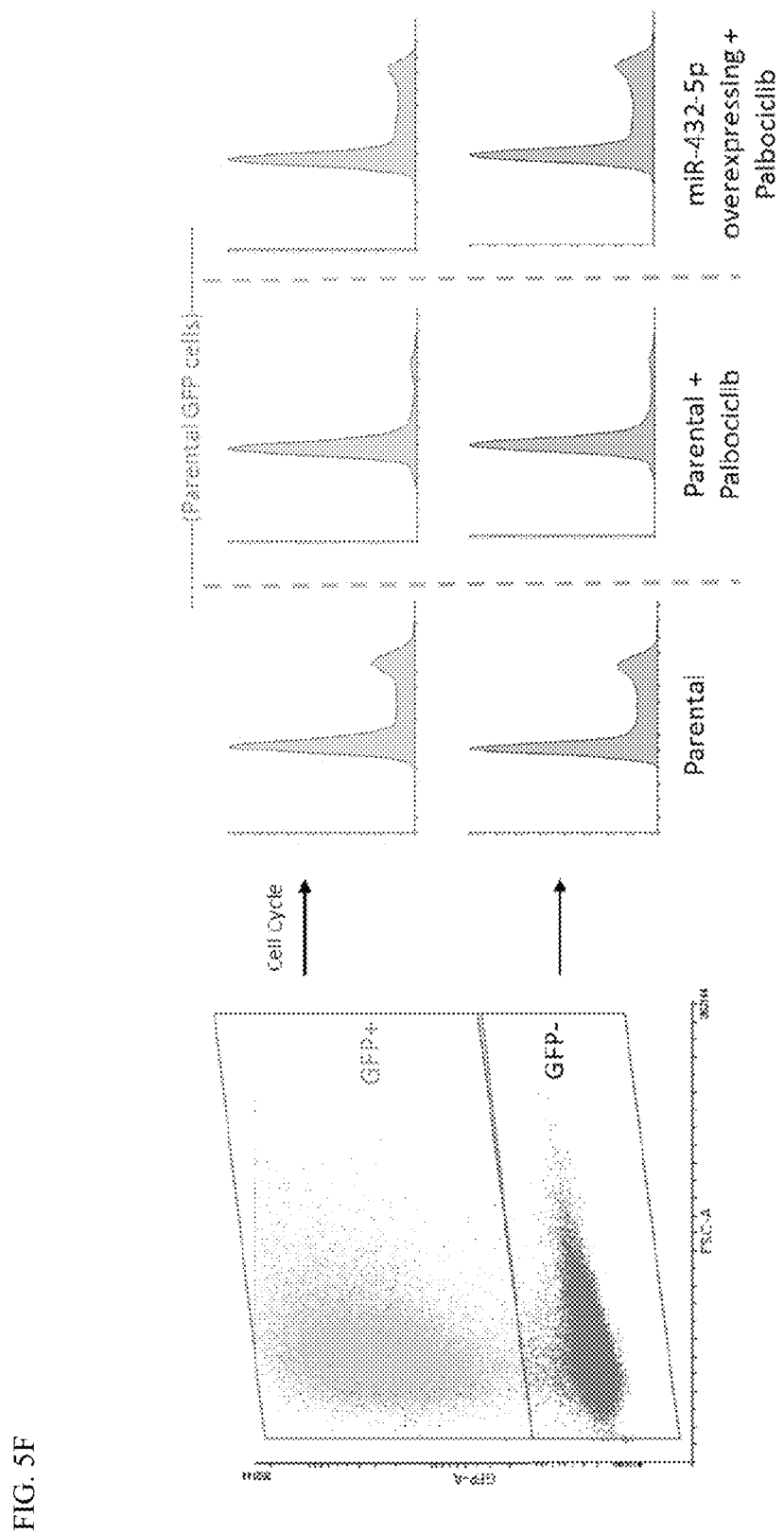
Figure 5G:
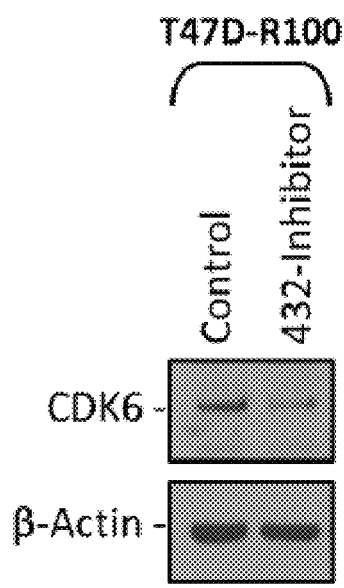
Figure 5H:
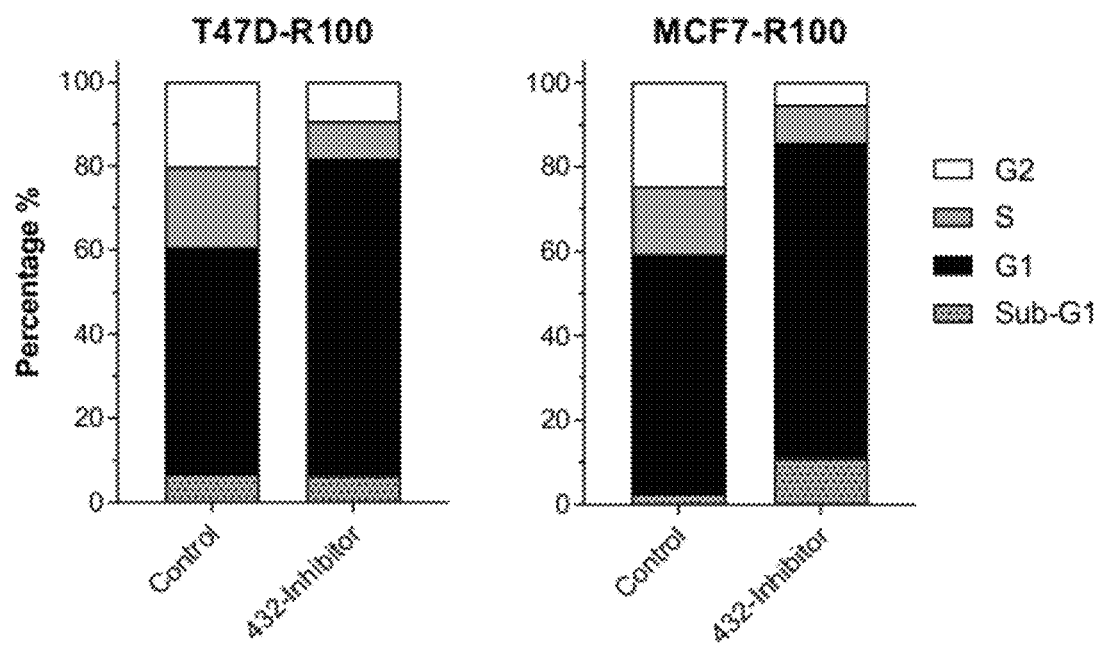
Figure 5I:
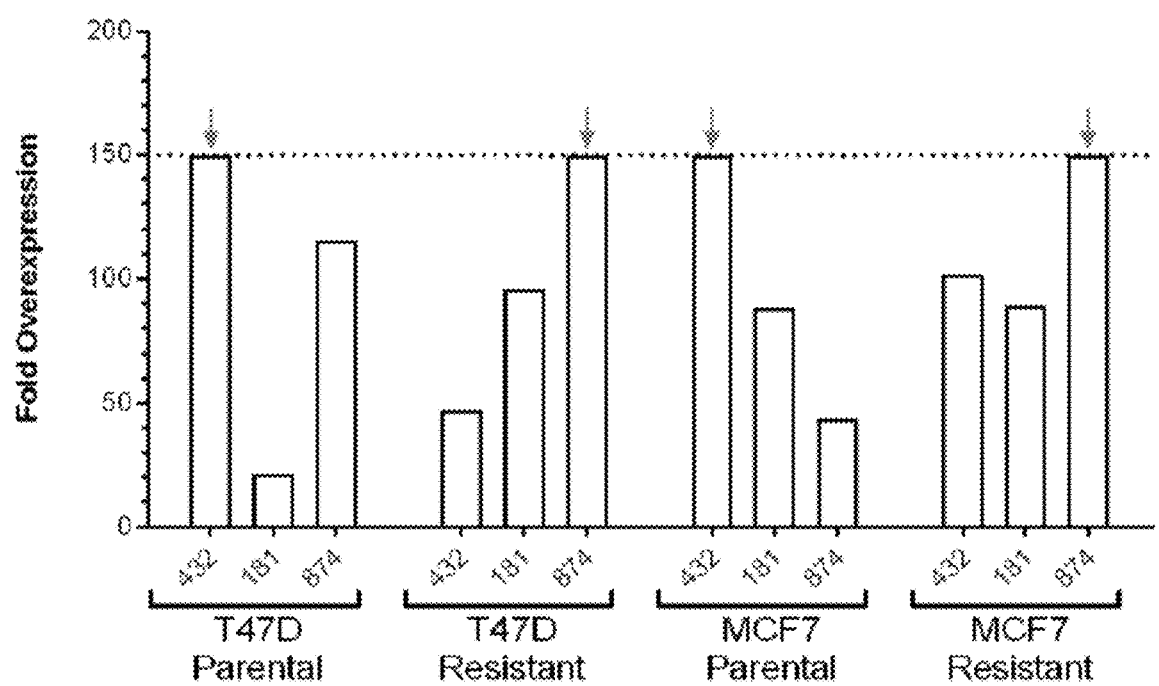

As it seemed most likely that transmissible resistance was driven by increased expression of a miRNA, rather than decreased expression, miR-432-5p was primarily focused upon. Parental cells overexpressing miR-432 behaved much like resistant cells, i.e. they did not arrest to 100 nM palbociclib (FIG. 5E) had a significantly increased palbociclib and ribociclib $GI_{50}$ (FIG. 10A and FIG. 10B) and could confer resistance in parental cells by co-culture (FIG. 5F). Furthermore, when resistant T47D cells were transfected with an miRNA-432-5p inhibitor, CDK6 levels decreased and G1 arrest increased (FIG. 5G and FIG. 5H). This indicates inhibition of miR-432-5p resistant cells to CDK4/6 inhibition by reducing CDK6.

Figure 6A:
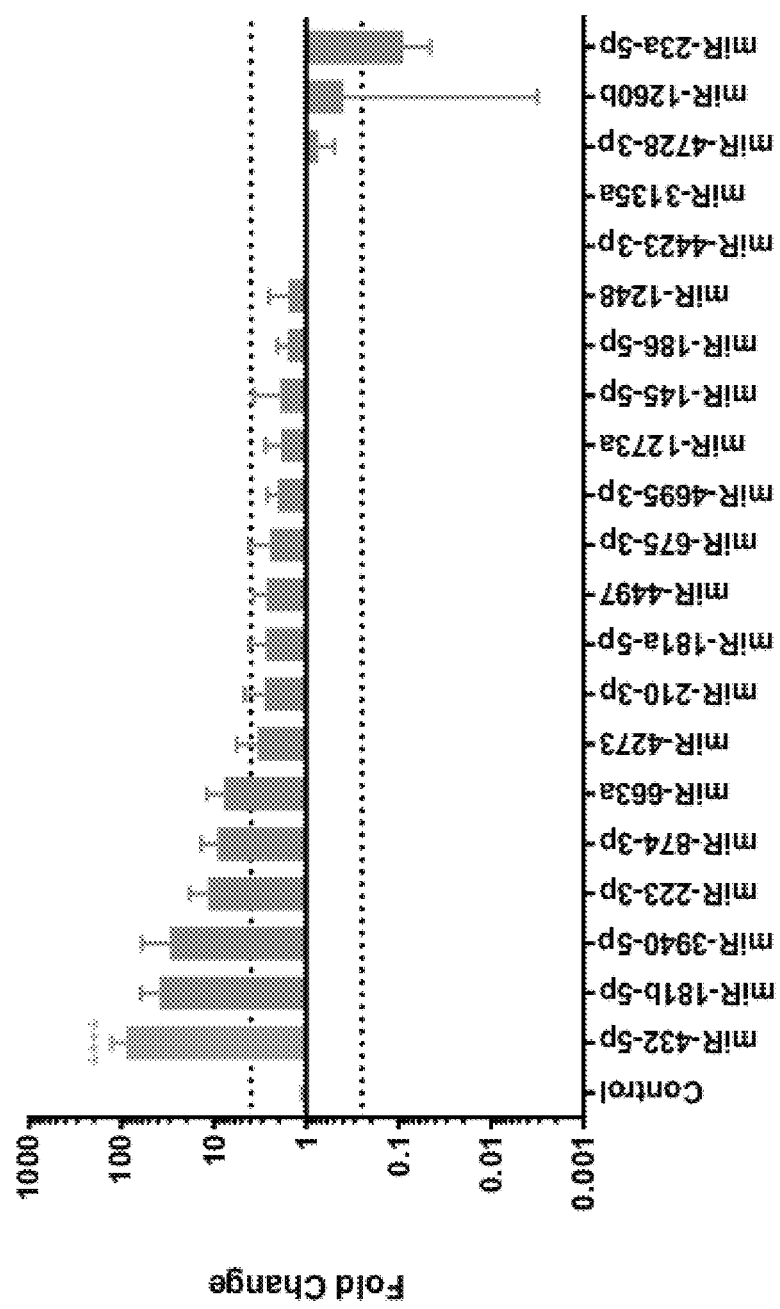

Example 7: miR-432-5p is Highly Expressed in a Post-Progression Biopsy from a Patient Treated with CDK4/6 Inhibition Next, pre-treatment and post-progression biopsies were analyzed from a patient with parotid cancer harboring CDKN2A/B loss who had achieved a partial response to the CDK4/6 inhibitor ribociclib (Infante, J. R. et al., Clin. Cancer Res 22: 5696-5705 (2016)). The post-progression biopsy had a significant increase in several of the previously investigated miRNAs. Most notably, miR-432-5p expression was significantly higher ($p<0.0001$) with an 88-fold increase relative to the pre-treatment biopsy (FIG. 6A). This indicates miR-432-5p expression is significantly increased in post-treatment biopsy from a patient treated with CDK4/6 inhibition.

Figure 6B:
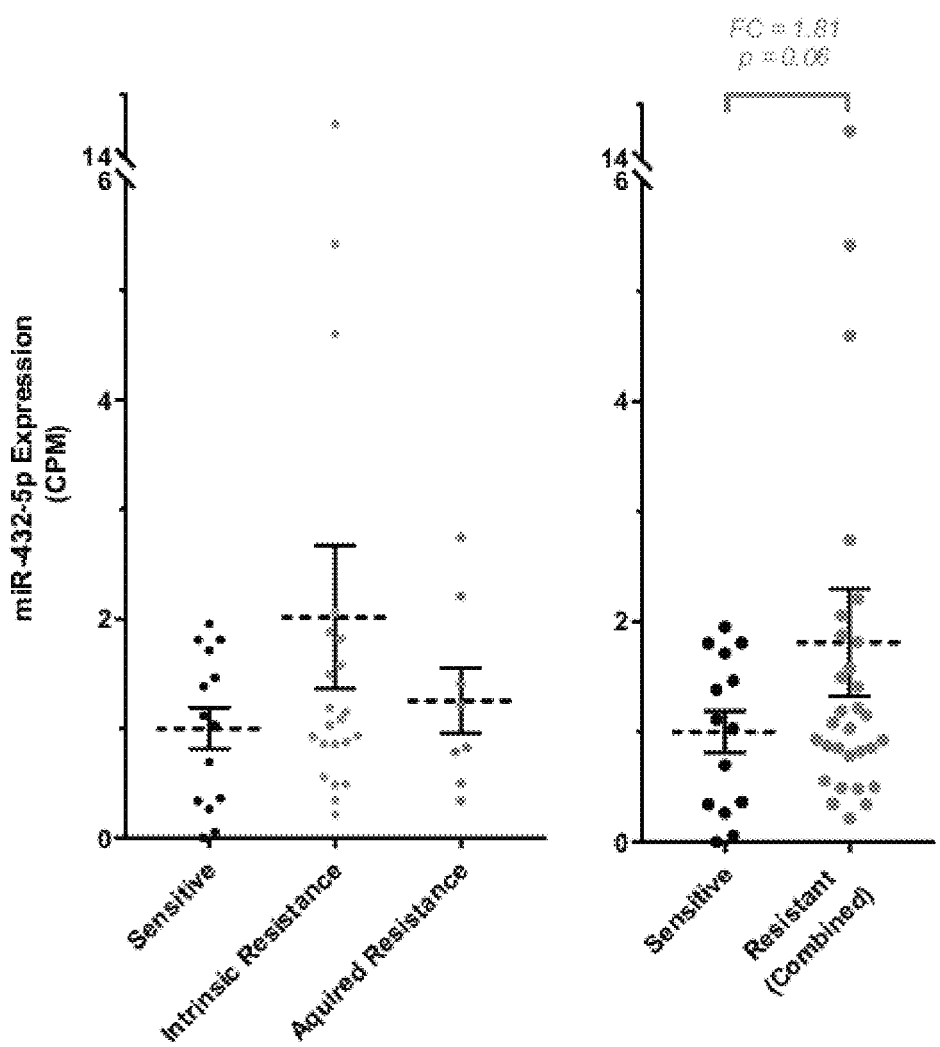

As described herein, miR-432-5p expression is higher in biopsies from ER+ breast cancer patients with intrinsic or acquired resistance compared to those from patients with sensitive disease. In addition to the paired samples from the parotid cancer patient, miRNAseq was utilized to analyze 44 tumor biopsies from patients who received CDK4/6 inhibitor treatment either with hormonal therapy or as monotherapy for metastatic ER+, HER2-negative breast cancer. Biopsies obtained prior to treatment were phenotypically stratified based on response to CDK4/6 inhibitor treatment as either sensitive or intrinsically resistant, while those obtained post-progression were defined as having acquired resistance (Wander, et al., 2018 ASCO abstract). There was increased mean miR-432-5p expression in both intrinsic and acquired resistance tumor samples compared to sensitive samples. When comparing all resistant (intrinsic and acquired) vs. sensitive tumors, there was a >1.8-fold increase in mean miR-432-5p expression among resistant tumors (FIG. 6B). Of note, two samples with intrinsic resistance and RB1 loss had levels of miR-432-5p below the mean identified in sensitive cells.

Figure 6E:
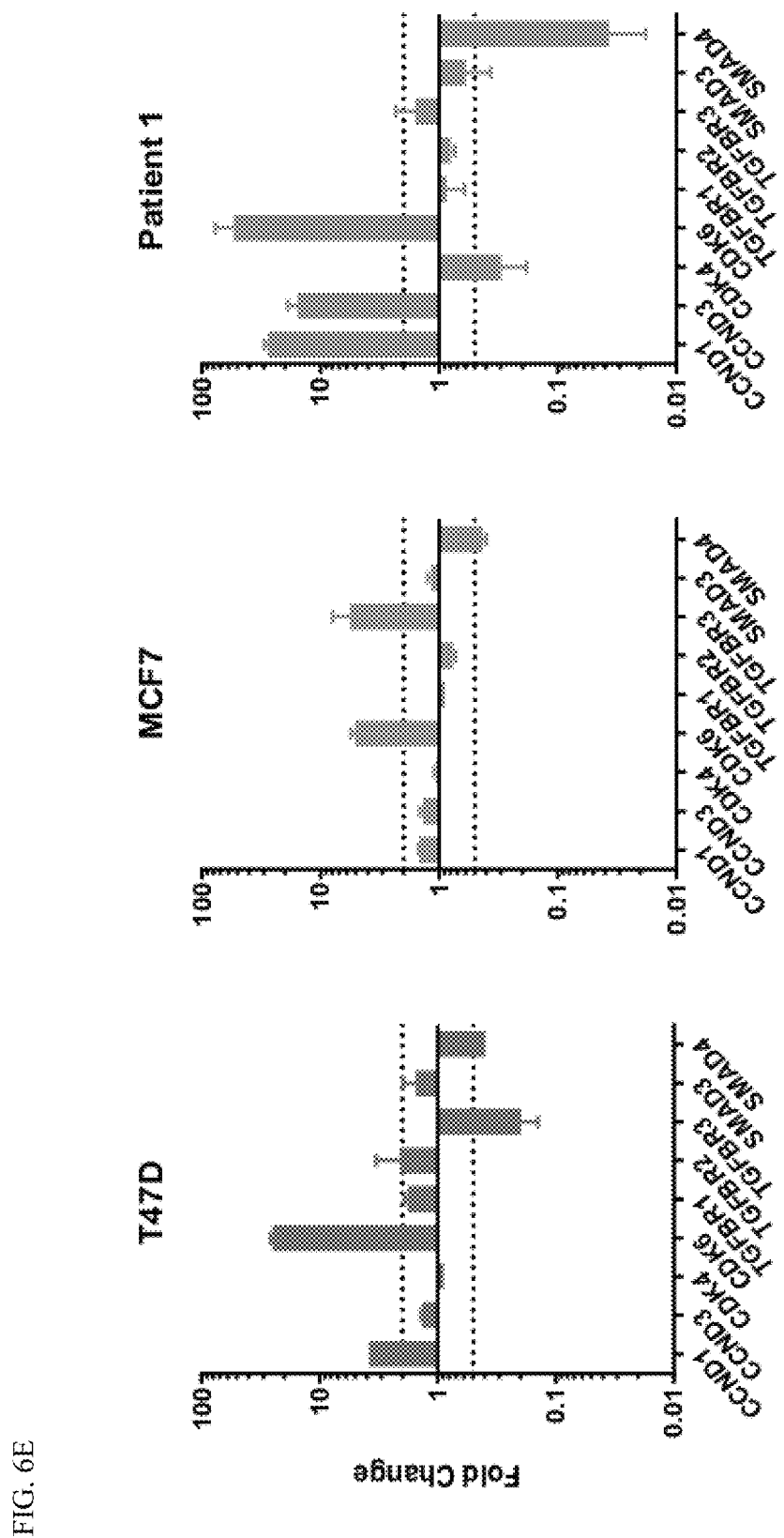
Figure 6F:
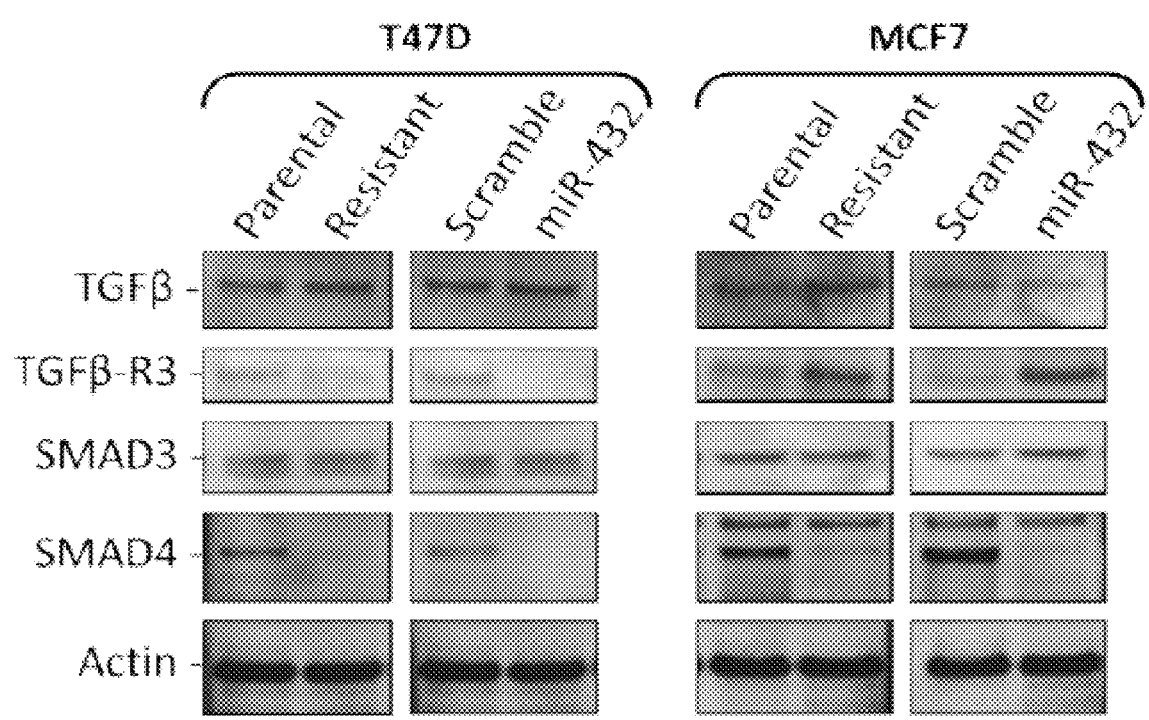
Figure 6G:
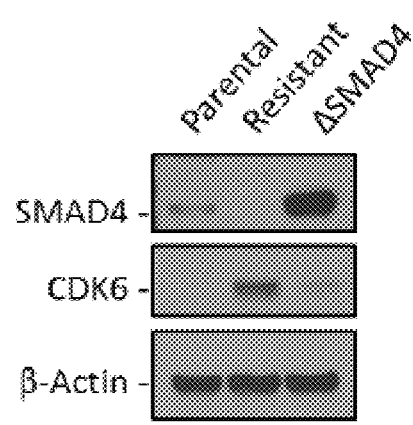
Figure 6H:
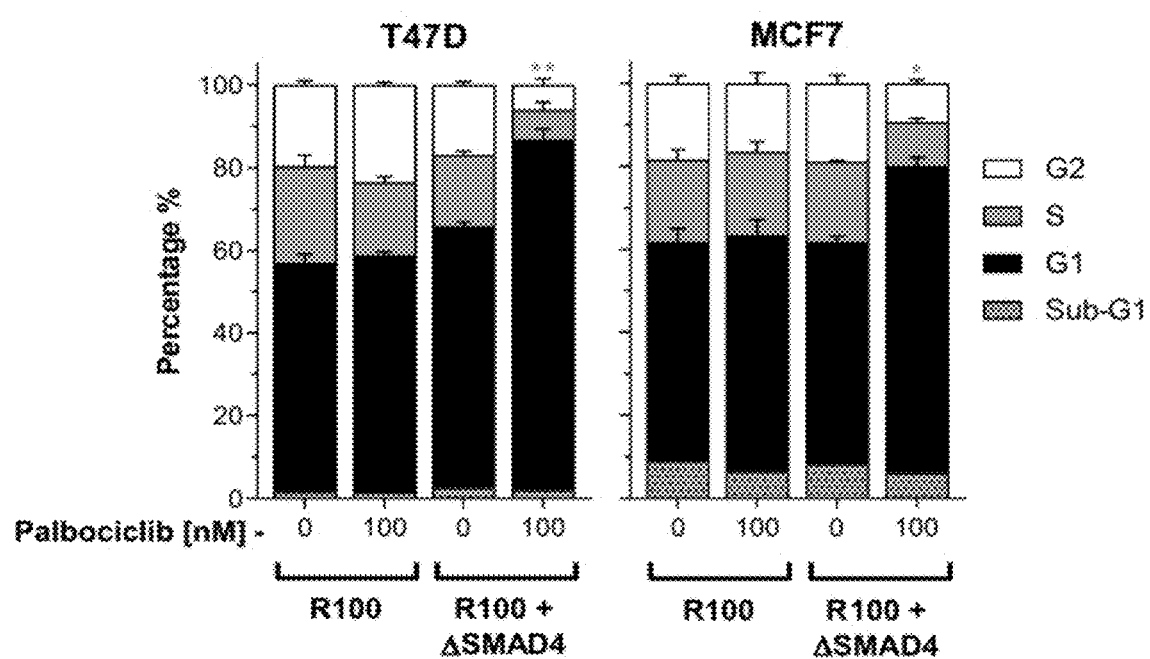

Example 8: miR-432-5p Increases CDK6 Protein Expression by Targeting the TGF-β Pathway To determine the target of miR-432-5p miRNA:mRNA pulldown was performed. Pathway analysis of the pull-down mRNAs revealed numerous genes of the TGF-β pathway to be significantly enriched. Comparison between miRNA:mRNA pulldown and gene expression analysis revealed two genes, TGFBR3 and SMAD4, which were both enriched by pulldown and downregulated in resistant T47D cells (FIG. 6D). Using target prediction algorithms, miR-432-5p was significantly predicted to bind the 3'UTR of both TGFBR3 and SMAD4 (FIG. 6C). To correlate these data with resistant cells and the patient biopsies, the mRNA expression of genes involved in the cell cycle and TGF-β pathway were analyzed by quantitative real-time PCR, and calculated the fold change in resistant vs. parental cells, and post- vs. pre-treatment biopsies. Both resistant cell lines, as well as the post-treatment patient biopsy, demonstrated a significant decrease in SMAD4 mRNA expression that was accompanied by increased CDK6 expression (FIG. 6E). These data were confirmed by western blot. Both T47D and MCF7 palbociclib-resistant and miR-432-5p-overexpressing cells had markedly lower SMAD4 protein expression than parental cells (FIG. 6F). To further confirm that lowered SMAD4 level was a critical component of palbociclib-resistance, SMAD4 was overexpressed in resistant cells; this resulted in decreased CDK6 expression (FIG. 6G), and importantly, restored susceptibility to CDK4/6 inhibitor-mediated cell cycle arrest (FIG. 6H). Overall, these results indicate that miR-432-5p targets the TGF-β pathway via SMAD4 and mediates resistance via downregulation of TGF-β signaling. These results also indicate that CDK6 is significantly increased while SMAD4 is decreased in resistant cells and post treatment biopsy.

Figure 12A:
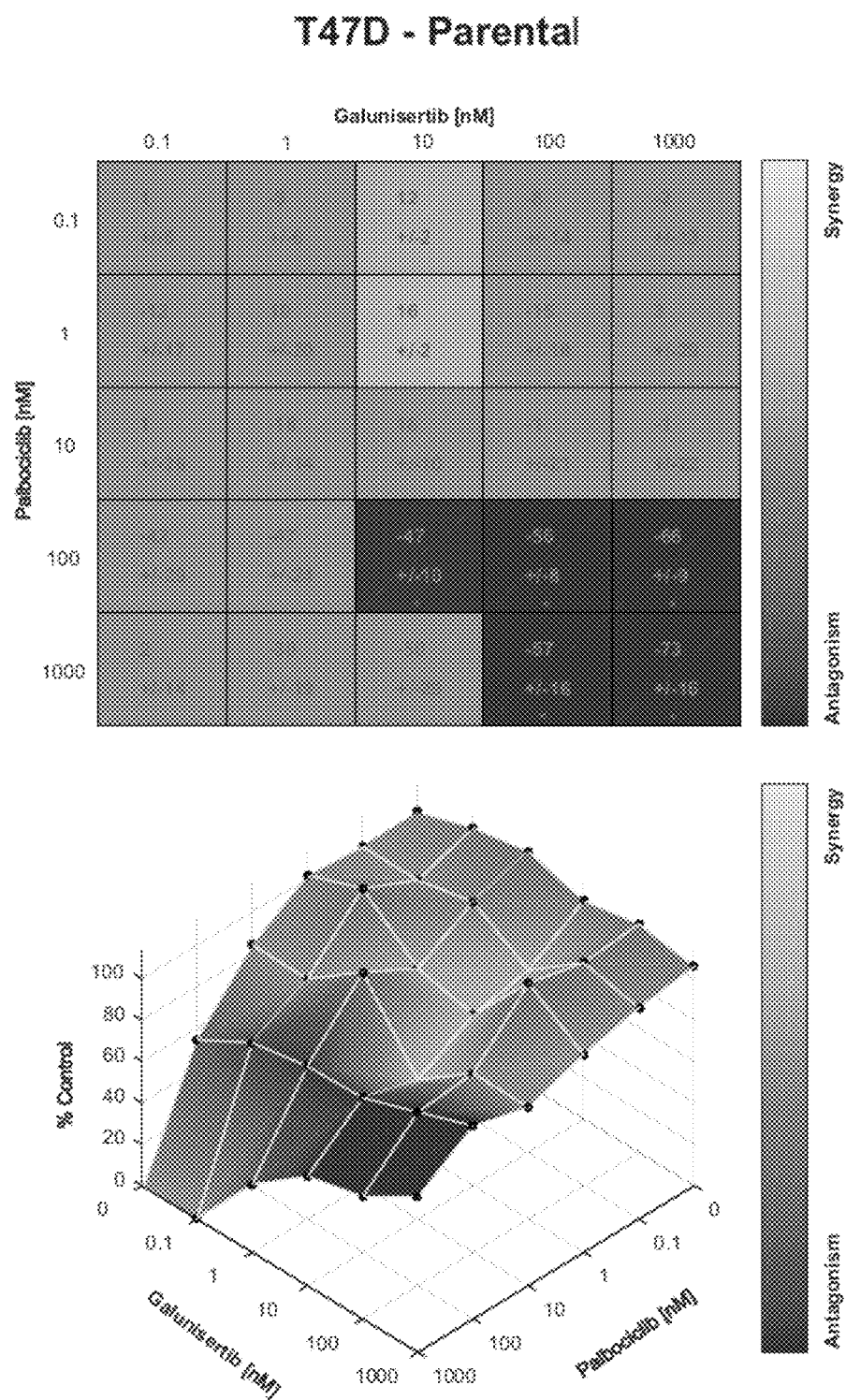
FIG. 12A-FIG. 12D is a series of graphs showing that combined galunisertib and palbociclib is antagonistic.
Figure 12B:
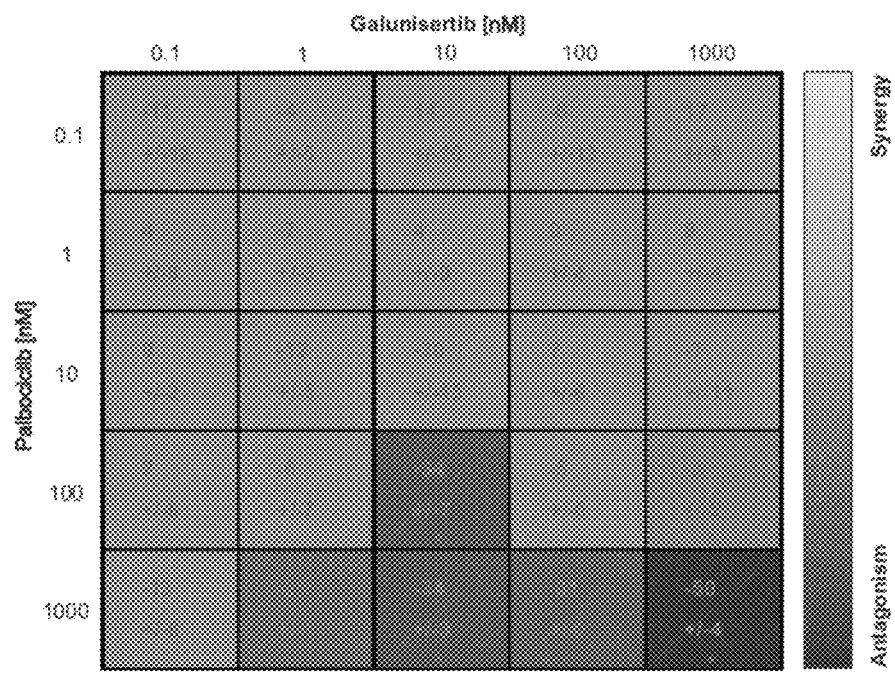
Figure 12B:
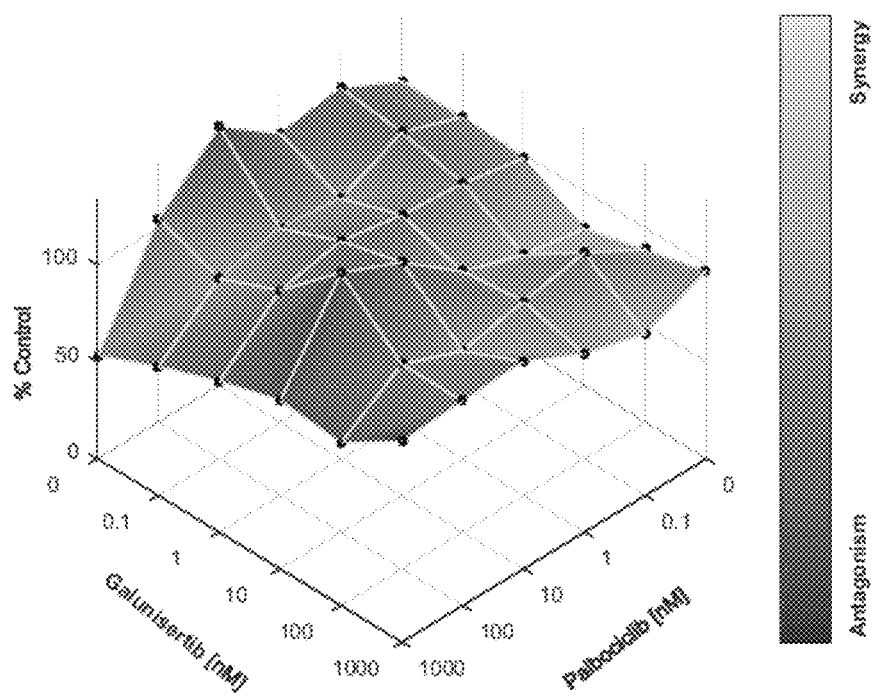
Figure 12C:
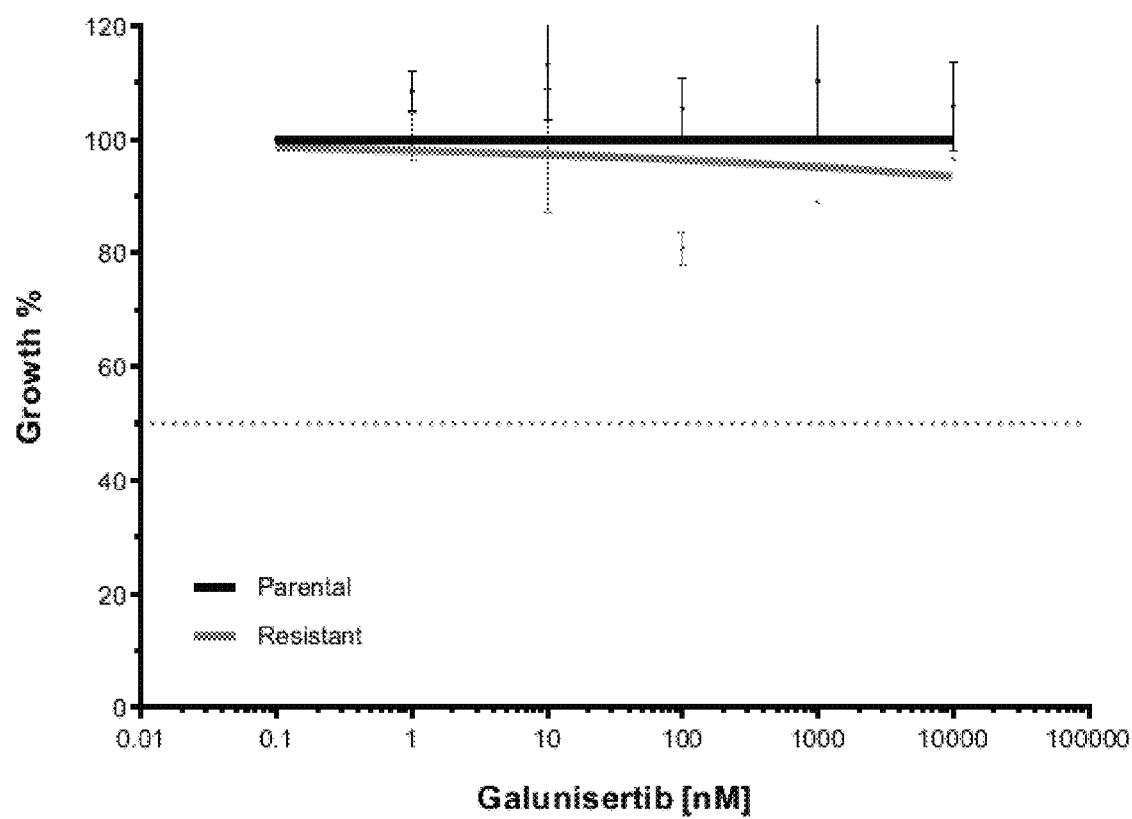
Figure 12D:
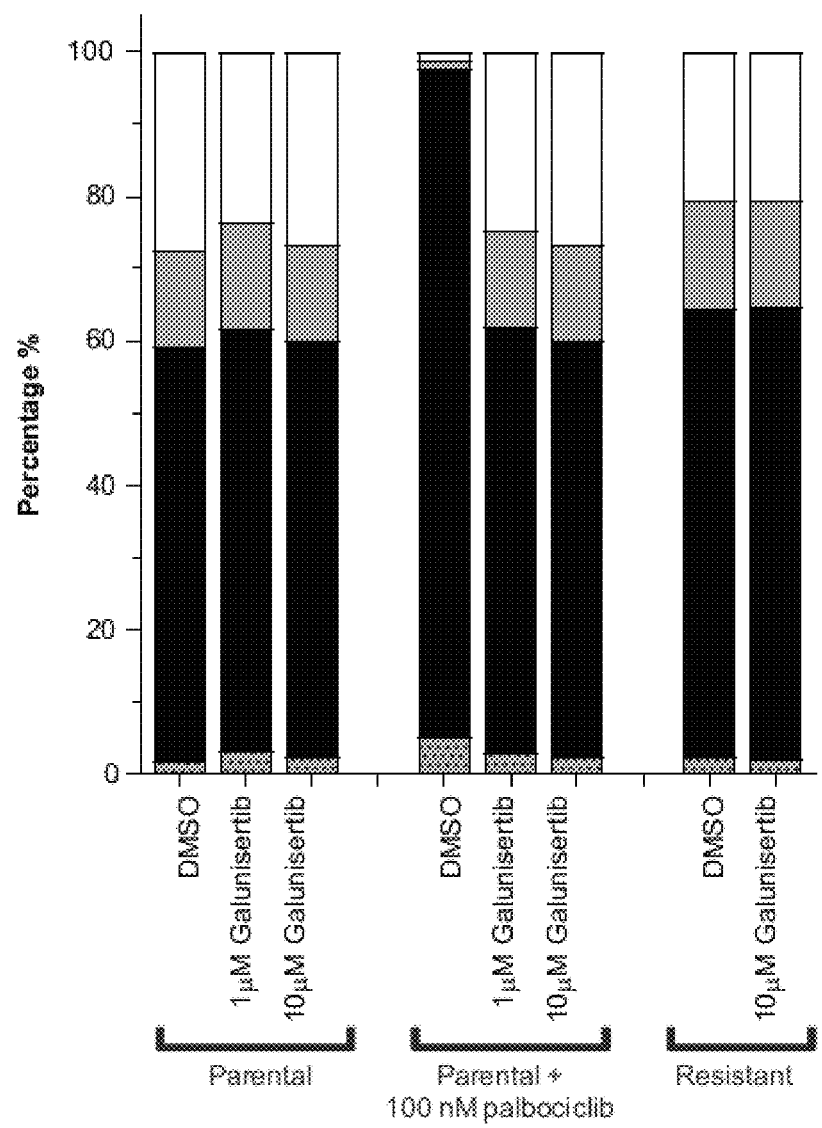

These data suggest antagonism between inhibition of the TGF-β pathway and CDK4/6 inhibition. To confirm this expectation, synergy studies were performed with the TGF-β inhibitor galunisertib and palbociclib. Increasing doses of galunisertib reduced the growth inhibitory effect of palbociclib and were significantly antagonistic in both parental and resistant T47D cells (FIG. 12A and FIG. 12B). Galunisertib treatment had no effect on the growth of parental or resistant cells when used alone (FIG. 12C); however, it did prevent G1 arrest when used in combination with palbociclib (FIG. 12D).

Example 9: Acquired Resistance is Reversed by Drug Removal

Figure 7A:
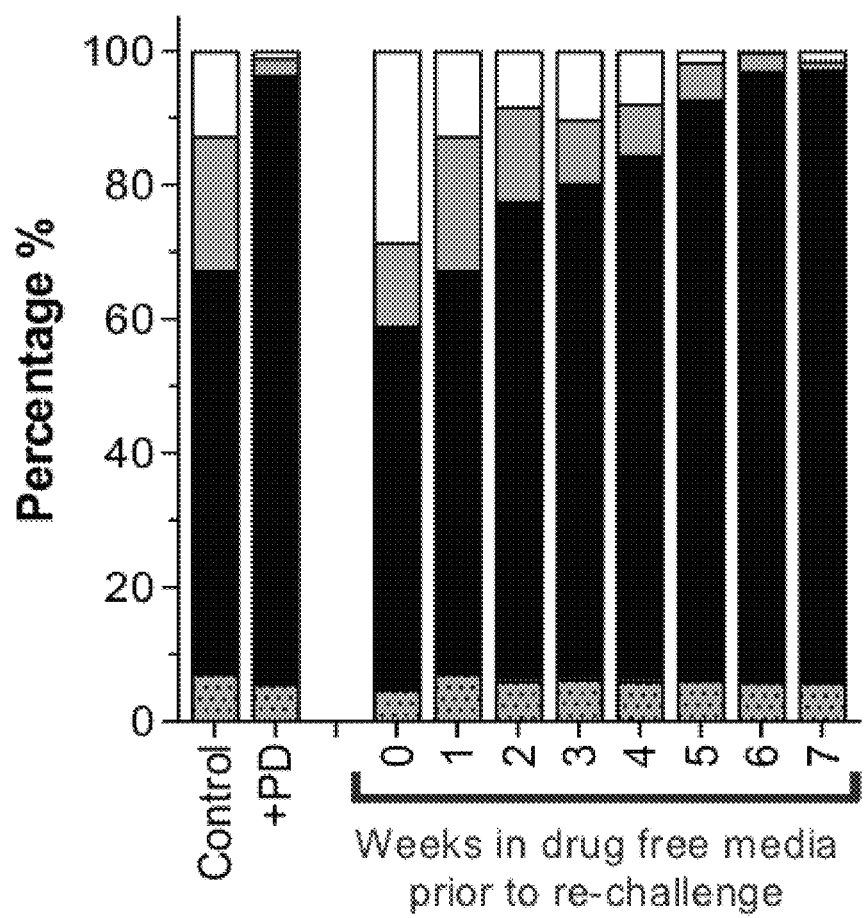
FIG. 7A-FIG. 7F are a series of graphs depicting that resistance is reversible by prolonged drug absence.
Figure 7B:
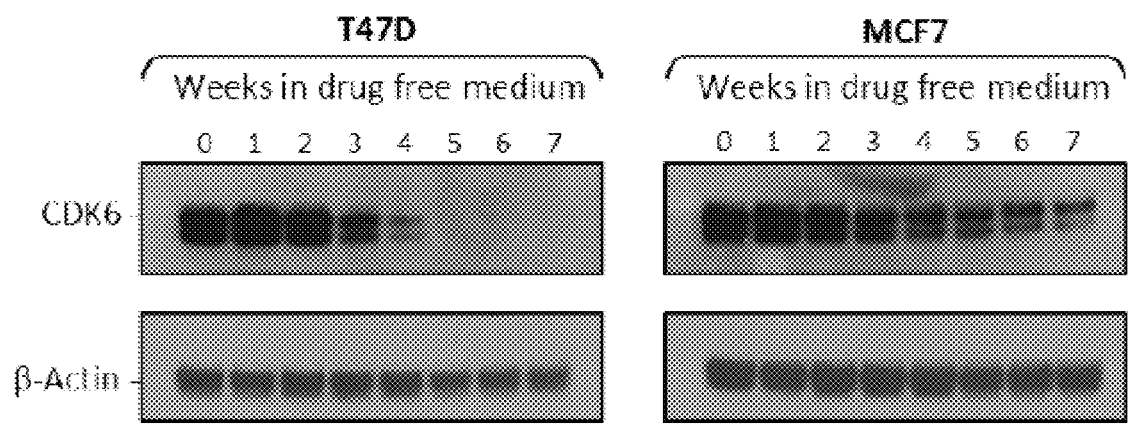

It was next determined whether the resistance acquired by this mechanism was reversible. Resistant T47D and MCF7 cells were incubated in drug-free media for up to 7 weeks, and re-challenged weekly with 100 nM palbociclib for 24 hours, followed by analysis of DNA content for cell cycle position. After 6 weeks in drug-free media, re-challenge with palbociclib resulted in a cell cycle arrest that was indistinguishable from parental cells treated with the same concentration (FIG. 7A). Analysis of resistant cells lysates via western blot revealed that removal of palbociclib caused CDK6 protein to decrease over time. In correlation with the cell cycle effects, CDK6 protein level was reduced to a level comparable to that in parental T47D or MCF7 cells after 7 weeks in drug-free media (FIG. 7B). Palbociclib-resistant cells that had been cultured in drug-free media for 7 weeks or more were labelled as "ex-resistant." The ex-resistant cells also had a significantly lower palbociclib GI50 compared to resistant cells, which was not significantly different from that of parental cells (FIG. 10A and FIG. 10B).

Figure 7C:
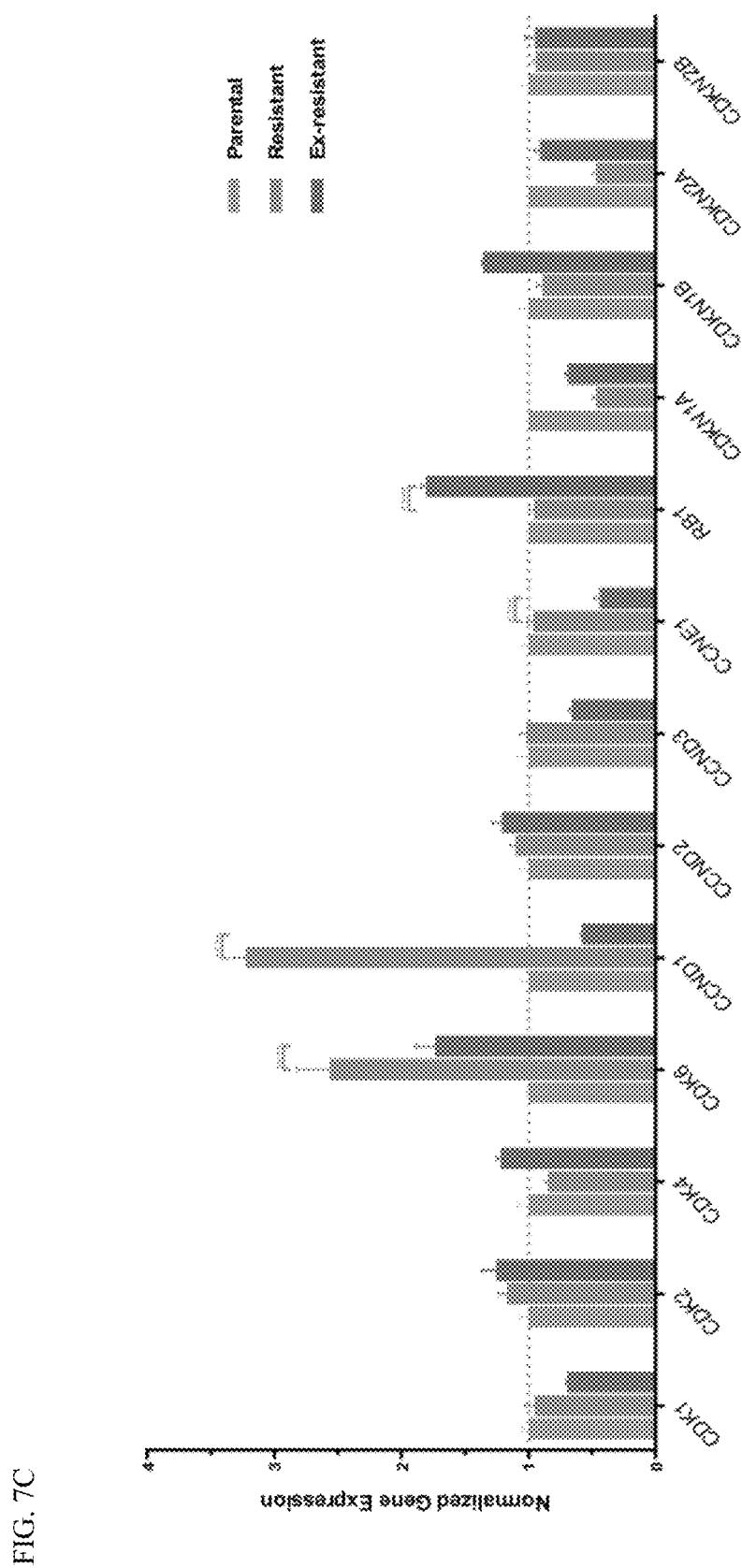
Figure 7D:
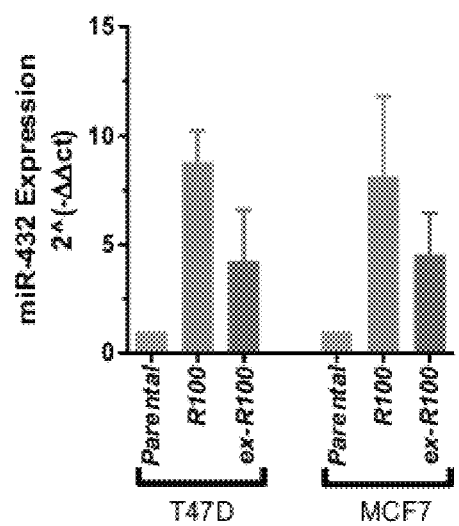
Figure 13:
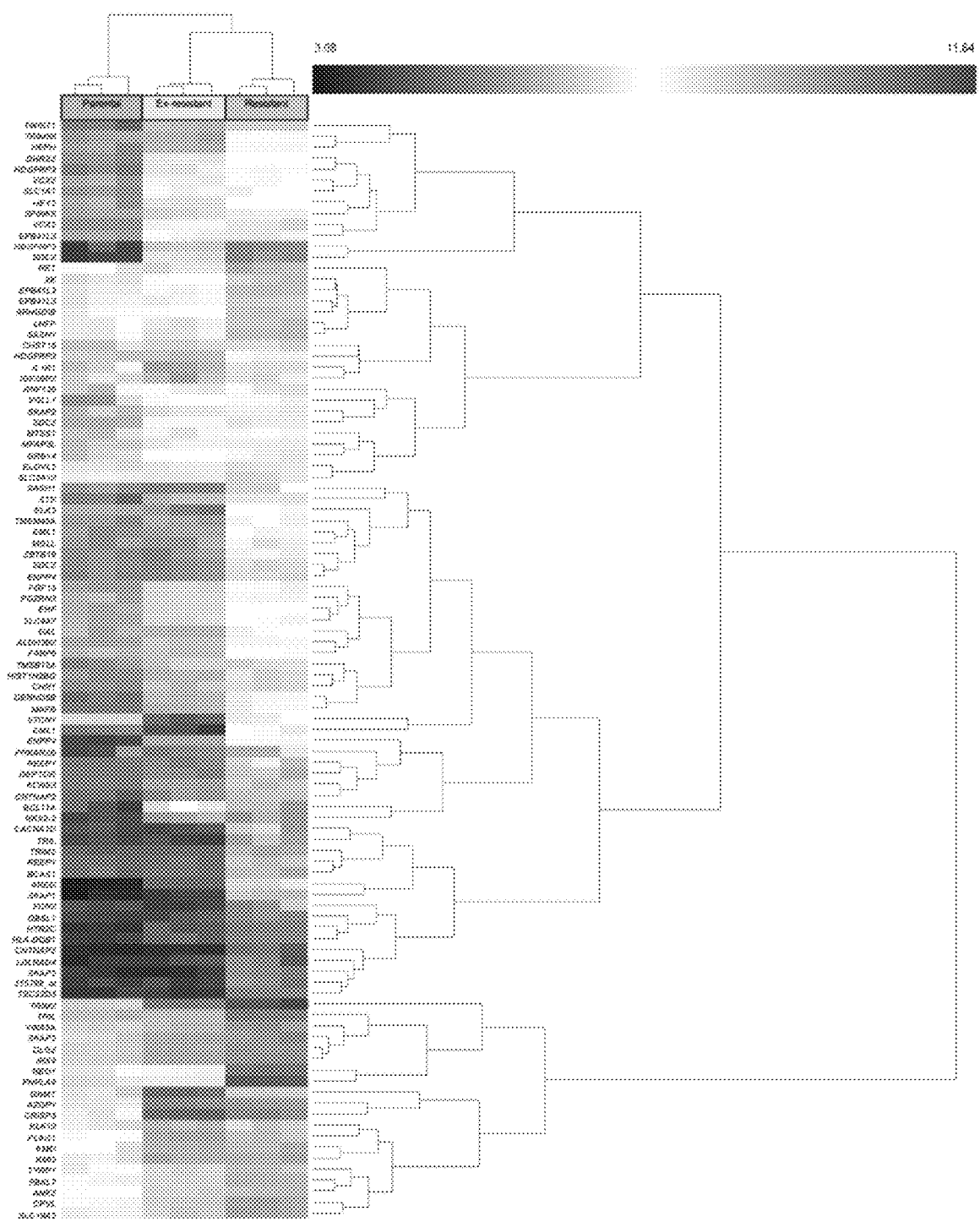
FIG. 13 is a graph showing that gene expression in ex-resistant cells is more closely related to resistant than parental cells. Shown is hierarchal clustering performed using 100 of the most significantly changed genes across parental, resistant and ex-resistant T47D cells, determined by gene expression analysis.

Analysis of gene expression in the ex-resistant cells compared to resistant and parental T47D cells revealed several significant changes. Most notably, there was a highly significant decrease in expression of CDK6, CCND1, and CCNE1 as well as a significant increase in RB1 (p<0.0001) expression in ex-resistant compared to resistant cells (FIG. 7C). Additionally, while many cell cycle related genes in ex-resistant cells returned to a similar level as present in parental cells, hierarchal clustering of 100 significantly changed genes revealed that ex-resistant cells were more closely related to resistant cells than to parental cells (FIG. 13). Additionally, the expression of miR-432-5p was analyzed in ex-resistant T47D and MCF7 cells. Relative to resistant cells, expression of the miRNA was markedly decreased, correlating with reduced CDK6 expression and the re-sensitization of these cells to palbociclib (FIG. 7D). Overall, these results indicate that CDK 4/6 inhibitor resistance is reversed by prolonged drug removal.

Figure 7E:
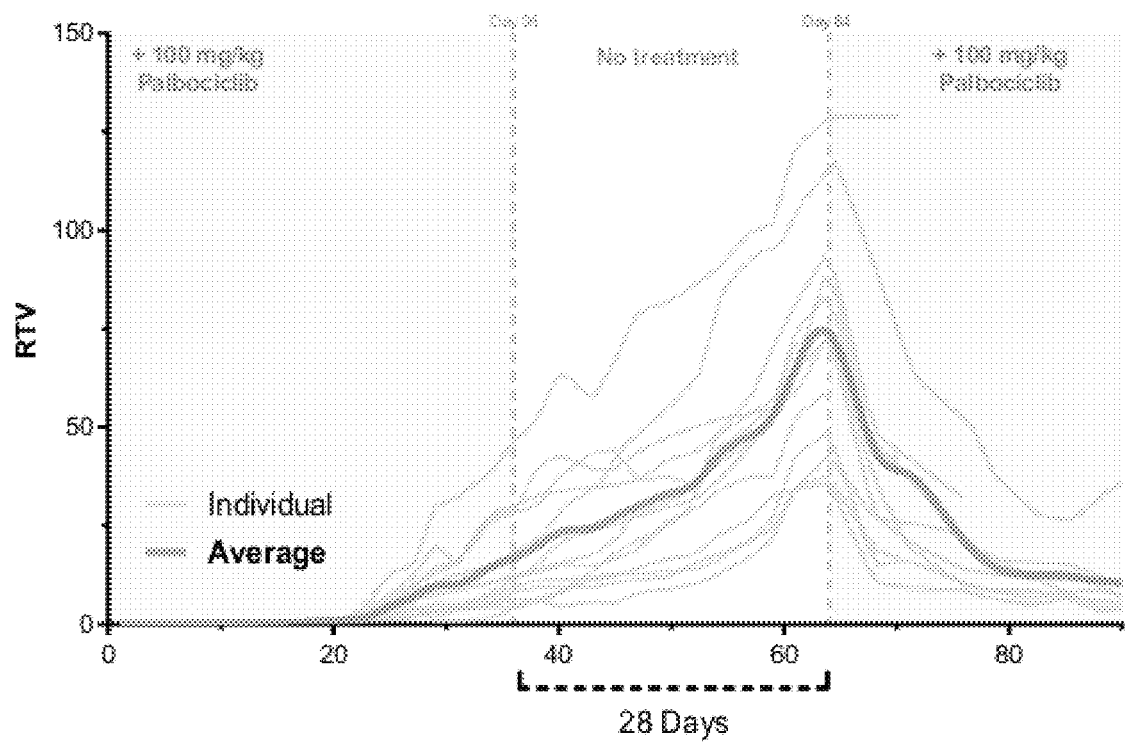
Figure 7F:
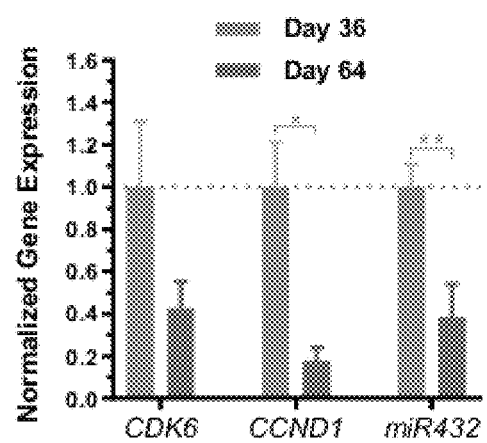

To determine whether reversible CDK4/6 inhibitor resistance could be modeled in vivo, palbociclib-resistant xenografts were established by implanting resistant MCF7 cells into mice followed by immediate palbociclib treatment. Once resistant tumors were established and growing (day 36), treatment was discontinued for the next 28 days. After this prolonged treatment holiday, treatment was re-introduced and caused a marked decrease in tumor burden in the previously palbociclib-resistant tumors (FIG. 7E). Tumor samples were collected on day 36, representative of resistant tumors on the final day of palbociclib treatment, and on day 64, representative of ex-resistant tumors prior to palbociclib reintroduction. Gene expression analysis of day 36 and day 64 tumors revealed a marked decrease in both CDK6 and CCND1 expression in day 64 tumors (ex-resistant) relative to day 36. There was also a decrease in miR-432-5p expression at day 64, which was undetectable within 50 amplification cycles of qPCR (compared to 38.7±1.52 cycles in the day 36 tumor, FIG. 7F).

Example 10: Analysis of Serum Exosomes from CDK4/6 Inhibitor Treated Patients for miR-432-5, a Potential Resistance Biomarker CDK4/6 inhibition is now part of the standard armamentarium for patients with estrogen receptor (ER)-positive breast cancer, so that understanding mechanisms of resistance is a pressing clinical issue. Here, experiments identified increased CDK6 expression as a key determinant of acquired resistance after exposure to the CDK4/6 inhibitor palbociclib in ER-positive breast cancer cells. Overexpression of CDK6 in parental cells allows consistent Rb phosphorylation in the presence of palbociclib and promotes resistance. In addition, depletion of CDK6 in palbociclib resistant cells caused resensitizsation to palbociclib and mediated growth arrest. Importantly, the experiments presented herein identified that the acquired increase of CDK6 in resistance cells is dependent on the increased expression of a specific miRNA, miR-432-5p. Overexpression of miR-432-5p in parental cells resulted in an increased CDK6 protein expression and palbociclib resistance.

As described above, using a biotin labelled miRNA-432-5p mimic, experiments were performed miRNA-mRNA capture followed RNA-seq, allowing identification of all mRNA genes targeted by miR-432-5p. Subsequent pathway analysis and correlation with gene expression data revealed downregulation of the TGF-β pathway, specifically via the SMAD4 gene. Furthermore, overexpression of SMAD4 caused decreased CDK6 expression and resensitized palbociclib resistant cells, whilst SMAD4 overexpression in parental cells conferred increased CDK6, and caused resistance. Strikingly, the experiments presented herein identified a dramatic increase in miR-432-5p in the exosome of resistant cells. Exosomal miR-432-5p expression mediated the transfer of the resistance phenotype between neighbouring cell populations, causing previously sensitive cells to acquire CDK4/6 inhibitor resistance. Experiments confirmed these data in pre-treatment and post-progression biopsies from a patient with parotid cancer harboring CDKN2A/B loss who had achieved a partial response to the CDK4/6 inhibitor ribociclib, demonstrating that this mechanism of resistance is clinically relevant.

The experiments presented herein have identified that increased expression and secretion of miR-432-5p drives palbociclib resistance. This miRNA is excreted from resistance cells, contained in exosomes, and confers the resistance phenotype to neighboring cells. The hypothesis is that expression and secretion of this miRNA is indicative of emerging CDK4/6 inhibitor resistance, and is useful as a biomarker.

Detection and analysis of patient serum miRNA is an emerging field with many useful applications. As described herein, abemacyclib-treated patient exosomes are analyzed, preferably those from the MONARCH 1 trial where abemacyclib was used as a single agent and pre- and post-treatment samples are available. Analysis of pre-treatment and post-treatment samples allows confirmation of previous findings in a much larger subset of patients and establishes whether exosomal, serum-derived miR-432-5p expression is useful as a biomarker of CDK4/6 inhibitor resistance and response. Importantly, comparative analysis of the pre- and post-CDK4/6 treatment exosomes allows direct determination of any increases in the miR-432-5p concentration in the blood of patients.

RNA isolation is performed using a method which retains small RNAs. For example, experiments have previously used Total Exosome RNA & Protein Isolation Kit (ThermoFisher).

As miRNAs are extremely small (~20 nt), detection by regular real-time PCR methods is not possible, as primer pairs exceed the length of the detected miR. As such, microRNAs are detected from RNA (total or exosomal) using poly-A tailing PCR. Briefly, a specific polymerase is used for the reverse transcription reaction which adds numerous (>150) adenine molecules to the 3' end of RNA transcripts. Using poly-A tailed cDNA, miRs are detected using one miR-sequence specific primer and one universal primer to the poly-A tail. This allows specific miR detection and quantification via classic SYBR green real-time qPCR. Many commercially available kits are available for detection of miRNAs, experiments have found exiqons miRCURY LNA™ system to be the most sensitive.

Using these methods of qPCR, the concentration of miR-432-5p within the serum exosomes obtained from abemcyclib treated patients is measured with great sensitivity. By comparing the relative expression of pre- and post-treatment samples with patient response, it is determined that miR-432-5p is a biomarker of emerging CDK4/6 inhibitor resistance.

Example 11: Clinical Validation

Described herein are clinical trials in which patients are administered an effective amount of a CDK4/6 inhibitor, e.g., palbociclib (PD0332991), ribociclib (LEE011), or abemaciclib (LY2835219).

A blood sample is periodically obtained from the patient. For example, a blood sample is obtained every 24 hours, every 48 hours, every 72 hours, every 96 hours, every 5 days, every 6 days, once per week, once per month, every two months, every three months, every six months, or once per year.

Exosomes are isolated from the blood sample, and the exosomes are analyzed for mIR-432-5p levels. For example, the expression level of the miRNA is detected via quantitative real-time reverse transcriptase polymerase chain reaction (real time RT-PCR). In other cases, the expression level of the miRNA is detected via an Affymetrix Gene Array hybridization, next generation sequencing, ribonucleic acid sequencing (RNA-seq), or nanoString nCounter expression panels.

The appearance of the micro-RNA (i.e., miR-432-5p) is a harbinger of the development of CDK4/6 inhibitor resistance in the patient. At the time of documented CDK4/6 inhibitor resistance by RECIST, administration of the CDK4/6 inhibitor is stopped. A tumor biopsy is performed to assess expression of mIR-432-5p, as well as CDK6, in the tumor cells.

Subsequently, the disappearance of the mIR-432-5p is monitored and detected by serial blood sampling and collection of exosomes. Exosomes are isolated from the blood sample, and the exosomes are analyzed for mIR-432-5p levels.

When the disappearance of mIR-432-5p is detected, a second tumor biopsy is performed to document reduction of levels of the micro-RNA and CDK6 in the tumor tissue.

Once the levels of the micro-RNA are decreased in the tumor tissue, the CDK4/6 inhibitor is re-introduced (i.e., administration of the CDK4/6 inhibitor is resumed), with the expectation that the patient's tumor may undergo response or stabilization once again.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of determining whether inhibition of cyclin-dependent kinase 4 (CDK4) and CDK6 in a human subject with neoplasia will result in clinical benefit in the subject comprising:
   obtaining a blood test sample from a human subject having neoplasia;
   determining the expression level of a micro ribonucleic acid (miRNA) in the test sample, wherein the miRNA comprises miR-432-5p;
   comparing the expression level of the miRNA in the test sample with the expression level of the miRNA in a reference sample;
   detecting a lower expression level of the miRNA in the test sample as compared to the expression level of the miRNA in the reference sample;
   determining that CDK4/6 inhibition will inhibit neoplasia in the subject; and
   administering a CDK4/6 inhibitor to the subject, thereby treating the neoplasia.

2. The method of claim 1, wherein the neoplasia comprises breast cancer or parotid cancer.

3. The method of claim 1, wherein the neoplasia comprises pancreatic cancer, acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, polycythemia vera, lymphoma, Hodgkin's disease, non-Hodgkin's disease, Waldenstrom's macroglobulinemia, heavy chain disease, a sarcoma and a carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, or retinoblastoma.

4. The method of claim 1, wherein the CDK4/6 inhibitor comprises palbociclib, abemacyclib, or ribociclib.

5. The method of claim 1, wherein the reference sample is obtained from healthy normal tissue, cancer that received a clinical benefit from CDK4/6 inhibition, or cancer that did not receive a clinical benefit from CDK4/6 inhibition.

6. The method of claim 1, wherein the reference sample is obtained from healthy normal tissue from the same individual as the test sample or one or more healthy normal tissues from different individuals.

7. The method of claim 1, wherein the expression level of the miRNA is detected via quantitative real-time reverse transcriptase polymerase chain reaction (real time RT-PCR).

8. The method of claim 1, further comprising treating the subject with a chemotherapeutic agent, radiation therapy, cryotherapy, hormone therapy, or immunotherapy.

9. The method of claim 1, wherein the expression level of the miRNA is detected via quantitative real-time reverse transcriptase polymerase chain reaction (real time RT-PCR).

10. A method of determining whether inhibition of cyclin-dependent kinase 4 (CDK4) and CDK6 in a human subject with neoplasia will result in clinical benefit in the subject comprising:
   obtaining a blood test sample from a human subject having neoplasia;
   determining the expression level of a micro ribonucleic acid (miRNA) in the test sample, wherein the miRNA comprises miR-432-5p;
   comparing the expression level of the miRNA in the test sample with the expression level of the miRNA in a reference sample;
   detecting a higher expression level of the miRNA in the test sample as compared to the expression level of the miRNA in the reference sample;
   determining that CDK4/6 inhibition will not result in clinical benefit in the subject;
   administering a miR-432-5p inhibitor to the subject, thereby re-sensitizing the neoplasia to CDK4/6 inhibition; and
   administering a CDK4/6 inhibitor to the subject, thereby treating the neoplasia.

11. The method of claim 10, wherein the neoplasia comprises breast cancer or parotid cancer.

12. The method of claim 10, wherein the neoplasia comprises pancreatic cancer, acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, polycythemia vera, lymphoma, Hodgkin's disease, non-Hodgkin's disease, Waldenstrom's macroglobulinemia, heavy chain disease, a sarcoma and a carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, or retinoblastoma.

13. The method of claim 10, wherein the reference sample is obtained from healthy normal tissue, cancer that received a clinical benefit from CDK4/6 inhibition, or cancer that did not receive a clinical benefit from CDK4/6 inhibition.

14. The method of claim 10, wherein the reference sample is obtained from healthy normal tissue from the same individual as the test sample or one or more healthy normal tissues from different individuals.

15. The method of claim 10, wherein the miR-432-5p inhibitor comprises a small molecule inhibitor, RNA interference (RNAi), or an antibody.

16. The method of claim 10, wherein the CDK4/6 inhibitor comprises palbociclib, abemacyclib, or ribociclib.

17. The method of claim 10, further comprising treating the subject with a chemotherapeutic agent, radiation therapy, cryotherapy, hormone therapy, or immunotherapy.

* * * * *